US011583562B2

(12) United States Patent
Lahusen et al.

(10) Patent No.: US 11,583,562 B2
(45) Date of Patent: Feb. 21, 2023

(54) VIRAL VECTORS FOR TREATING PARKINSON'S DISEASE

(71) Applicant: AMERICAN GENE TECHNOLOGIES INTERNATIONAL INC., Rockville, MD (US)

(72) Inventors: Tyler Lahusen, Rockville, MD (US); Charles David Pauza, Rockville, MD (US)

(73) Assignee: American Gene Technologies International Inc., Rockville, MD (US)

( * ) Notice: Subject to any disclaimer, the term of this patent is extended or adjusted under 35 U.S.C. 154(b) by 23 days.

(21) Appl. No.: 16/318,345

(22) PCT Filed: Jul. 20, 2017

(86) PCT No.: PCT/US2017/043157
§ 371 (c)(1),
(2) Date: Jan. 16, 2019

(87) PCT Pub. No.: WO2018/017882
PCT Pub. Date: Jan. 25, 2018

(65) Prior Publication Data

US 2019/0282639 A1 Sep. 19, 2019

Related U.S. Application Data

(60) Provisional application No. 62/365,316, filed on Jul. 21, 2016.

(51) Int. Cl.

| | |
|---|---|
| ***A61K 35/76*** | (2015.01) |
| ***A61K 31/7105*** | (2006.01) |
| ***C12N 15/113*** | (2010.01) |
| ***C12N 15/86*** | (2006.01) |
| ***A61K 45/06*** | (2006.01) |
| ***C12N 9/10*** | (2006.01) |

(52) U.S. Cl.
CPC .......... *A61K 35/76* (2013.01); *A61K 31/7105* (2013.01); *C12N 9/1077* (2013.01); *C12N 15/1137* (2013.01); *C12N 15/86* (2013.01); *A61K 45/06* (2013.01); *C12N 2310/14* (2013.01); *C12N 2310/531* (2013.01); *C12N 2320/32* (2013.01); *C12N 2330/51* (2013.01); *C12N 2740/16043* (2013.01); *C12Y 204/0203* (2013.01)

(58) Field of Classification Search
CPC .............. A61K 31/7105; C12N 9/1077; C12N 15/1137; C12N 15/86; C12N 2310/14; C12N 2310/531; C12N 2330/51; C12N 2740/16043; C12Y 204/0203
See application file for complete search history.

(56) References Cited

U.S. PATENT DOCUMENTS

| | | | |
|---|---|---|---|
| 5,668,255 | A | 9/1997 | Murphy |
| 5,674,703 | A | 10/1997 | Woo et al. |
| 6,156,514 | A | 12/2000 | Acevedo et al. |
| 6,399,383 | B1 | 6/2002 | Apt et al. |
| 6,635,472 | B1 | 10/2003 | Lauermann |
| 7,371,542 | B2 | 5/2008 | Ivanova et al. |
| 8,124,752 | B2 | 2/2012 | Bumcrot et al. |
| 8,287,857 | B2 | 10/2012 | Dudley et al. |
| 8,993,532 | B2 | 3/2015 | Hannon et al. |
| 9,522,176 | B2 | 12/2016 | DeRosa et al. |
| 9,527,904 | B2 | 12/2016 | Balazs |
| 9,834,790 | B1 | 12/2017 | Pauza et al. |
| 9,834,791 | B2 | 12/2017 | Zhang |
| 9,914,938 | B2 | 3/2018 | Pauza et al. |
| 10,023,880 | B2 | 7/2018 | Pauza et al. |
| 10,036,038 | B2 | 7/2018 | Pauza et al. |
| 10,036,040 | B2 | 7/2018 | Pauza et al. |
| 10,137,144 | B2 | 11/2018 | Pauza et al. |
| 10,208,295 | B2 | 2/2019 | DeRosa et al. |
| 10,233,464 | B2 | 3/2019 | Pauza et al. |
| 2002/0168345 | A1 | 11/2002 | Dong et al. |
| 2003/0013196 | A1 | 1/2003 | Engleman et al. |
| 2003/0096787 | A1 | 5/2003 | Perridcaudet et al. |
| 2003/0119770 | A1 | 6/2003 | Lai |
| 2003/0138444 | A1 | 7/2003 | Zavitz et al. |
| 2004/0142416 | A1 | 7/2004 | Laipis et al. |
| 2004/0161412 | A1 | 8/2004 | Penn et al. |
| 2004/0192629 | A1 | 9/2004 | Xu et al. |

(Continued)

FOREIGN PATENT DOCUMENTS

| | | |
|---|---|---|
| BR | 2515 | 3/2019 |
| CN | 101516365 | 8/2009 |

(Continued)

OTHER PUBLICATIONS

Yang H, Liang H, Chen J and Xu Y: Construction of PARP-1 gene silencing cell lines by lentiviral-mediated RNA interference technology. J Environ Health. 31:288-291, 377. 2014. English abstract only (Year: 2014).*

(Continued)

*Primary Examiner* — Richard A Schnizer

(74) *Attorney, Agent, or Firm* — DLA Piper LLP (US)

(57) ABSTRACT

A lentiviral vector system for expressing a lentiviral particle is disclosed. The lentiviral vector system includes a therapeutic vector, an envelope plasmid, and at least one helper plasmid. The lentiviral vector system can produce a lentiviral particle for inhibiting PARP expression in neuron cells of a subject afflicted with Parkinson's disease.

4 Claims, 8 Drawing Sheets

Specification includes a Sequence Listing.

(56) References Cited

U.S. PATENT DOCUMENTS

| | | | |
|---|---|---|---|
| 2004/0214158 A1 | 10/2004 | Sethi et al. | |
| 2004/0248296 A1 | 12/2004 | Beresford et al. | |
| 2005/0019927 A1 | 1/2005 | Markus et al. | |
| 2005/0138677 A1 | 6/2005 | Pfister et al. | |
| 2006/0057553 A1 | 3/2006 | Aguilar-Cordova | |
| 2006/0183230 A1 | 8/2006 | Silla et al. | |
| 2006/0246520 A1 | 11/2006 | Champagne et al. | |
| 2007/0026521 A1 | 2/2007 | Colosi | |
| 2007/0141679 A1 | 6/2007 | Sodroski | |
| 2007/0203333 A1 | 8/2007 | McSwiggen et al. | |
| 2008/0003225 A1 | 1/2008 | Vie et al. | |
| 2008/0003682 A1 | 1/2008 | Lois-Caballe et al. | |
| 2008/0039413 A1 | 2/2008 | Morris et al. | |
| 2008/0131940 A1 | 6/2008 | Chiu | |
| 2008/0153737 A1 | 6/2008 | Lieberman et al. | |
| 2008/0199961 A1 | 8/2008 | Rasko et al. | |
| 2008/0227736 A1 | 9/2008 | Chen et al. | |
| 2008/0293142 A1 | 11/2008 | Liu et al. | |
| 2009/0148936 A1 | 6/2009 | Stout et al. | |
| 2009/0304688 A1 | 12/2009 | Fournie et al. | |
| 2010/0017911 A1 | 1/2010 | Dawson et al. | |
| 2010/0069372 A1 | 3/2010 | Kazantsev | |
| 2010/0119511 A1 | 5/2010 | Wang et al. | |
| 2010/0120155 A1 | 5/2010 | Brennan et al. | |
| 2010/0286166 A1 | 11/2010 | Rodriguez et al. | |
| 2010/0316676 A1 | 12/2010 | Sanders | |
| 2011/0008803 A1 | 1/2011 | Stockwell et al. | |
| 2011/0177155 A1 | 7/2011 | Peer et al. | |
| 2011/0207226 A1 | 8/2011 | Ni et al. | |
| 2012/0053223 A1 | 1/2012 | Benkirane et al. | |
| 2012/0027725 A1 | 2/2012 | Galvin | |
| 2012/0114607 A1 | 5/2012 | Lai et al. | |
| 2012/0034197 A1 | 8/2012 | Young et al. | |
| 2012/0201794 A1 | 9/2012 | Chen et al. | |
| 2013/0078276 A1 | 3/2013 | Robinson et al. | |
| 2013/0090371 A1 | 4/2013 | Lu et al. | |
| 2013/0142766 A1 | 6/2013 | Dodo et al. | |
| 2013/0211380 A1 | 8/2013 | Aquino et al. | |
| 2014/0155468 A1 | 6/2014 | Gregory et al. | |
| 2014/0162894 A1 | 6/2014 | Hatchwell et al. | |
| 2014/0178340 A1 | 6/2014 | Robbins et al. | |
| 2014/0234958 A1 | 8/2014 | Kashara et al. | |
| 2014/0248277 A1 | 9/2014 | Hoffman et al. | |
| 2014/0336245 A1 | 11/2014 | Mingozzi et al. | |
| 2015/0010578 A1 | 1/2015 | Balazs et al. | |
| 2015/0018539 A1 | 1/2015 | Fellmann | |
| 2015/0126580 A1 | 5/2015 | DePinho et al. | |
| 2015/0132255 A1 | 5/2015 | Sorensen et al. | |
| 2015/0176006 A1 | 6/2015 | Krause et al. | |
| 2016/0060707 A1 | 3/2016 | Goldenberg et al. | |
| 2016/0243169 A1 | 8/2016 | Chen et al. | |
| 2016/0289681 A1 | 10/2016 | Rossi | |
| 2017/0015976 A1 | 1/2017 | Nelson | |
| 2017/0028036 A1 | 2/2017 | Mingozzi et al. | |
| 2017/0037369 A1 | 2/2017 | Ramsborg et al. | |
| 2017/0335344 A1 | 11/2017 | Pauza et al. | |
| 2018/0010147 A1 | 1/2018 | Pauza | |
| 2018/0142257 A1 | 5/2018 | Pauza | |
| 2018/0142258 A1 | 5/2018 | Pauza | |
| 2018/0161455 A1 | 6/2018 | Pauza | |
| 2018/0177866 A1 | 6/2018 | Pauza | |
| 2018/0195046 A1* | 7/2018 | Deng | A61K 35/545 |
| 2018/0195050 A1 | 7/2018 | Szalay | |
| 2018/0256624 A1 | 9/2018 | Panza | |
| 2018/0305716 A1 | 10/2018 | Pauza | |
| 2018/0355032 A1 | 12/2018 | Roberts | |
| 2019/0046633 A1 | 2/2019 | Pauza et al. | |
| 2019/0062786 A1 | 2/2019 | Pauza et al. | |
| 2019/0078096 A1 | 3/2019 | Lahusen et al. | |
| 2019/0083523 A1 | 3/2019 | Pauza | |
| 2019/0388456 A1 | 12/2019 | Pauza et al. | |
| 2020/0063161 A1 | 2/2020 | Pauza | |
| 2020/0087682 A1 | 3/2020 | Lahusen et al. | |
| 2020/0109417 A1 | 4/2020 | Pauza et al. | |
| 2020/0155590 A1 | 5/2020 | Zhennan | |
| 2020/0181645 A1 | 6/2020 | Pauza | |
| 2020/0318081 A1 | 10/2020 | Lahusen et al. | |
| 2021/0047644 A1 | 2/2021 | Lahusen | |

FOREIGN PATENT DOCUMENTS

| | | | |
|---|---|---|---|
| CN | 101679466 | 3/2010 | |
| CN | 101805750 | 8/2010 | |
| CN | 103184224 | 7/2013 | |
| CN | PCT/CN2015/086854 | * 8/2015 | C12N 5/00 |
| CN | 105112370 | 12/2015 | |
| CN | 108883100 | 11/2018 | |
| EP | 1647595 | 4/2006 | |
| EP | 3402483 | 11/2018 | |
| EP | 3413926 | 12/2018 | |
| EP | 3426777 | 1/2019 | |
| EP | 3468617 | 4/2019 | |
| EP | 3468618 | 4/2019 | |
| EP | 3481418 | 5/2019 | |
| EP | 3481435 | 5/2019 | |
| IN | 201947000153 | 2/2019 | |
| JP | 2002506652 | 3/2002 | |
| JP | 2007-527240 | 9/2007 | |
| JP | 2008518591 | 6/2008 | |
| JP | 2008-538174 | 10/2008 | |
| JP | 2012508591 | 4/2012 | |
| JP | 2013-5300152 | 7/2013 | |
| JP | 2015-518838 | 7/2015 | |
| JP | 2016-502404 | 1/2016 | |
| WO | 199947691 | 9/1999 | |
| WO | 2002020554 | 3/2002 | |
| WO | 2003093436 | 11/2003 | |
| WO | 2004053137 | 6/2004 | |
| WO | 2005028634 | 3/2005 | |
| WO | 2005033282 | 4/2005 | |
| WO | 2006039721 | 4/2006 | |
| WO | 2006048215 | 5/2006 | |
| WO | 2007000668 | 1/2007 | |
| WO | 2007015122 | 2/2007 | |
| WO | 2007132292 | 11/2007 | |
| WO | 2007133674 | 11/2007 | |
| WO | WO2008/025025 | 2/2008 | |
| WO | 2008090185 | 7/2008 | |
| WO | 2009100928 | 8/2009 | |
| WO | 2009147445 | 12/2009 | |
| WO | 2010051521 | 5/2010 | |
| WO | 2010117974 | 10/2010 | |
| WO | 2010127166 | 11/2010 | |
| WO | 2011008348 | 1/2011 | |
| WO | 2011071476 | 6/2011 | |
| WO | 2011119942 | 9/2011 | |
| WO | 2012048303 | 4/2012 | |
| WO | 2012061075 | 5/2012 | |
| WO | WO2012145624 | 10/2012 | |
| WO | 2013096455 | 6/2013 | |
| WO | 2014016817 | 1/2014 | |
| WO | 2014117050 | 7/2014 | |
| WO | 2014187881 | 11/2014 | |
| WO | 2015017755 | 2/2015 | |
| WO | 2015042308 | 3/2015 | |
| WO | 2015061491 | 4/2015 | |
| WO | 2015078999 | 6/2015 | |
| WO | WO2015164759 | 10/2015 | |
| WO | 2016046234 | 3/2016 | |
| WO | 2016061232 | 4/2016 | |
| WO | WO2016061232 | 4/2016 | |
| WO | 2016069716 | 5/2016 | |
| WO | 2016200997 | 7/2016 | |
| WO | WO2016189159 | 12/2016 | |
| WO | 2017007994 | 1/2017 | |
| WO | 20170068077 | 4/2017 | |
| WO | 2017100551 | 6/2017 | |
| WO | 2017123918 | 7/2017 | |
| WO | 2017139065 | 8/2017 | |
| WO | WO2017139065 | 8/2017 | |
| WO | 2017156311 | 9/2017 | |
| WO | 20170173453 | 10/2017 | |
| WO | 2017213697 | 12/2017 | |
| WO | 2017214327 | 12/2017 | |

(56) References Cited

FOREIGN PATENT DOCUMENTS

| | | |
|---|---|---|
| WO | 2018009246 | 1/2018 |
| WO | 2018009847 | 1/2018 |
| WO | 2018017882 | 1/2018 |
| WO | 2018126112 | 7/2018 |
| WO | 2018129540 | 7/2018 |
| WO | WO2018126112 | 7/2018 |
| WO | 20180148443 | 8/2018 |
| WO | 2018187231 | 10/2018 |
| WO | 2018232359 | 12/2018 |
| WO | WO2019070674 | 4/2019 |
| WO | 2020097049 | 5/2020 |
| WO | 2020243717 | 12/2020 |

OTHER PUBLICATIONS

Cronin et al (Curr Gene Ther. Author manuscript; available in PMC Feb. 15, 2006, 19 pages) (Year: 2006).*
Cannon et al (Experimental Neurology 228 (2011) 41-52) (Year: 2011).*
Clontech pLVX-shRNA1 Vector Information (PT4051-5 Catalog No. 632177, 2008, retrieved from http://www.takara.co.kr/file/manual/pdf/PT4051-5.pdf) (Year: 2008).*
High-Efficiency Lentiviral Packaging System (Clontechniques Jan. 2008, pp. 8-9), retrieved from https://catalog.takara-bio.co.jp/PDFFiles/200802_08.pdf) (Year: 2008).*
Wu, X. et al. (Mol. Ther. 2(1):47-55, 2000) (Year: 2000).*
Kaalund etal (Front. Neurosci 13:1398, 2020, 10 pages) (Year: 2020).*
Hee Yeon Kim., "Farnesyl diphosphate synthase in important for the maintenance of glioblastoma stemness," Experimental & Molecular Medicine, (2018).
Hong Wang., "Indirect Stimulation of Human V2V2 Cells Through Alterations in Isoprenoid Metabolism," The Journal of Immunology, (2011).
Z. Li, "Inhibition of farnesyl pyrophosphate synthase prevents angiotensin II-induced cardiac fibrosis in vitro," Clinical & Experimental Immunology, (2014).
Xiaofeng Jiang, "A novel EST-derived RNAi screen reveals a critical role for farnesyl diphosphate in B2-adreneriegic receptor internalization and down-regulation," The FASEB Journal, vol. 26, pp. 1-13(1995).
Jian Yang, "Lentiviral-Mediated Silencing of Farnesyl Pyrophosphate Synthase through RNA Interference in Mice," Biomed Research International, vol. 2015, Article ID 914026, 6 pages, (2015).
Yang Ye, "Knockdown of farnesyl pyrophosphate synthase prevents angiotensin II-medicated cardiac hypertrophy," The International Journal of Biochemistry & Cell Biology, vol. 42, pp. 2056-2064, (2010).
Jianqiang Li, "Reduced Expression of Mevalonate Pathway Enzyme Farnesyl Pyrophosphate Synthase Unveils Recognition of Tumor Cells by V9V2 Cells," The Journal of Immunology, pp. 8118-8124, (2019).
Daryl S. Schiller, "Parameters Influencing Measurement of the Gag Antigen-Specific T-Proliferative Response to HIV Type 1 Infection," AIDS Research and Human Retroviruses, vol. 16, No. 3, pp. 259-271, (2000).
PCT; International Search Report dated Jul. 22, 2019 in the Application No. PCT/US2019/24410.
PCT; Written Opinion of the International Search Report dated Jul. 22, 2019 in the Application No. PCT/US2019/24410.
PCT; International Preliminary Report on Patentability dated Jul. 9, 2019 in the Application No. PCT/US2018/012998.
USPTO; Notice of Allowance dated Jun. 18, 2019 in the U.S. Appl. No. 16/182,443.
USPTO; Notice of Allowance dated Jul. 3, 2019 in U.S. Appl. No. 16/182,443.
USPTO; Restriction Requirement dated Jul. 12, 2019 in U.S. Appl. No. 15/736,284.
USPTO; Advisory Action dated Jul. 23, 2019 in U.S. Appl. No. 15/736,284.
USPTO; Notice of Allowance dated Aug. 14, 2019 in U.S. Appl. No. 16/008,991.
USPTO; Notice of Allowance dated Sep. 25, 2019 in U.S. Appl. No.16/218,010.
USPTO; Final Office Action dated Jul. 1, 2019 in U.S. Appl. No. 16/132,247.
USPTO; Notice of Allowance dated Jul. 19, 2019 in U.S. Appl. No. 16/132,247.
EPO; European Search Report dated Aug. 12, 2019 in the EP Application No. 17764128.9.
EPO; Supplementary European Search Report dated Sep. 6, 2019 in the Application No. 17750547.6.
Vargas, J. Jr. et al., "Conditionally replicating lentiviral-hybrid episomal vectors for suicide gene therapy," Antiviral Res. Dec. 2008 vol. 80 No. 3, pp. 288-294.
Thompson et al., "Alkylamines cause Vγ9Vδ2 T-cell activation and proliferation by inhibiting the mevalonate pathway," Blood, Jan. 15, 2006, vol. 107, pp. 651-654.
Gober et al., "Human T Cell Receptor γδ Cells Recognize Endogenous Mevalonate Metabolites in Tumor Cells," J. of Experimental Med., Jan. 20, 2003, vol. 197, pp. 163-168.
Goepfert, et al., "Specificity and 6-Month Durability of Immune Responses Induced by DNA and Recombinant Modified Vaccinia Ankara Vaccines Expressing HIV-2 Virus-Like Particles," J. Infectious Diseases, Jul. 1, 2014, vol. 210, pp. 99-110.
Human papillomavirus type 16 (HPV16), complete genome; GenBank: K02718.1; Publication [online], Mar. 18, 1994, https://www.ncbi.nlm.nih.gov/nucleotide/333031?report=genbank&log$=nucltop&blast_rank=22&RID=H3E1THFU014; pp. 1-4.
{Long control region} [human papillomavirus, type 16, Genomic, 860 nt]; Accession S60559. Publication [online]. May 7, 1993, https://www.ncbi.nlm.nih.gov/nucleotide/237343?report=genbank&log$=nucltop&blast_rank=1&RID=H3FCKA00014; pp. 1.
Tebas, P. et al., "Antiviral effects of autologous CD4 T cells genetically modified with a conditionally replicating lentiviral vector expressing long antisense to HIV," Blood, 2013, vol. 121, No. 9, pp. 1524-1533.
Tebas, p. et al., "Gene Editing of CCR5 in Autologous CD4 T Cells of Persons Infected with HIV," The New England Journal of Medicine, vol. 370 (10), pp. 901-910, Mar. 6, 2014.
Li et al., "Reduced Expression of the Mevalonate Pathway Enzyme Famesyl Pyrophosphate Synthase Unveils Recognition of Tumor Cells by Vy2Vδ2 T Cells," J. of Immunology, 2009, vol. 182, pp. 8118-8124.
Wang et al., "Indirect Stimulation of Human Vy2Vδ2 T Cells through Alterations in Isoprenoid Metabolism," J. of Immunology, vol. 187 pp. 5099-5113, (Nov. 15, 2011).
Stunkel et al., "The Chromatin Structure of the Long Control Region of Human Papillomavirus Type 16 Repress Viral Oncoprotein Expression," Journal of Virology, vol. 73, No. 3, pp. 1918-1930 (Mar. 1999).
Lu et al., "Anti-sense-Mediated Inhibition of Human Immunodeficiency Vims (HIV) Replication by Use of an HIV Type 1-Based Vector Results in Severely Attenuated Mutants Incapable of Developing Resistance," Journal of Virology, vol. 79, No. 13, pp. 7079-7088 (Jul. 2004).
Dieli et al., "Targeting Human yδ T Cells with Zoledronate and Interleukin-2 for Immunotherapy of Hormone-Refractory Prostate Cancer," Europe PMC Funders Group, Cancer Research, vol. 67(15), pp. 7450-1451, (Aug. 1, 2007).
GenBank Accession No. S60559 "(long control region) [human papillomavirus, type 16, Genomic, 860 nt]" May 7, 1993 [located online Nov. 21, 2017 at https://ncbi.nlm.nih.gov/nuccore/S60559] entire DNA sequence.
GenBank Accession No. JG619773, MNESC1NG-T3-001_L15_Feb. 6, 2009_054 MNESC1NG cell culture from Mahonia nervosa Berberis nervosa cDNA, mRNA sequence, Feb. 13, 2014 (online). [Retrieved on Dec. 5, 2017], Retrieved from the internet:<URL: https://www.ncbi.nlm.nih.gov/nucest/JG619773 > entire document.
Moser et al., "yd T cells: novel initiators of adaptive immunity," Immunological Reviews, vol. 215, pp. 89-102 (Feb. 2, 2007).

(56) References Cited

OTHER PUBLICATIONS

Capietto, A. H. et al., "Stimulated γδ T Cells Increase the in Vivo Efficacy of Trastuzumab in HER-2+ Breast Cancer," J Immunology, vol. 187(2), pp. 1031-1038, (2011).
Chen, Z. and M. S. Freedman, "CD16+ γδ T Cells Mediate Antibody Dependent Cellular Cytotoxicity: Potential Mechanism in the Pathogenesis of Multiple Sclerosis," Clin Immunology, vol. 128(2), pp. 219-227, (2008).
Couzi, L. et al., "Antibody-Dependent Anti-Cytomegalovirus Activity of Human γδ T Cells Expressing CD16 (FcγRIIIa)," Blood, vol. 119(6), pp. 1418-1427, (2012).
Fisher, J. P. et al., "Effective Combination Treatment of GD2-Expressing Neuroblastoma and Ewing's Sarcoma Using Anti-GD2 ch14.18/CHO Antibody with Vγ9Vδ2+ γδT Cells," OncoImmunology, vol. 5(1), pp. e1025194, (2016).
Gertner-Dardenne, J. et al., "Bromohydrin pyrophosphate enhances antibody-dependent cell-mediated cytotoxicity induced by therapeutic antibodies," Blood 113(20): 4875-4884, (2009).
Poonia, B. and C. D. Panza, "Gamma delta T cells from HIV+ donors can be expanded in vitro by zoledronate/interleukin-2 to become cytotoxic effectors for antibody-dependent cellular cytotoxicity," Cytotherapy 14(2): 173-181, (2012).
Schiller, C. B. et al., "CD19-Specific Triplebody SPM-1 Engages NK and γδ T Cells for Rapid and Efficient Lysis of Malignant B-Lymphoid Cells," Oncotarget, vol. 7(50), pp. 83392-83408, (2016).
Tokuyama, H. et al., "Vγ9Vδ2 T Cell Cytotoxicity Against Tumor Cells is Enhanced by Monoclonal Antibody Drugs—Rituximab and Trastuzumab," Int J Cancer, vol. 122(11), pp. 2526-2534, (2008).
Zufferey et al., "Self-Inactivating Lentivirus Vector for Safe and Efficient In Vivo Gene Delivery," Journal of Virology, vol. 72(12), pp. 9873-9880, (1998).
Ostertag et al., "Brain Tumor Eradication and Prolonged Survival from Intratumoral Conversion of 5-Fluorocytosine to 5-fluorouracil Using a Nonlytic Retroviral Replicating Vector," Neoro-Oncology 14(2), pp. 145-159, Feb. 2012.
Twitty et al., "Retroviral Replicating Vectors Deliver Cytosine Deaminase Leading to Targeted 5-Fluorouracil-Mediated Cytotoxicity in Multiple Human Cancer Types," Human Gene Therapy Methods, 27(1), pp. 17-31, Feb. 1, 2016.
Charron et al., "Dominant-Negative Interference in the Pahenu2 Mouse Model of PKU: Effectiveness of Vectors Expressing Either Modified Forms of Phenylalanine Hydroxylase (PAH) or Ribozymes Plus a Hardened PAH mRNA," Molecular Therapy, vol. 11, pp. S163-S164, (2005).
Fusetti, et al., "Structure of Tetrameric Human Phenylalanine Hydroxylase and Its Implications for Phenylketonuria," J. Bio. Chem., vol. 273, No. 27, pp. 16962-16967 (1998).
Hafid et al., "Phenylketonuria: A Review of Current and Future Treatments," Translational Pediatrics, vol. 4(4), pp. 304-317, (2015).
Blau et al., "Phenylketonuria," The Lancet, vol. 376(9750), pp. 1417-1427, (2010).
Chandler et al., "Vector Design Influences Hepatic Genotoxicity After Adeno-Associated Virus Gene Therapy," Journal of Clinical Investigation, vol. 125(2), pp. 870-880, (2015).
Christophersen et al., "A Technique of Transumbilical Portal Vein Catheterization in Adults," The Archives of Surgery, vol. 95(6), pp. 960-963, (1967). (Abstract Only).
Bartholome, "Genetics and Biochemistry of the Phenylketonuria—Present State," Human Genetics, vol. 51(3), pp. 241-245, (1979).
Donsante et al., "AAV Vector Integration Sites in Mouse Hepatocellular Carcinoma," Science, vol. 317(5837, p. 477, (2007).
Eisensmith et al., "Multiple Origins for Phenylketonuria in Europe," American Journal of Human Genetics, vol. 51(6), pp. 1355-1365, (1992).
Fisher et al., "The Inhibition of Phenylalanine and Tyrosine Hydroxylases by High Oxygen Levels," Journal of Neurochemistry, vol. 19(5), pp. 1359-1365, (1972). (Abstract Only).
Grisch-Chan et al., "Low-Dose Gene Therapy for Murine PKU Using Episomal Naked DNA Vectors Expressing PAH from Its Endogenous Liver Promoter," Molecular Therapy Nucleic Acids, vol. 7, pp. 339-349, (2017).
Guldberg et al., "Aberrant Phenylalanine Metabolism in Phenylketonuria Heterozygotes," Journal of Inherited Metabolic Disease, vol. 21(4), pp. 365-372, (1998).
Kaufman et al., "A Model of Human Phenylalanine Metabolism in Normal Subjects and in Phenylketonuric Patients," Proceedings of the National Academy of Sciences USA, vol. 96(6), pp. 3160-3164, (1999).
Kaufman et al., "Phenylalanine Hydroxylase Activity in Liver Biopsies from Hyperphenylalaninemia Heterozygotes: Deviation from Proportionality with Gene Dosage," Pediatric Research, vol. 9(8), pp. 632-634, (1975).
Longo et al., "Single-Dose, Subcutaneous Recombinant Phenylalanine Ammonia Lyase Conjugated with Polyethylene Glycol in Adult Patients with Phenylketonuria: An Open-Label, Multicentre, Phase 1 Dose-Escalation Trial," The Lancet, vol. 384(9937), pp. 37-44, (2014).
Mochizuki et al., "Long-Term Correction of Hyperphenylalaninemia by AAV-Mediated Gene Transfer Leads to Behavioral Recovery in Phenylketonuria Mice," Gene Therapy, vol. 11(13), pp. 1081-1086, (2004).
Nault et al., "Adeno-Associated Virus Type 2 as an Oncogenic Virus in Human Hepatocellular Carcinoma," Molecular & Cellular Oncology, vol. 3(2), p. e1095271, (2016).
Oh et al., "Reversal of Gene Expression Profile in the Phenylketonuria Mouse Model After Adeno-Associated Virus Vector-Mediated Gene Therapy," Molecular Genetics and Metabolism, vol. 86(Supp. 1), pp. S124-S132, (2005).
Oh et al., "Long-Term Enzymatic and Phenotypic Correction in the Phenylketonuria Mouse Model by Adeno-Associated Virus Vector-Mediated Gene Transfer," Pediatric Research, vol. 56(2), pp. 278-284, (2004).
Pan et al., "Biodistribution and Toxicity Studies of VSVG-Pseudotyped Lentiviral Vector After Intravenous Administration in Mice with the Observation of in Vivo Transduction of Bone Marrow," Molecular Therapy, vol. 6(1), pp. 19-29, (2002).
Shedlovsky et al., "Mouse Models of Human Phenylketonuria," Genetics, vol. 134(4), pp. 1205-1210, (1993).
Yagi et al., "Complete Restoration of Phenylalanine Oxidation in Phenylketonuria Mouse by a Self-Complementary Adeno-Associated Virus Vector," Journal of Gene Medicine, vol. 13(2), pp. 114-122, (2011).
Yano et al., "Evaluation of Tetrahydrobiopterin Therapy with Large Neutral Amino Acid Supplementation in Phenylketonuria: Effects on Potential Peripheral Biomarkers, Melatonin and Dopamine, for Brain Monoamine Neurotransmitters," PLoS One, vol. 11(8), p. e0160892, (2016).
Mason et al., "Inactivated Simian Immunodeficiency Virus-Pulsed Autologous Fresh Blood Cells as an Immunotherapy Strategy," Journal of Virology, vol. 83(3), pp. 1501-1510, (2009).
Blick et al., "Cyclophosphamide Enhances SB-728-T Engraftment to Levels Associated with HIV-RNA Control," CROI Conference on Retroviruses and Opportunistic Infections, Boston, Massachusetts, p. 141, (2014), (Abstract Only).
De Rose et al., "Safety, Immunogenicity and Efficacy of Peptide-Pulsed Cellular Immunotherapy in Macaques," Journal of Medical Primatology, vol. 27(2), pp. 69-78, (2008).
Smith et al., "Developments in HIV-1 Immunotherapy and therapeutic Vaccination," F1000Prime Reports, vol. 6, p. 42, (2014).
Charron, "Gene Therapy for Phenylketonuria: Dominant-Negative Interference in a Recessive Disease," Dissertation, University of Florida 2005, http://etd.fcla.edu/UF/UFE0011392/charron_c.pdf>, (retrieved Jul. 26, 2018) (2005).
Ding et al., "Administration-Route and Gender-Independent Longterm Therapeutic Correction of Phenylketonuria (PKU) in a Mouse Model by Recombinant Adeno-Associated Virus 8 Pseudotyped Vector-Mediated Gene Transfer," Gene Therapy, vol. 13, pp. 583-587, (Dec. 1, 2005).

(56) References Cited

OTHER PUBLICATIONS

Nowacki et al., "The PAH Mutation Analysis Consortium Database: Update 1996," Nucleic Acid Research, vol. 25(1), pp. 139-142, (Jan. 1, 1997).
Condiotti et al., "Prolonged Liver-Specific Transgene Expression by a Non-Primate Lentiviral Vector," Biochemical and Biophysical Research Communications, vol. 320(3), pp. 998-1006, (Jul. 30, 2004).
Wang et al., "Butyrophilin 3A1 Plays an Essential Role in Prenyl Pyrophosphate Stimulation of Human Vg2Vd2 T Cells," Journal of Immunology, vol. 191(3), pp. 1029-1042, (Jul. 5, 2013).
Jiang et al., "A Novel EST-Derived RNAi Screen Reveals a Critical Role for Farnesyl Diphosphate Synthase in Beta2-Adrenergic Receptor Internalization and Down-Regulation," FASEB Journal, vol. 26(5), pp. 1-13, (Jan. 25, 2012).
Miettinen et al., "Mevalonate Pathway Regulates Cell Size Homeostasis and Proteostasis Through Autophagy," Cell Reports, vol. 13(11), pp. 2610-2620, (Dec. 2015).
Tolmachov, "Designing Lentiviral Gene Vectors," Viral Gene Therapy, Chapter 13, pp. 263-284, (2011).
Tracey, "Human DNA Sequence from Clone RP1-288M22 on Chromosome 6q 12-13," Complete Sequence, National Center for Biotechnology. GenBank Entry. Retrieved from the internet: <https://www.ncbi.nlm.nih.gov/nucleotide/AL035467.23?report=genbank&log$=nucltop&blast_rank=1&RID=UUD4GX2D014>; pp. 1-34, (Jan. 24, 2013).
Gorziglia et al., "Elimination of Both E1 and E2A from Adenovirus Vectors Further Improves Prospects for In Vivo Human gene Therapy," Journal of Virology, vol. 70(6), pp. 4173-4178, (1996).
Vargas et al., "Novel Integrase-Defective Lentiviral Episomal Vectors for Gene Transfer," Human Gene Therapy, vol. 15(4), pp. 361-372, (Apr. 2004).
Wendelburg et al., "An Enhanced EBNA1 Variant with reduced IR3 Domain for Long-Term Episomal Maintenance and Transgene Expression of ORIP-Based Plasmids in Human Cells," Gene Therapy, vol. 5, pp. 1389-1399, (Oct. 1998).
Westerhout et al., "A Conditionally Replicating HIV-Based Vector that Stably Expresses an Antiviral shRNA Against HIV-1 Replication," Molecular Therapy: The Journal of the American Society of Gene Therapy, vol. 14(2), pp. 268-275, (May 2006).
Lam et al., "T-Cell Therapies for HIV," Immunotherapy, Future Medicine, vol. 5(4), pp. 407-414, (Apr. 2013).
Munoz et al., "Ex Vivo Expansion and Lentiviral Transduction of Macaca Nemestrina CD4 + T Cells," Journal of Medical Primatology, vol. 38(6), pp. 438-443, (Dec. 2009).
Porichis et al., "HIV-Specific CD4 T Cells and Immune Control of Viral Replication," Current Opinion in HIV and Aids, vol. 6(3), pp. 174-180, (May 2011).
Kavanagh et al., "Expansion of HIV-Specific CD4+ and CD8+ T Cells by Dendritic Cells Transfected with mRNA Encoding Cytoplasm- or Lysosome-Targeted Nef," Blood, American Society of Hematology, vol. 107(5), pp. 1963-1969, (Mar. 2006).
Akinsheye et al., "Fetal Hemoglobin in Sickle Cell Anemia," Blood, vol. 118(1), pp. 19-27, (2011).
Lin et al., "Up-Regulation of Bcl-2 is Required for the Progression of Prostate Cancer Cells from an Androgen-Dependent to an Androgen-Independent Growth Stage," Cell Research, vol. 17, pp. 531-536, (2007).
GenBank Sequence M65141.1 Retrieved from the Internet <URL:https://www.ncbi.ntm.nih.gov/nuccore/M65141.1. Especially Sequence, nt 301-420, (Retrieved Mar. 31, 2019).
PCT: International Search Report dated Nov. 7, 2016 in Application No. PCT/US2016/036519.
PCT: Written Opinion dated Nov. 7, 2016 in Application No. PCT/US2016/036519.
PCT: International Search Report dated Oct. 19, 2016 in Application No. PCT/US2016/041456.
PCT: Written Opinion dated Oct. 19, 2016 in Application No. PCT/US2016/041456.
PCT: International Search Report dated Jul. 20, 2017 in Application No. PCT/US2017/043157.
PCT: Written Opinion dated Jul. 20, 2017 in application No. PCT/US2017/043157.
PCT: International Search Report dated Jun. 9, 2017 in Application No. PCT/US2016/066185.
PCT: Written Opinion dated Jun. 9, 2017 in Application No. PCT/US2016/066185.
PCT: International Search Report dated Jul. 17, 2017 in Application No. PCT/US2017/013019.
PCT: Written Opinion dated Jul. 17, 2017 in Application No. PCT/US2017/013019.
PCT: International Search Report dated May 26, 2017 in Application No. PCT/US2017/013399.
PCT: Written Opinion dated May 26, 2017 in Application No. PCT/US2017/013399.
PCT: International Search report dated Aug. 25, 2017 in Application No. PCT/US2017/021639.
PCT: Written Opinion dated Aug. 25, 2017 Application No. PCT/US2017/021639.
PCT: International Search Report dated Nov. 8, 2017 Application No. PCT/US2017/041168.
PCT: Written Opinion dated Nov. 8, 2017 in Application No. PCT/US2017/041168.
PCT: International Search Report dated Dec. 15, 2017 in Application No. PCT/US2017/36433.
PCT: Written Opinion dated Dec. 15, 2017 in Application No. PCT/US2017/36433.
PCT: International Search Report date Jul. 14, 2017 in Application No. PCT/US2017/013024.
PCT: Written Opinion dated Jul. 14, 2017 in application No. PCT/US2017/013024.
PCT: International Search Report dated May 29, 2018 in Application No. PCT/US2018/012998.
PCT: Written Opinion dated May 29, 2018 in Application No. PCT/US2018/012998.
PCT; International Search Report dated Sep. 24, 2018 in Application No. PCT/US2018/025733.
PCT; Written Opinion dated Sep. 24, 2018 in Application No. PCT/US2018/025733.
PCT; International Search Report dated Nov. 9, 2018 in Application No. PCT/US2018/037924.
PCT; Written Opinion dated Nov. 9, 2018 in Application No. PCT/US2018/037924.
PCT; Invitation to Pay Additional Fees in Application No. PCT/US2018/053919 dated Feb. 22, 2019.
PCT; Written Opinion dated Apr. 12, 2019 in Application No. PCT/US2018/053919.
PCT; International Search Report dated Apr. 12, 2019 in Application No. PCT/ US2018/053919.
USPTO; Requirement for Restriction dated Oct. 23, 2017 in U.S. Appl. No. 15/668,223.
USPTO; Notice of Allowance dated Nov. 2, 2017 in U.S. Appl. No. 15/652,080.
USPTO; Non-Final Office Action dated Feb. 22, 2018 in U.S. Appl. No. 15/850,937.
USPTO; Non-Final Office Action dated Feb. 22, 2018 in U.S. Appl. No. 15/849,062.
USPTO; Non-Final Office Action dated Feb. 22, 2018 in U.S. Appl. No. 13/333,882.
USPTO; Notice of Allowance dated Mar. 26, 2018 in U.S. Appl. No. 15/668,223.
USPTO; Notice of Allowance dated Apr. 23, 2018 in U.S. Appl. No. 15/850,937.
USPTO; Notice Allowance dated Apr. 26, 2018 in U.S. Appl. No. 15/849,062.
USPTO; Requirement for Restriction dated Jul. 12, 2018 in U.S. Appl. No. 15/736,284.
USPTO; Invitation to Pay Additional Fees And, Where Applicable, Protest Fee dated Jul. 17, 2018 in Application No. PCT/US2018/25733.
USPTO; Requirement for Restriction dated Aug. 3, 2018 in U.S. Appl. No. 16/011,550.

(56) References Cited

OTHER PUBLICATIONS

USPTO; Non-Final Office Action dated Jun. 15, 2018 in U.S. Appl. No. 15/904,131.
USPTO; Notice of Allowance dated Aug. 10, 2018 in U.S. Appl. No. 15/904,131.
USPTO; Final Office Action dated Aug. 27, 2018 in U.S. Appl. No. 13/333,882.
USPTO; Non-Final Office Action dated Sep. 19, 2018 in U.S. Appl. No. 16/011,550.
USPTO; Invitation to Pay Additional Fees And, Where Applicable, Protest Fee dated Sep. 11, 2018 in Application No. PCT/US2018/37924.
USPTO; Non-Final Office Action dated Oct. 19, 2018 in U.S. Appl. No. 15/736,284.
USPTO; Notice of Allowance dated Oct. 31, 2018 in U.S. Appl. No. 16/011,550.
USPTO; Advisory Action dated Nov. 16, 2018 in U.S. Appl. No. 13/333,882.
USPTO; Non-Final Office Action dated Dec. 31, 2018 in U.S. Appl. No. 16/182,443.
USPTO; Non-Final Office Action dated Apr. 18, 2019 in U.S. Appl. No. 13/333,882.
USPTO; Final Office Action dated May 2, 2019 in U.S. Appl. No. 15/736,284.
USPTO; Final Office Action dated May 2, 2019 in U.S. Appl. No. 16/182,443.
USPTO; Non-Final Office Action dated May 7, 2019 in U.S. Appl. No. 16/008,991.
USPTO; Non-Final Office Action dated May 16, 2019 in U.S. Appl. No. 16/132,247.
USPTO; Non-Final Office Action dated May 24, 2019 in U.S. Appl. No. 16/218,010.
EPO; Extended Search Report dated Dec. 12, 2018 in EP Application No. 16808223.8.
EPO; Extended Search Report dated Dec. 11, 2018 in EP Application No. 16822021.8.
EPO; Extended Search Report dated Jun. 6, 2019 in EP Application No. 17739028.3.
Lee et al., "Lentiviral delivery of short hairpin RNAs protects CD4 cells from multiple clades and primary isolates of HIV." Blood, 2005, vol. 106(3):818-826. (Year: 2005).
Choi et al., "Multiplexing Seven miRNA-Based shRNAs to Suppress HIV Replication." Molecular Therapy, 2015, vol. 23(2):310-320. Supplementary materials.
Spartevello et al., Development of Lentiviral Vectors Simultaneously Expressing Multiple siRNAs Against CCR5, vif and tat/rev Genes for an HIV-1 Gene Therapy Approach, Molecular Therapy—Nucleic Acids, 2016, vol. 5:1-12.
USPTO; Office Action dated Jul. 6, 2020 in the U.S. Appl. No. 16/312,056.
JP; Japanese Office Action in the Application No. 2019-500475 dated Jun. 12, 2020.
Pallikkuth et al., "Human Immunodeficiency Virus (HIV) gag Anti-Specific T-Helper and Granule-Dependent CD8 T-Cell Activities in Exposed but Uninfected Heterosexual Partners of HIV Type 1-Infected Individuals in North India," Clinical and Vaccine Immunology, vol. 14(9) pp. 1196-1202, (2007).
EPO; Extended European Supplementary Search Report dated Feb. 6, 2020 in the Application No. 17825011.4.
EPO; Extended European Supplementary Search Report dated Feb. 6, 2020 in the Application No. 17824652.6.
Bergvall et al. "The E1 proteins", Virology 445; p. 35-56, (Year:2013).
McBride, A., "The Papillomavirus E2 proteins", Virology 445: p. 57-79, (Year: 2013).
Chiang C-m et al., "Viral E1 and E2 proteins support replication of homologous and heterologous papillomaviral origins." PNAS 89: p. 5799-5803, (Year: 1992).
Krajinovic et al., "Sequencing data on the long control region of human papillomavirus type 16." Journal of General Virology 72:2573-2576, (Year: 1991).
Seedorg et al., "Human Papillomavirus type 16 DNA sequence." Virology 145: p. 181-185, (Year: 1985).
Jaalouk, et al. "A Self-inactivating retrovector incorporating the IL-2 promoter for activation-induced transgene expression engineered t-cells," Virology Journal: p. 1-12, (Year: 2006).
USPTO; Notice of Allowance dated Jul. 10, 2020 in the U.S. Appl. No. 16/530,908.
USPTO; Final Office Action dated Jul. 27, 2020 in the U.S. Appl. No. 16/076,655.
JP; Japanese Office Action in the Application No. 2018-536892 dated Jun. 26, 2020.
Brites, C., M. Abrahao, P. Bozza, E. M. Netto, A. Lyra and F. Bahia (2018). "Infectionby HTLV-1 Is Associated with High Levels of Proinflammatory Cytokines in HIV-HCV-Coinfected Patients." J Acquir Immune Defic Syndr 77(2): 230-234.
Douek, D. C., J. M. Brenchley, M. R. Betts, D. R. Ambrozak, B. J. Hill, et al. (2002). "HIV preferentially infects HIV-specific CD4+ T cells." Nature 417(6884): 95-98.
Eguchi, K., N. Matsuoka, H. Ida, M. Nakashima, M. Sakai, et al. (1992). "Primary Sjogren's syndrome with antibodies to HTLV-I: clinical and laboratory features." Ann Rheum Dis 51(6): 769-776.
Futsch, N., R. Mahieux and H. Dutartre (2017). "HTLV-1, the Other Pathogenic Yet Neglected Human Retrovirus: From Transmission to Therapeutic Treatment." Viruses, 10, 1; doi:10.3390/v10010001.
Gessain, A., F. Barin, J. C. Vemant, O. Gout, L. Maurs, A. Calender and G. de The (1985). "Antibodies to human T-lymphotropic vims type-I in patients with tropical spastic paraparesis." Lancet 2(8452): 407-410.
Gessain, A. and O. Cassar (2012). "Epidemiological Aspects and World Distribution of HTLV-1 Infection." Front Microbiol 3: 388.
Goncalves, D. U., F. A. Proietti, J. G. Ribas, M. G. Araujo, S. R. Pinheiro, A. C. Guedes and A. B. Cameiro-Proietti (2010). "Epidemiology, treatment, and prevention of human T-cell leukemia vims type 1-associated diseases." Clin Microbiol Rev 23(3): 577-589.
Kagdi, H., M. A. Demontis, J. C. Ramos and G. P. Taylor (2018). "Switching and loss of cellular cytokine producing capacity characterize in vivo viral infection and malignant transformation in human T-lymphotropic virus type 1 infection." PLoS Pathog 14(2): e1006861.
Kagdi, H. H., M. A. Demontis, P. A. Fields, J. C. Ramos, C. R. Bangham and G. P. Taylor (2017). "Risk stratification of adult T-cell leukemia/lymphoma using immunophenotyping." Cancer Med 6(1): 298-309.
Macnamara, A., A. Rowan, S. Hilburn, U. Kadolsky, H. Fujiwara, et al. (2010). "HLA class I binding of HBZ determines outcome in HTLV-1 infection." PLoS Pathog 6(9): e101117.
Manel, N., F. J. Kim, S. Kinet, N. Taylor, M. Sitbon and J. L. Battini (2003). "The ubiquitous glucose transporter GLUT-1 is a receptor for HTLV." Cell 115(4): 449-459.
Martinez, M. P., J. Al-Saleem and P. L. Green (2019). "Comparative virology of HTLV-1 and HTLV-2." Retrovirology 16(1): 21.
Mochizuki, M., T. Watanabe, K. Yamaguchi, K. Takatsuki, K. Yoshimura, et al. (1992). "HTLV-I uveitis: a distinct clinical entity caused by HTLV-I." Jpn J Cancer Res 83(3): 236-239.
Mosley, A. J., B. Asquith and C. R. Bangham (2005). "Cell-mediated immune response to human T-lymphotropic virus type I." Viral Immunol 18(2): 293-305.
Nagai, M. and M. Osame (2003). "Human T-cell lymphotropic virus type I and neurological diseases." J Neurovirol 9(2): 228-235.
Yamano, Y. and T. Sato (2012). "Clinical pathophysiology of human T-lymphotropic vims-type 1-associated myelopathy/tropical spastic paraparesis." Front Microbiol 3: 389.
Nishioka, K., I. Maruyama, K. Sato, I. Kitajima, Y. Nakajima and M. Osame (1989). "Chronic inflammatory arthropathy associated with HTLV-I." Lancet 1(8635): 441.
Osame, M., K. Usuku, S. Izumo, N. Ijichi, H. Amitani, et al. (1986). "HTLV-I associated myelopathy, a new clinical entity." Lancet 1(8488): 1031-1032.
Poiesz, B. J., F. W. Ruscetti, A. F. Gazdar, P. A. Bunn, J. D. Minna and R. C. Gallo (1980). "Detection and isolation of type C retrovirus

(56) References Cited

OTHER PUBLICATIONS particles from fresh and cultured lymphocytes of a patient with cutaneous T-cell lymphoma." Proc Natl Acad Sci U S A 77(12): 7415-7419.
Poiesz, B. J., F. W. Ruscetti, J. W. Mier, A. M. Woods and R. C. Gallo (1980). "T-cell lines established from human T-lymphocytic neoplasias by direct response to T-cell growth factor." Proc Natl Acad Sci U S A 77(11): 6815-6819.
Roc, L., C. de Mendoza, M. Fernandez-Alonso, G. Reina, V. Soriano and H. N. Spanish (2019). "Rapid subacute myelopathy following kidney transplantation from HTLV-1 donors: role of immunosuppresors and failure of antiretrovirals." Ther Adv Infect Dis 6: 2049936119868028.
Soker, S., S. Takashima, H. Q. Miao, G. Neufeld and M. Klagsbrun (1998). "Neuropilin-1 is expressed by endothelial and tumor cells as an isoform-specific receptor for vascular endothelial growth factor." Cell 92(6): 735-745.
Uchiyama, T., J. Yodoi, K. Sagawa, K. Takatsuki and H. Uchino (1977). "Adult T-cell leukemia: clinical and hematologic features of 16 cases." Blood 50(3): 481-492.
Dickler, H. B., et al. (1973). "Lymphocyte binding of aggregated IgG and surface Ig staining in chronic lymphocytic leukaemia." Clin Exp Immunol 14(1): 97-106.
USPTO; Notice of Allowance dated May 18, 2020 in the U.S. Appl. No. 16/083,384.
USPTO; Non-Final Office Action dated Jun. 1, 2020 in the U.S. Appl. No. 16/530,908.
CN; 1st Office Action in the CN Application No. 20170017712.6 dated May 8, 2020.
EPO; Office Action in the EPO Application No. 16808223.8 dated May 11, 2020.
USPTO; Non-Final Office Action dated Jan. 13, 2020 in the U.S. Appl. No. 15/580,661.
PCT; International Search Report and Written Opinion in the PCT Application No. PCT/US2019/059828 dated Feb. 14, 2020.
Wang et al., "HIV Vaccine Research: The Challenge and the Way Forward," Journal of Immunology Research, vol. 2015, Article ID 503978, 5 pages.
Bourguigon et al., "Processing of blood samples influences PBMC viability and outcome of cell-mediated immune responses in antiretroviral therapy-naïve HIV-1-infected patients," Journal of Immunological Methods, vol. 414, p. 1-10 (2014).
Briz et al., "Validation of Generation 4 Phosphorus-Containing Polycationic Dendrimer for Gene Delivery Against HIV-1," Current Medical Chemistry, vol. 19, p. 5044-5051, (2012).
Anderson et al., "Preintegration HIV-1 Inhibition by a Combination Lentiviral Vector Containing a Chimeric TRIM5a Protein, a CCR5 shRNA, and TAR Decoy," Molecular Therapy, vol. 17, No. 12, p. 2103-2114, Dec. 2009.
JP; Japanese Office Action in the Application No. 2017-567175 dated Jun. 15, 2020.
EPO; Extended European Search Report in the Application No. 18736295.9 dated Aug. 20, 2020.
Oh et al. "Lentiviral Vector Design Using Alternative RNA Export Elements," Retrovirology, vol. 4:38, pp. 1-10, (2007).
PCT; International Preliminary Report on Patentability dated Oct. 8, 2019 in the Application No. PCT/US2018/025733.
PCT; International Search Report and Written Opinion of the International Search Report dated Jul. 22, 2019 in the Application No. PCT/US2019/024410.
USPTO; Notice of Allowance dated Nov. 27, 2019 in the U.S. Appl. No. 13/333,882.
Quan Jun-Jie et al., "Parp3 interacts with FoxM1 to confer glioblastoma cell radio resistance", Tumor Biology, Karger, Basel, CH, vol. 36, No. 11, Jun. 4, 2015 (Jun. 4, 2015), pp. 8617-8624, XP036217799, ISSN: 1010-4283, DOI: 10.1007/S13277-015-3554-4 [retrieved on Jun. 4, 2015] whole document.
Jakobsson J. and Lundberg C.: "Lentiviral 1, 2, 4-10 vectors for use in the central nervous system", Molecular Therapy: The Journal of the American Society of Gene Therapy, Cell Press, US, vol. 13, No. 3, Mar. 1, 2006 (Mar. 1, 2006), pp. 484-493, XP005326761, ISSN: 1525-0016, DOI: 10.1016/J.Ymthe.2005.11.012 the whole document.
Yun Jong Lee et al., "Poly (ADP-ribose) in 1-15 the pathogenesis of Parkinson's disease", BMB Reports, vol. 47, No. 8, Aug. 31, 2014 (Aug. 31, 2014), pp. 424-432, XP55671927, KR, ISSN: 1976-6696, DOI: 10.5483/BMBRep.2014.47.8.119 the whole document.
Lang Yoo et Al., "Parp-1 regulates the expression of caspase-11", Biochemical and Biophysical Research Communications, vol. 408, No. 3, Apr. 22, 2011 (Apr. 22, 2011), pp. 489-493, XP028209824, ISSN: 0006-291X, DOI: 10.1016/J. BBRC.2011.04.070 [retrieved on Apr. 22, 2011] whole document.
Tae-In Kam et al., "Poly (ADP-ribose) derived pathologic [alpha]—synuclein neurodegeneration in Parkinson's disease", Science, vol. 362, No. 6414, Nov. 1, 2018 (Nov. 1, 2018), p. eaat8407, XP55672116, US, ISSN: 00368075, DOI: 10.1126/science. aat8407 whole document.
Olsen A.L. and Feany M.B., "PARP Inhibitors and Parkinson's Disease", Jan. 1, 2019 (Jan. 1, 2019), XP55672111, retrieved from the Internet: URL: https://mfprac.com/web2019/07literature/literature/Neurology/ParkinsonPARPI_Olsen.pdf [retrieved on Feb. 27, 2020] the whole document.
Richard Lu et al., "Siman Virus 40-Based Replication of Catalytically Inactive Human Immunodeficiency Virus Type 1 Integrase Mutants in Nonpermissive T Cells and Monocyte-Derived Macrophages", Journal of Virology, Jan. 2004, p. 658-668. DOI: 10.1128/JVI.78.2658-668.2004.
FM Sverdrup et al., "Development of human papillomavirus plasmids capable of episomal replication in human cell lines", Gene Therapy, Mar. 26, 1999, p. 1317-1321, Retrieved from the Internet: URL: http://www.stockton-pressco.uk/gt.
Kathleen Van Craenenbroeck et al., "Episomal vectors for gene expression in mammalian cells", Eur J. Biochem, vol. 267, p. 5665-5678, Jul. 14, 2000.
USPTO; Non-Final Office Action dated Mar. 16, 2020 in the U.S. Appl. No. 16/083,384.
EPO; Extended European Supplemental Search Report dated Mar. 11, 2020 in the Application No. 17831904.2.
JP; Japanese Office Action in the Application No. 2017-564550 dated Mar. 18, 2020.
Hassan et al., "Isolation of umbilical cord mesenchymal stem cells using human blood derivative accompanied with explant method," Stem Cell Investigation, pp. 1-8, (2019).
Huang et al., "An Efficient protocol to generate placental chorionic plate-derived mesenchymal stem cells with superior proliferative and immunomodulatory properties," Stem Cell Research & Therapy, pp. 1-15, (2019).
USPTO; Restriction Requirement dated Oct. 22, 2019 in the U.S. Appl. No. 15/580,661.
USPTO; Restriction Requirement dated Nov. 4, 2019 in the U.S. Appl. No. 16/076,655.
USPTO; Notice of Allowance dated Oct. 29, 2019 in the U.S. Appl. No. 13/333,882.
USPTO; Restriction Requirement dated Nov. 7, 2019 in the U.S. Appl. No. 16/083,384.
USPTO; Restriction Requirement dated Jan. 29, 2020 in the U.S. Appl. No. 16/312,056.
EPO; Supplementary European Search Report dated Dec. 19, 2019 in the Application No. 16904834.5.
EPO; Supplementary European Search Report dated Dec. 19, 2019 in the Application No. 17810976.5.
USPTO; Restriction Requirement dated Nov. 19, 2020 in the U.S. Appl. No. 16/593,882.
USPTO; Non-Final Office Action dated Nov. 25, 2020 in the U.S. Appl. No. 16/943,800.
USPTO; Notice of Allowance dated Dec. 2, 2020 in the U.S. Appl. No. 16/076,655.
USPTO; Restriction Requirement dated Dec. 8, 2020 in the U.S. Appl. No. 16/563,738.
USPTO; Notice of Allowance dated Jan. 26, 2021 in the U.S. Appl. No. 16/593,882.
Nada et al., "Enhancing adoptive cancer immunotherapy with Vγ2Vδ2 T cells through pulse zoledronate stimulation", Journal for

(56) References Cited

OTHER PUBLICATIONS

Immunotherapy of Cancer, vol. 5, No. 1, (Feb. 21, 2017), pp. 1-23, (2017) DOI 10.1186/s40425-017-0209-6 the whole document.
Benyamine et al., "BTN3A molecules considerably improve Vγ9Vδ T cells-based immunotherapy in acute myeloid leukemia," Oncolmmunology, vol. 5, No. 10, 10 pages, (Oct. 2, 2016), E1146843 the whole document.
Harly et al., "Key implication of CD277/butyrophilin-3 (BTN3 A) in cellular stress sensing by a major human γδ T-cell subset," American Society of Hematology , vol. 120, No. 11, (Sep. 13, 2012), pp. 2269-2279, XP055081172, ISSN: 0006-4971, DOI: 10.1182/blood-2012-05-430470 the whole document.
Wang et al., "Intravenous Delivery of SiRNA Targeting CD47 Effectively Inhibits Melanoma Tumor Growth and Lung Metastasis", Molecular Therapy, pp. 1919-1929, vol. 21, No. 10, Oct. 2013.
Mandir, A. S., et al., "Poly (ADP-ribose) polymerase activation mediates 1-methyl-4-phenyl-1, 2,3,6-tetrahydropyridine (MPTP)-induced parkinsonism", Proc Natl Acad Sci U S A, 96: 5774-9, 1999.
USPTO; Notice of Allowance dated Feb. 10, 2021 in the U.S. Appl. No. 16/943,800.
USPTO; Non-Final Office Action dated Feb. 19, 2021 in the U.S. Appl. No. 15/580,661.
USPTO; Final Office Action dated Feb. 26, 2021 in the U.S. Appl. No. 16/312,056.
USPTO; Corrected Notice of Allowance dated Mar. 3, 2021 in the U.S. Appl. No. 16/687,525.
USPTO; Non-Final Office Action dated Mar. 12, 2021 in the U.S. Appl. No. 16/563,738.
CN; 1st Office Action in the CN Application No. 202010396594.8 dated Jan. 15, 2021.
EP; Supplementary Search Report in the EP Application No. 18817253 dated Feb. 10, 2021.
JP; Office Action in the JP Application No. 2018-547354 dated Feb. 16, 2021.
JP; Office Action in the JP Application No. 2018-541270 dated Jan. 8, 2021.
Zhaobing Ding et al., "Liver -Directed, AAV-and Lentivirus-Mediated Gene Therapy in the Phenylketonuria Mouse Model Pah-enu2", Molecular Therapy, vol. 11, Supp. 1. (May 2005) XP055751452.
Ledley et al., "Retroviral-mediated gene transfer of human phenylalanine hydroxylase into NIH 3T3 and hepatoma cells", Proceedings of the National Academy of Sciences, vol. 83, No. 2. (Jan. 1, 1986), pp. 409-413, XP002583115.
Ledley et al., "Molecular biology of phenylalanine hydroxylase and phenylketonurina", Trends in Genetics, Elsevier Science Publishers B.V. Amsterdam, NL, vol. 1. (Jan. 1, 1985), pp. 309-313, XP025943064.
USPTO; Notice of Allowance dated Jan. 13, 2021 in the U.S. Appl. No. 16/687,525.
EP; Supplementary Search Report in the EP Application No. 18781288.8 dated Dec. 8, 2020.
JP; Final Office Action in the JP Application No. 2018-536892 dated Nov. 16, 2020.
USPTO; Non-Final Office Action dated Oct. 29, 2020 in the U.S. Appl. No. 15/736,284.
JP; Japanese Office Action in the JP Application No. 2018-563892 dated Oct. 14, 2020.
Hellstrom et al., "Cellular tropism and transduction properties of seven adeno-associated viral vector serotypes in adult retina after intravitreal injection", Gene Therapy, 2009, 16: 521-532.
Erdelyi, K. et al., Dual role of poly(ADP-ribose) glycohydrolase in the regulation of cell death in oxidatively stressed A549 cells, FASEB J., 2009, vol. 23(10), pp. 3553-3563.
Nie, J., DNA repair proteins Metnase and PARP1 regulate DNA integration, 2000-2019—CSU Theses and Dissertations [online], 2015, Chapter 3, pp. 95-141, URL: http://hdl.handle.net/10217/166898.
Liu, F. et al., Effects of poly (ADP-ribose) polymerase-1 (PARP-1) inhibition on sulfur mustard-induced cutaneous injuries in vitro and in vivo, Peer J., 2016, vol. 4: e1890, pp. 1-28.
Martin, K. A., Global Transcriptome Analysis Reveals That Poly(ADP-Ribose) Polymerase 1 Regulates Gene Expression through EZH2, Mol. Cell Biol., 2015, vol. 35 (23), pp. 3934-3944.
USPTO; Final Office Action dated Jun. 3, 2021 in the U.S. Appl. No. 16/318,345.
JP; Office Action in the JP Application No. 2019-502170 dated May 28, 2021.
JP Office Action in Japanese Application No. 2019-502170, dated Mar. 28, 2022, 9 pages (with English translation).

* cited by examiner

AGT Helper plus Rev plasmid

AGT Envelope plasmid

Lentiviral vector expressing PARP1 shRNA and GFP

AGT Helper plus Rev plasmid

AGT Envelope plasmid

Lentiviral vector expressing PARP1 shRNA

VIRAL VECTORS FOR TREATING PARKINSON'S DISEASE

CROSS-REFERENCE TO RELATED APPLICATIONS

This application is a U.S. national phase filing under 35 U.S.C. § 371 of PCT/US2017/043157 filed on Jul. 20, 2017, entitled "VIRAL VECTORS FOR TREATING PARKINSON'S DISEASE," which claims priority to U.S. Provisional Patent Application No. 62/365,316 filed on Jul. 21, 2016 entitled "VIRAL VECTORS FOR TREATING PARKINSON'S DISEASE," the disclosures of which are incorporated herein by reference.

FIELD

Aspects of the invention relate to using vectors to treat Parkinson's disease. More specifically, aspects of the invention relate to using lentiviral vectors, including PARP-containing lentiviral vectors, to treat Parkinson's disease.

BACKGROUND

Parkinson's disease ("PD") is the second most common neurodegenerative disorder in the United States. Approximately 1 million Americans are afflicted with PD, with more than 60,000 new cases diagnosed each year. See, e.g., Fahn, S., 991 *Ann. N.Y. Acad. Sci.* 1-14 (2003). The incidence is expected to double by 2030. See, e.g., Dorsey, E. R., et al., 68(5) *Neurology,* 384-6 (2007). PD is a chronic progressive condition that generally appears late in life. PD is caused by the degeneration and death of dopamine producing neurons in the substantia nigra region of the basal ganglia. The deteriorated neurons and reduced dopamine result in abnormal neural activity and a chronic, progressive deterioration of motor function control. Patients with PD suffer from significant quality-of-life issues due to symptoms that include bradykinesia, rigidity, tremor, and postural instability. Additional complications due to PD include non-motor symptoms, such as dysphagia, and neuropsychiatric effects. See, e.g., Weintraub, D. et al., 14(2 Suppl) *Am. J. Manag. Care, S*40-8 (2008).

PD can be treated with L-DOPA or dopamine agonists, but there are significant side effects and the continuous neuronal death results in an increasing requirement for L-DOPA or dopamine agonists. Gene therapy has the potential to modify the behavior of neurons in the substantia nigra. Consequently, gene therapy has been considered as a possibility for effectively treating PD.

Initial clinical studies on PD gene therapy attempted to increase dopamine production in the substantia nigra by elevating the level of dopamine-synthesizing enzymes, particularly aromatic L-amino acid decarboxylase (AADC). Adeno-associated viral vectors (AAV) carrying the complementary DNA sequence for AADC were injected into the substantia nigra of patients afflicted with PD. In one study, delivery of AADC using adeno-associated virus (AAV) was well tolerated, but the clinical outcomes trended to only modest improvement. See, e.g., Eberling et al., 70(21) *Neurology,* 1989-93 (2008). After longer (e.g., 4-year) follow-up, the clinical impact was largely lost, and it was concluded that the dosing was insufficient for sustained clinical improvement An alternate approach sought to treat PD using gene therapy to increase expression of neurturin, a neurotrophic growth factor, in the substantia nigra. Results from AAV delivery of the neurturin gene to the brains of patients afflicted with PD showed no improvement over sham controls. See, e.g., Marks Jr. et al., 9(12) *Lancet Neural.,* 164-72 (2010).

Gene therapy trials designed to increase dopamine production or provide neurotrophic growth factors have not provided a significant, durable objective clinical response in patients with PD. See, e.g., Eberling et al., supra. Part' of the reason why treatment for PD is complex and challenging is that disease progression is due to the accelerated death of dopaminergic neurons that eventually reduces dopamine below survivable levels.

Accordingly, current treatments for PD symptoms include drugs, ablative surgical intervention, and neural stimulation.

SUMMARY

In an aspect of the present disclosure, a lentiviral vector system is provided for expressing a lentiviral particle. The system includes a therapeutic vector which encodes a short hairpin RNA ("shRNA") for inhibiting Poly(ADP-ribose) polymerase ("PARP") expression. The system also includes an envelope plasmid comprising a neuron-specific sequence for targeting the shRNA to a neuron; and at least one helper plasmid comprising gag, pot, and rev genes. When the therapeutic vector, the envelope plasmid, and the at least one helper plasmid are transfected into a packaging cell line, a neuron-specific lentiviral particle optimized for inhibiting PARP expression is produced by the packaging cell line.

In embodiments, the shRNA comprises a PARP-specific shRNA. In embodiments, the shRNA comprises a PARP1-specific shRNA. In embodiments, the shRNA comprises at least 80% sequence identity with any one of SEQ ID NOs: 6-10. In embodiments, the shRNA comprises a shRNA having at least 85% sequence identity with any one of SEQ ID NOs: 6-10. In embodiments, the shRNA comprises a shRNA having at least 90% sequence identity with any one of SEQ ID NOs; 6-10. In embodiments, the shRNA comprises a shRNA having at least 95% sequence identity with any one of SEQ ID NOs: 6-10. In embodiments, the shRNA comprises any one of SEQ ID NOs: 6-10.

In embodiments, the shRNA comprises a shRNA having at least 80% sequence identity with any one of SEQ ID NOs: 16-20. In embodiments, the shRNA comprises a shRNA having at least 85% sequence identity with any one of SEQ ID NOs: 16-20, In embodiments, the shRNA comprises a shRNA having at least 90% sequence identity with any one of SEQ ID NOs: 16-20. In embodiments, the shRNA comprises a shRNA having at Least 95% sequence identity with any one of SEQ ID NOs: 16-20. In embodiments, the shRNA comprises any one of SEQ ID NOs: 16-20, In embodiments, the neuron-specific sequence encodes VSV-G, FUG-C, or gp64, or a variant thereof. Optionally, the neuron-specific sequence encodes only VSV-G, or a variant thereof. The neuron-specific sequence may encode a protein that improves transduction into a neuron. The neuron-specific sequence may encode a protein that improves transduction into a neuron expressing tyrosine hydroxylase (TH+).

In another aspect, a method of treating a subject suffering from Parkinson's disease is disclosed. The method involves administering to the subject a therapeutic vector comprising a shRNA for inhibiting PARP expression: an envelope plasmid comprising a neuron-specific sequence for targeting the shRNA to a neuron; and at least one helper plasmid comprising gag, pol, and rev genes. When the therapeutic vector, the envelope plasmid, and the at least one helper plasmid are transfected into at least one packaging cell, a neuron-specific lentiviral particle optimized for inhibiting PARP expression is produced by the packaging cell, and lentiviral particle is administered to the subject in need thereof. In embodiments, the lentiviral particle transduces a host cell to deliver the PARP shRNA. In embodiments, the shRNA comprises a PARP-specific shRNA. In embodiments, the shRNA comprises a PARP1-specific shRNA. In embodiments, the shRNA comprises a shRNA having at least 80% sequence identity with any one of SEQ ID NOs: 6-10. In embodiments, the shRNA comprises a shRNA having at least 85% sequence identity with any one of SEQ ID NOs: 6-10. In embodiments, the shRNA comprises a shRNA having at least 90% sequence identity with any one of SEQ ID NOs: 6-10. In embodiments, the shRNA comprises a shRNA having at least 95% sequence identity with any one of SEQ ID NOs: 6-10. In embodiments, the shRNA comprises any one of SEQ ID NOs: 6-10. In embodiments, the shRNA comprises a shRNA having at least 80% sequence identity with any one of SEQ ID NOs: 16-20. In embodiments, the shRNA comprises a shRNA having at least 85% sequence identity with any one of SEQ ID NOs: 16-20. In embodiments, the shRNA comprises a shRNA having at least 90% sequence identity with any one of SEQ ID NOs: 16-20. In embodiments, the shRNA comprises a shRNA having at least 95% sequence identity with any one of SEQ ID NOs: 16-20. In embodiments, the shRNA comprises any one of SEQ ID NOs: 16-20. The neuron-specific sequence may encode VSV-G, FUG-C, or gp64, or variants thereof. The neuron-specific sequence may encode only VSV-G, or variants thereof. The neuron-specific sequence may encode a protein that improves transduction into a neuron of the subject. The neuron-specific sequence may encode a protein that improves transduction into a neuron expressing tyrosing hydroxylase (TH+) of the subject.

In another aspect, a method of treating a subject suffering from Parkinson's disease is disclosed. The method involves administering to the subject a therapeutically effective amount of a lentiviral particle expressed by the lentiviral vector system as described herein. The method may also include a second therapeutic regimen. The second therapeutic regimen may include ablative surgical intervention, neural stimulation, L-DOPA administration, or dopamine agonist administration.

In another aspect, use of a therapeutic vector, an envelope plasmid, and at least one helper plasmid is disclosed for treating a subject suffering from Parkinson's disease. The therapeutic vector includes a shRNA to inhibit PARP expression. The envelope plasmid includes a neuron-specific sequence to target the shRNA to a neuron. One or more helper plasmids include at least one or more of a gag, pol, or rev gene.

By suppressing PARP levels, the lentiviral vector system disclosed herein reduces rates for neuronal death, preserves the capacity for normal dopamine production and delay or prevent the onset of Parkinson's disease. The lentiviral vector system disclosed herein, unlike AAVs, has a higher capacity for transducing resting cells, can be optimized to efficiently transduce neurons, and can generate a permanent modification by inserting a transgene into cellular DNA. Additionally, the lentiviral vector system disclosed herein is less inflammatory than AAVs, which allows for greater dose escalation, and allows for greater flexibility in vector design when testing for alternate envelope glycoproteins, vector composition, doses, and associated delivery methods.

Other aspects and advantages of the inventions described herein will become apparent from the following detailed description, taken in conjunction with the accompanying drawings, which illustrate by way of example the aspects of the inventions.

DETAILED DESCRIPTION

Overview of the Disclosure

Figure 1A:
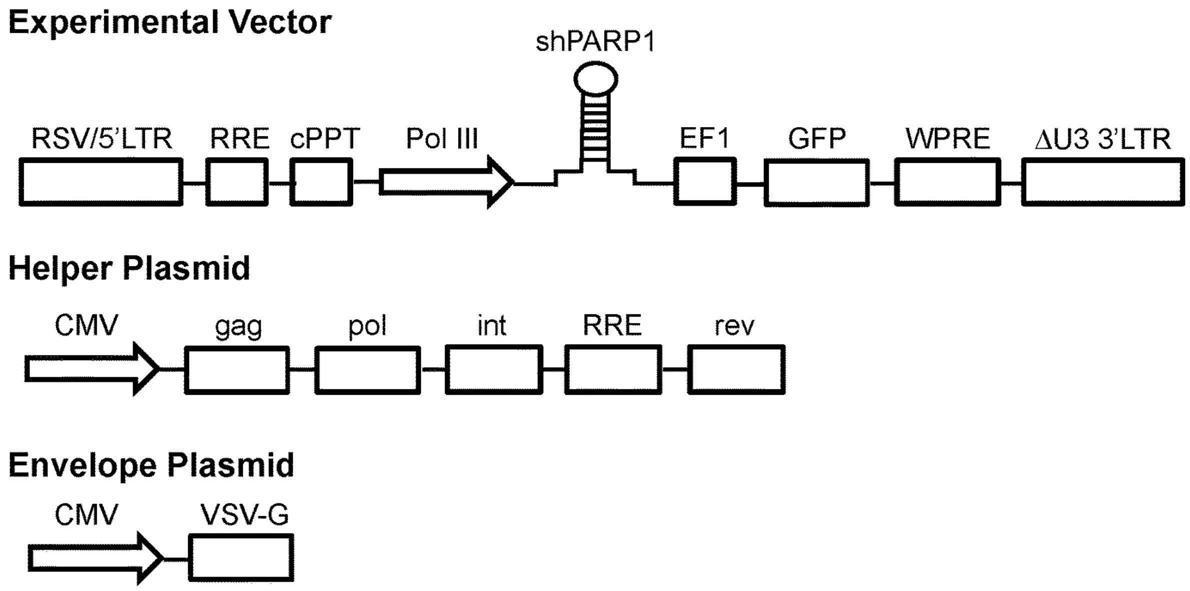
FIG. 1A depicts an exemplary lentiviral vector system comprised of an experimental therapeutic vector, an envelope plasmid, and a helper plasmid. The experimental therapeutic vector detailed in FIG. 1A contains GFP.
Figure 1B:
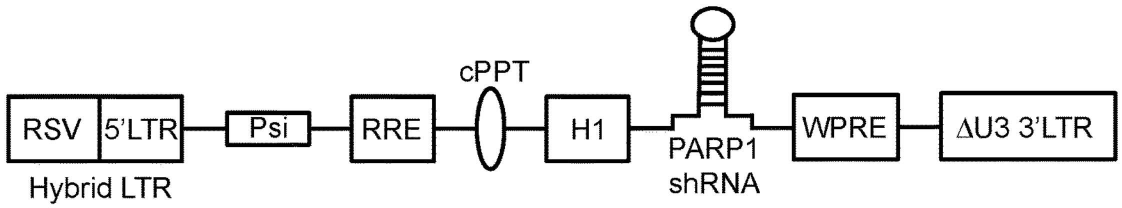
FIG. 1B depicts an exemplary therapeutic vector designed to reduce expression of PARP1 in substantia nigra neurons in patients afflicted with PD. The therapeutic vector detailed in FIG. 1B does not contain CFR

Aspects of the present invention describe the development of a lentiviral vector system for treating PD. The lentiviral vector system includes a therapeutic vector that includes an inhibitory RNA construct for reducing the expression of PARP. The PARD1 protein has been implicated for its role in PD.

Definitions and Interpretation

Unless otherwise defined herein, scientific and technical terms used in connection with the present disclosure shall have the meanings that are commonly understood by those of ordinary skill in the art. Further, unless otherwise required by context, singular terms shall include pluralities and plural terms shall include the singular. Generally, nomenclature used in connection with, and techniques of, cell and tissue culture, molecular biology, immunology, microbiology, genetics and protein and nucleic acid chemistry and hybridization described herein are those well-known and commonly used in the art. The methods and techniques of the present disclosure are generally performed according to conventional methods well-known in the art and as described in various general and more specific references that are cited and discussed throughout the present specification unless otherwise indicated. See, e.g.; Sambrook J. & Russell D, Molecular Cloning: A Laboratory Manual, 3rd ed., Cold Spring Harbor Laboratory Press, Cold Spring Harbor, N.Y. (2000); Ausubel et al., Short Protocols in Molecular Biology: A Compendium of Methods from Current Protocols in Molecular Biology, Wiley, john & Sons, Inc. (2002); Harlow and Lane Using Antibodies: A Laboratory Manual; Cold Spring Harbor Laboratory Press, Cold Spring Harbor, N.Y. (1998); and Coligati et al., Short Protocols in Protein Science, Wiley, John & Sons, Inc. (2003). Any enzymatic reactions or purification techniques are performed according to manufacturer's specifications, as commonly accomplished in the art or as described herein. The nomenclature used in connection with, and the laboratory procedures and techniques of, analytical chemistry, synthetic organic chemistry, and medicinal and pharmaceutical chemistry described herein are those well-known and commonly used in the art.

As used herein, the term "includes" means includes without limitation.

As used herein, the term "lentiviral vector" is synonymous with the term "therapeutic vector." The term "experimental therapeutic vector" means a therapeutic vector that includes an experimental feature such as OPP.

As used herein, the term "mi RN A" means a microRNA.

As used herein, the term "packaging cell line" refers to any cell line that can be used to express a lentiviral particle.

As used herein, the term "Parkinson's disease," which is also referred to herein as "PD," refers to the known neurodegenerative disease, as well as all symptoms related thereto. Treatment of "Parkinson's disease," therefore, may relate to treatment of all or some of the symptoms associated with Parkinson's disease.

As used herein, the term "PARP" stands for poly ADP ribose polymerase and includes all PARP-family members, and includes the specific PARP-family member, PARP1 (accession number NM_001618.3) and variants thereof.

The term "percent identity," which is also referred to herein as "sequence identity," in the context of two or more nucleic acid or polypeptide sequences, refer to two or more sequences or subsequences that have a specified percentage of nucleotides or amino acid residues that are the same, when compared and aligned for maximum correspondence, as measured using one of the sequence comparison algorithms described below (e.g., BLASTP and BLASTN or other algorithms available to persons of skill) or by visual inspection. Depending on the application, the "percent identity" can exist over a region of the sequence being compared, e.g., over a functional domain, or, alternatively, exist over the full length of the two sequences to be compared. For sequence comparison, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Natl. Sci. USA.* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., infra).

One example of an algorithm that is suitable for determining percent sequence identity and sequence similarity is the BLAST algorithm, which is described in Altschul et al., *J. Mol. Biol.* 215:403-410 (1990). Software for performing BLAST analyses is publicly available through the National Center for Biotechnology Information website.

The percent identity between two nucleotide sequences can be determined using the GAP program in the GCG software package (available at www.gcg.com), using a. NWSgapdna.CMP matrix and a gap weight of 40, 50, 60, 70, or 80 and a length weight of 1, 2, 3, 4, 5, or 6. The percent identity between two nucleotide or amino acid sequences can also be determined using the algorithm of E. Meyers and W. Miller (*CABIOS,* 4:11-17 (1989)) which has been incorporated into the ALIGN program (Version 2.0), using a PAM120 weight residue table, a gap length penalty of 1.2 and a gap penalty of 4. In addition, the percent identity between two amino acid sequences can be determined using the Needleman and Wunsch (*J. Mol. Biol.* (48):444-453 (1970)) algorithm which has been incorporated into the GAP program in the GCG software package (available at www.gcg.com), using either a Blossum 62 matrix or a PAM250 matrix, and a gap weight of 16, 14, 12, 10, 8, 6, or 4 and a length weight of 2, 3, 4, 5, or 6.

The nucleic acid and/or protein sequences of the present disclosure can further be used as a "query sequence" to perform a search against public databases to, for example, identify, related sequences. Such searches can be performed using the NBLAST and XBLAST programs (version 2.0) of Altschul et al. (1990) *J. Mol. Biol.* 215:403-10. BLAST nucleotide searches can be performed with the NBLAST program, score=100, word length=12 to obtain nucleotide sequences homologous to the nucleic acid molecules provided in the disclosure. BLAST protein searches can be performed with the XBLAST program, score=50, wordlength=3 to obtain amino acid sequences homologous to the protein molecules of the disclosure. To obtain gapped alignments for comparison purposes. Gapped BLAST can 1.0 be utilized as described in Altschul et at, (1997) *Nucleic Acids Res.* 25(17):3389-3402.

When utilizing BLAST and Gapped BLAST programs, the default parameters of the respective programs (e.g., XBLAST and NBLAST) can be used. See www.ncbi.nim.nih.gov.

As used herein, the term "plasmid" is synonymous with the term "vector."

As used herein, the term "SEQ ID NO" is synonymous with the term "Sequence ID No."

As used herein, the term "shRNA" refers to a short hairpin RNA.

As used herein, the term "subject" includes a human patient but also includes other mammals.

As used herein, the term "TH" refers to tyrosine hydroxylase.

DESCRIPTION OF ASPECTS OF THE DISCLOSURE

In an aspect of the disclosure, the present disclosure provides a lentiviral vector system for expressing a lenti viral particle. The system includes a therapeutic vector which includes a shRNA for inhibiting PARP-family member expression. There are numerous PARP family members and this disclosure is not limited to any one particular PARP-family member. However, in embodiments, the lentiviral vector system specifically inhibits PARP1.

The system includes at least one helper plasmid comprising at least one of a gag, pot, or rev gene, Each of the gag, pol and rev genes may be provided on individual plasmids, or one or more genes may be provided together on the same plasmid. In embodiments, the gag, poi, and rev genes are provided on the same plasmid (e.g., FIG. 1C). In embodiments, the gag and pol genes are provided on a first plasmid and the rev gene is provided on a second plasmid (e.g., FIG. 1D). In further embodiments, 3-vector and 4-vector systems are provided herein.

As detailed herein, the therapeutic vector, the envelope plasmid and at least one helper plasmid are transfected into a packaging cell line. A non-limiting example of a packaging cell line is the 293T/17 HEK cell line. When the therapeutic vector, the envelope plasmid, and at least one helper plasmid are transfected into the packaging cell line, a lentiviral particle is produced. Under the experimental conditions described herein, the lentiviral particle produced by the lentiviral vector system can be a neuron-specific lentiviral particle which is optimized for inhibiting PARP expression.

In embodiments, the shRNA comprises a PARP-specific shRNA. In embodiments, the shRNA comprises a PARP1-specific shRNA. In embodiments, the shRNA comprises a shRNA having at least 80%, or at least 81%, or at least 82%, or at least 83%, or at least 84% sequence identity with any one of SEQ ID NOs: 6-10. In embodiments, the shRNA comprises a shRNA having at least 85%, or at least 86%, or at least 87%, or at least 88%, or at least 89% sequence identity with any one of SEQ ID NOs: 6-10. In embodiments, the shRNA comprises a shRNA having at least 90%, or at least 91%, or at least 92%, or at least 93%, or at least 94% sequence identity with any one of SEQ ID NOs: 6-10. In embodiments, the shRNA comprises a shRNA having at least 95%, or at least 96%, or at least 97%, or at least 98%, or at least 99% with any one of SEQ ID NOs: 6-10. In embodiments, the shRNA comprises any one of SEQ ID NOs: 6-10.

In embodiments, the shRNA comprises a shRNA having at least 80%, or at least 81%, or at least 82%, or at least 83%, or at least 84% sequence identity with any one of SEQ ID NOs: 16-20. In embodiments, the shRNA comprises a shRNA having at least 85%, or at least 86%, or at least 87%, or at least 88%, or at least 89% sequence identity with any one of SEQ ID NOs: 16-20. In embodiments, the shRNA comprises a shRNA having at least 90%, or at least 91%, or at least 92%, or at least 93%, or at least 94% sequence identity with any one of SEQ ID NOs: 16-20. In embodiments, the shRNA comprises a shRNA having at least 95%, or at least 96%, or at least 97%, or at least 98%, or at least 99% sequence identity with any one of SEQ ID NOs: 16-20. In embodiments, the shRNA comprises any one of SEQ ID NOs: 16-20. In embodiments, any of the foregoing shRNAs can be replaced with a suitable miRNA. In embodiments, the neuron-specific sequence encodes VSV-G, gp64 or any other sequence that confers tropic specificity to neuron cells. Optionally, the neuron-specific sequence encodes only VSV-G. In embodiments, the neuron-specific sequence encodes a protein that improves transduction into a neuron. In embodiments, the neuron-specific sequence encodes a protein that improves transduction into a TH+ neuron.

In another aspect of the disclosure, a method of treating a subject suffering from PD is disclosed. In embodiments, the subject is a human being afflicted with mild, moderate, or severe PD. In embodiments, the subject is a human being afflicted with any symptom commonly or uncommonly associated with PD.

The method involves administering to the subject a lentiviral therapeutic vector comprising a shRNA for inhibiting PARP expression. In embodiments, the lentiviral vector is packaged as a lentiviral panicle that transduces a host cell to deliver the PARP shRNA.

In embodiments, the shRNA comprises a PARP-specific shRNA. In embodiments, the shRNA comprises a PARP1-specific snRNA. In embodiments, the shRNA comprises a shRNA having at least 80%, or at least 81%, or at least 82%, or at least 83%, or at least 84% sequence identity with any one of SEQ ID NOs: 6-10. In embodiments, the shRNA comprises a shRNA having at least 85%, or at least 86%, or at least 87%, or at least 88%, or at least 89% sequence identity with any one of SEQ ID NOs: 6-10. In embodiments, the shRNA comprises a shRNA having at least 90%, or at least 91%, or at least 92%, or at least 93%, or at least 94% sequence identity with any one of SEQ ID NOs: 6-10. In embodiments, the shRNA comprises a shRNA having at least 95%, or at least 96%, or at least 97%, or at least 98%, or at least 99% sequence identity with any one of SEQ ID NOs: 6-10. In embodiments, the shRNA comprises any one of SEQ ID NOs: 6-10.

In embodiments, the shRNA comprises a shRNA having at least 80%, or at: least 81%, or at least 82%, or at least 83%, or at least 84% sequence identity with any one of SEQ ID NOs: 16-20. In embodiments, the shRNA comprises a shRNA having at least 85%, or at least 86%, or at least 87%, or at least 88%, or at least 89% sequence identity with any one of SEQ ID NOs: 16-20. In embodiments, the shRNA comprises a shRNA having at least 90%, or at least 91%, or at least 92%, or at least 93%, or at least 94% sequence identity with any one of SEQ ID NOs: 16-20. In embodiments, the shRNA comprises a shRNA having at least 95%, or at least 96%, or at least 97%, or at least 98%, or at least 99% sequence identity with any one of SEQ ID NOs: 16-20. In embodiments, the shRNA comprises any one of SEQ ID NOs: 16-20. In embodiments, any of the foregoing shRNAs can be replaced with a suitable miRNA. In embodiments, the neuron-specific sequence encodes VSV-G, FUG-C, or gp64 or any other sequence that confers tropic specificity to neuron cells. Optionally, the neuron-specific sequence encodes only VSV-G. In embodiments, the neuron-specific sequence encodes a protein that improves transduction into a neuron of the subject. In embodiments, the neuron-specific sequence encodes a protein that improves transduction into a TH+ neuron of the subject.

In another aspect, a method of treating a subject suffering from PD is disclosed. The method involves administering to the subject a therapeutically effective amount of a lentiviral particle expressed by the lentiviral vector system as described herein. In embodiments, the method includes a second therapeutic regimen. In embodiments, the second therapeutic regimen includes, but is not limited to: ablative surgical intervention, neural stimulation. L-DOPA administration, dopamine agonist administration, or any other known Parkinson's disease treatment. In embodiments, the system disclosed herein can be used to treat PD while eliminating the need for increasing doses of L-DOPA.

Lentiviral Vector System

A lentiviral virion (particle) is expressed by a vector system encoding the necessary viral proteins to produce a virion (viral particle), There is at least one vector containing a nucleic acid sequence encoding the lentiviral pol proteins necessary for reverse transcription and integration, operably linked to a promoter. In another embodiment, the poi proteins are expressed by multiple vectors.

In another aspect, use of a therapeutic vector, an envelope plasmid, and at least one helper plasmid is disclosed for treating a subject suffering from PD. The therapeutic vector includes a shRNA to inhibit PARP expression. In embodiments, the envelope plasmid includes a neuron-specific sequence to target the shRNA to a neuron and at least one helper plasmid that includes gag, pol, and rev genes.

By suppressing PARP levels, the lentiviral vector system disclosed herein will reduce rates for neuronal death, preserve the capacity for normal dopamine production and delay and/or prevent the onset of PD. The lentiviral vector system disclosed herein, unlike AAV systems known in the art, has a higher capacity for transducing resting cells, can be optimized to efficiently transduce neurons, and can generate a permanent modification by inserting a transgene into cellular DNA. Additionally, the lentiviral vector system disclosed herein is less inflammatory than AAV systems, which allows for greater dose escalation, and allows for greater flexibility in vector design when testing for alternate envelope glycoproteins, vector composition, doses and associated delivery methods.

The disclosed lentiviral vector system can be optimized for short, medium, or long-term suppression of PARP expression in subjects afflicted with PD. Accordingly, dosing regimens may vary based upon the severity of the PD, or the associated PD symptoms. The lentiviral particles disclosed herein may be administered to a subject in need thereof in varying doses. A subject may be administered $\geq 10^6$ transducing units of lentiviral particle suspension (where 1 dose is needed on average to transduce 1 target cell). A subject may be administered $\geq 10^6$, $\geq 10^7$, $\geq 10^8$, $\geq 10^9$, or $\geq 10^{10}$ transducing units. Upper dosing limits will be determined by a variety of factors understood by those persons skilled in the art.

The vector(s) forming the lentiviral particle preferably do not contain a nucleic acid sequence from the lentiviral genome that expresses an envelope protein. Preferably, a separate vector that contains a nucleic acid sequence encoding an envelope protein operably linked to a promoter is used. This env vector also does not contain a lentiviral packaging sequence. In one embodiment, the env nucleic acid sequence encodes a lentiviral envelope protein.

In another embodiment, the envelope protein is not from the lentivirus, but from a different virus. The resultant particle is referred to as a pseudotyped particle. By appropriate selection of envelopes one can "infect" virtually any cell. For example, one can use an env gene that encodes an envelope protein that targets an endocytic compartment such as that: of the influenza virus, VSV-G, alpha viruses (Semliki forest virus, Sindbis virus), arenaviruses (lymphocytic choriomeningitis virus), flaviviruses (tick-borne encephalitis virus, Dengue virus, hepatitis C virus. GB virus), rhabdoviruses (vesicular stomatitis virus, rabies virus), paramyxoviruses (mumps or measles). picornaviruses (Mengo, Polio, and Coxsackie), and orthomyxoviruses (influenza virus). Other envelopes that can preferably be used include those from Moloney Leukemia Virus such as MLV-E, MLV-A and GAIN. These latter envelopes are particularly preferred where the host cell is a primary cell. Other envelope proteins can be selected depending upon the desired host cell. For example, targeting specific receptors such as a dopamine receptor can be used for brain delivery. Another target can be vascular endothelium. These cells can be targeted using a Filovirus envelope. For example, the GP of Ebola, which by post-transcriptional modification become the GP, and $GP_2$ glycoproteins. In another embodiment, one can use different lentiviral capsids with a pseudotyped envelope (for example, FIV or SHIV [U.S. Pat. No. 5,654,195]). A SHIV pseudotyped vector can readily be used in animal models such as monkeys.

As detailed herein, a lentiviral vector system typically includes at least one helper plasmid comprising at least one of a gag, pot, or rev gene. Each of the gag, pol and rev genes may be provided on individual plasmids, or one or more genes may be provided together on the same plasmid. In one embodiment, the gag, pol, and rev genes are provided on the same plasmid (e.g. FIG. 1C). In another embodiment, the gag and pot genes are provided on a first plasmid and the rev gene is provided on a second plasmid (e.g., FIG. 1D). Accordingly, both 3-vector and 4-vector systems can be used to produce a lentivirus as described in the Examples section and elsewhere herein. The therapeutic vector, the envelope plasmid and at least one helper plasmid are transfected into a packaging cell line. A non-limiting example of a packaging cell line is the 293T/17 HEK cell line. When the therapeutic vector, the envelope plasmid, and at least one helper plasmid are transfected into the packaging cell line; a lentiviral particle is produced.

In another aspect, a lentiviral vector system for expressing a lentiviral particle is disclosed. The system includes a lentiviral vector as described herein; an envelope plasmid for expressing an envelope protein optimized for infecting a cell; and at least one helper plasmid for expressing gag, poi, and rev genes, wherein when the lentiviral vector, the envelope plasmid, and the at least one helper plasmid are transfected into a packaging cell line, a lentiviral particle is produced by the packaging cell line, wherein the lentiviral particle is capable of inhibiting production of PARP1.

Figure 1C:
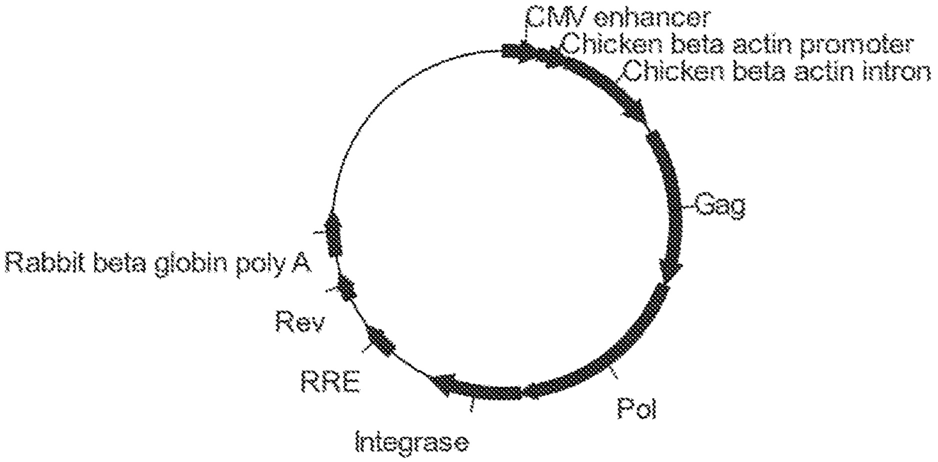
FIG. 1C depicts an 1.0 exemplary 3-vector lentiviral vector system in a circularized form that includes the experimental therapeutic vector detailed in FIG. 1A.
Figure 1C:
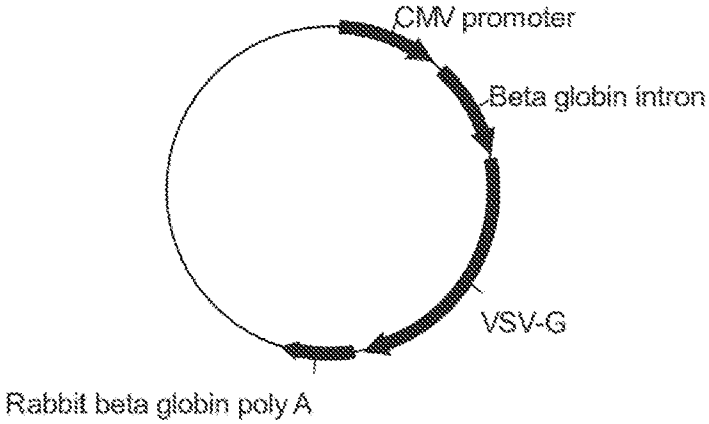
Figure 1C:
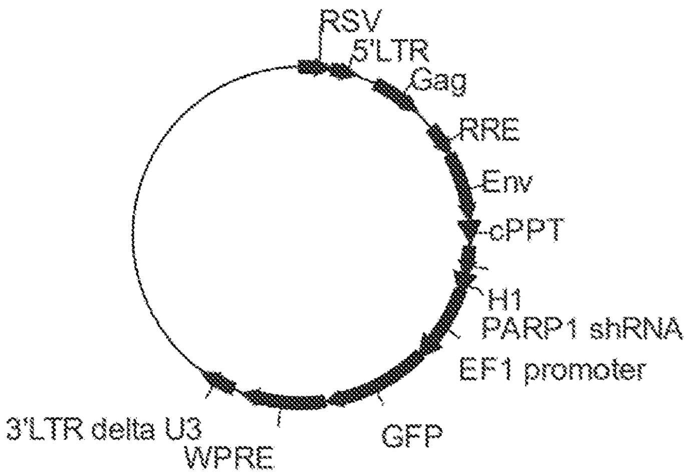

In another aspect, and as detailed in FIG. 1C, the lentiviral vector, which is also referred to herein as a therapeutic vector, includes the following elements: a hybrid 5' long terminal repeat (RSV/5' LTR) (SEQ ID NOS: 21-22), a HIV gag (SEQ ID NO: 23), a RRE (Rev-response element) (SEQ ID NO: 24), a Env element (SEQ ID NO: 25), a cPPT (SEQ ID NO: 26), a HI promoter (SEQ ID NO: 27), a shRNA targeting PARP1 (shPARP1) (SEQ ID NOS: 6-10), a EF1 promoter (SEQ ID NO: 28), a GFP element (SEQ ID NO:29), a Woodchuck Post-Transcriptional Regulatory Element (WPRE) (SEQ ID NO: 30), and a 3' LTR delta U3 (SEQ ID NO: 31). In another aspect, sequence variation, by way of substitution, deletion, addition, or mutation can be used to modify the sequences references herein.

In another aspect, and as detailed herein for example in FIG. 1C, a helper plasmid has been designed to include the following elements: CMV enhancer (SEQ ID NO: 32); a chicken beta actin promoter (SEQ ID NO: 33); a chicken beta actin intron (SEQ ID NO: 34); a HIV gag (SEQ ID NO: 23); a HIV Pol (SEQ ID NO: 35); a HIV Int (SEQ ID NO: 36); a HIV RRE (SEQ ID NO: 24); a HIV Rev (SEQ ID NO: 37): and a rabbit beta globin poly A (SEQ ID NO: 38), In another aspect, the helper plasmid may be modified to include a first helper plasmid for expressing the gag and pol genes, and a second and separate plasmid for expressing the rev gene. In another aspect, sequence variation, by way of substitution, deletion, addition, or mutation can be used to modify the sequences references herein.

In another aspect, and as detailed herein for example in FIG. 1C, an envelope plasmid has been designed to include the following elements being from left to right: a CMV promoter (SEQ ID NO: 39); a beta globin intron (SEQ ID NO; 40); a VSV-G (SEQ ID NO: 25); and a rabbit beta globin poly A (SEQ ID NO: 38). In another aspect, sequence variation, by way of substitution, deletion, addition, or mutation can be used to modify the sequences references herein.

In another aspect, the plasmids used for lentiviral packaging can be modified with similar elements and the intron sequences can potentially be removed without loss of vector function. For example, the following elements can replace similar elements in the plasmids that comprise the packaging system: Elongation Factor-1 (EF-1), phosphoglycerate kinase (PGK), and ubiquitin C (UbC) promoters can replace the CMV or CAG promoter. SV40 poly A and bGH poly A can replace the rabbit beta globin poly A. The HIV sequences in the helper plasmid can be constructed from different HIV strains or Glades. The VSV-G glycoprotein can be substituted with membrane glycoproteins from feline endogenous virus (RD114), gibbon ape leukemia virus (GALV), Rabies (FUG), lymphocytic choriomeningitis virus (LCMV), influenza A fowl plague virus (FIV), Ross River alphavirus (RRV), murine leukemia virus 10A1 (MIN), or Ebola virus (EboV).

Of note, lentiviral packaging systems can be acquired commercially (e.g., Lenti-vpak packaging kit from OriGene Technologies, Inc., Rockville, Md.), and can also be designed as described herein. Moreover, it is within the skill of a person skilled in the art to substitute or modify aspects of a lentiviral packaging system to improve any number of relevant factors, including the production efficiency of a lentiviral particle.

Doses and Dosage Forms

Dosing may occur once per day or several times per day. Dosing may occur with intervals in between dosing. For example, a subject may be treated on a first day, and then treated every other day, or every second day, or every third day, or every fourth day, or every fifth day, or every sixth day, or every seventh day, or every second week, or every month, etc. However, dosing can also occur once, twice, or several times per year, and such a dosing schedule can be repeated on a yearly basis. A lentiviral particle can be delivered by any method suitable for treating symptoms associated with PD. For example, dosing can be made via direct injection into the brain stem using a guided needle. This will likely occur in conjunction with deep brain stimulation.

In another aspect, a pharmaceutical composition comprising a lentiviral particle as described herein can be formulated in a solid dosage form. The solid dosage form can include excipients known to those skilled in the art. The lentiviral particle as described herein can be formulated in a gel form, a foam form, a biodegradable capsule form, a nanoparticle form, or can be formulated with liposomes or other structures known to those skilled in the art. The solid dosage form can be formulated for immediate release or a modified release. Modified release dosage forms include controlled or extended release forms.

The following examples are given for the purpose of illustrating various embodiments of the invention and are not meant to limit the invention in any fashion. The present examples, along with the methods described herein are presently representative of preferred embodiments, are exemplary, and are not intended as limitations on the scope of the invention. Changes therein, and other uses which are encompassed within the spirit or the invention as defined by the scope of the claims, will occur to those persons skilled in the art.

EXAMPLES

Example 1, Development of a Lentiviral Vector System

A lentiviral vector system was developed as summarized generally in FIG. 1. Lentiviral particles were produced in 293T/17 HEK cells (purchased from American Type Culture Collection, Manassas, Va.) following transfection with the therapeutic vector, the envelope plasmid, and the helper plasmid. The transfection of 293T/17 HEK cells, which produced functional viral particles, employed the reagent Poly(ethylenimine) (PEI) to increase the efficiency of plasmid DNA uptake. The plasmids and DNA were initially added separately in culture medium without serum in a ratio of 3:1 (mass ratio of PEI to DNA.). After 2-3 days, cell medium was collected and lentiviral particles were purified by high-speed centrifugation and/or filtration followed by anion-exchange chromatography. The concentration of lentiviral particles can be expressed in terms of transducing units/ml (TU/ml). The determination of TU was accomplished by measuring HIV p24 levels in culture fluids (p24 protein is incorporated into lentiviral particles), measuring the number of viral DNA copies per cell by quantitative PCR, or by infecting cells and using light (if the vectors encode luciferase or fluorescent protein markers).

Figure 1D:
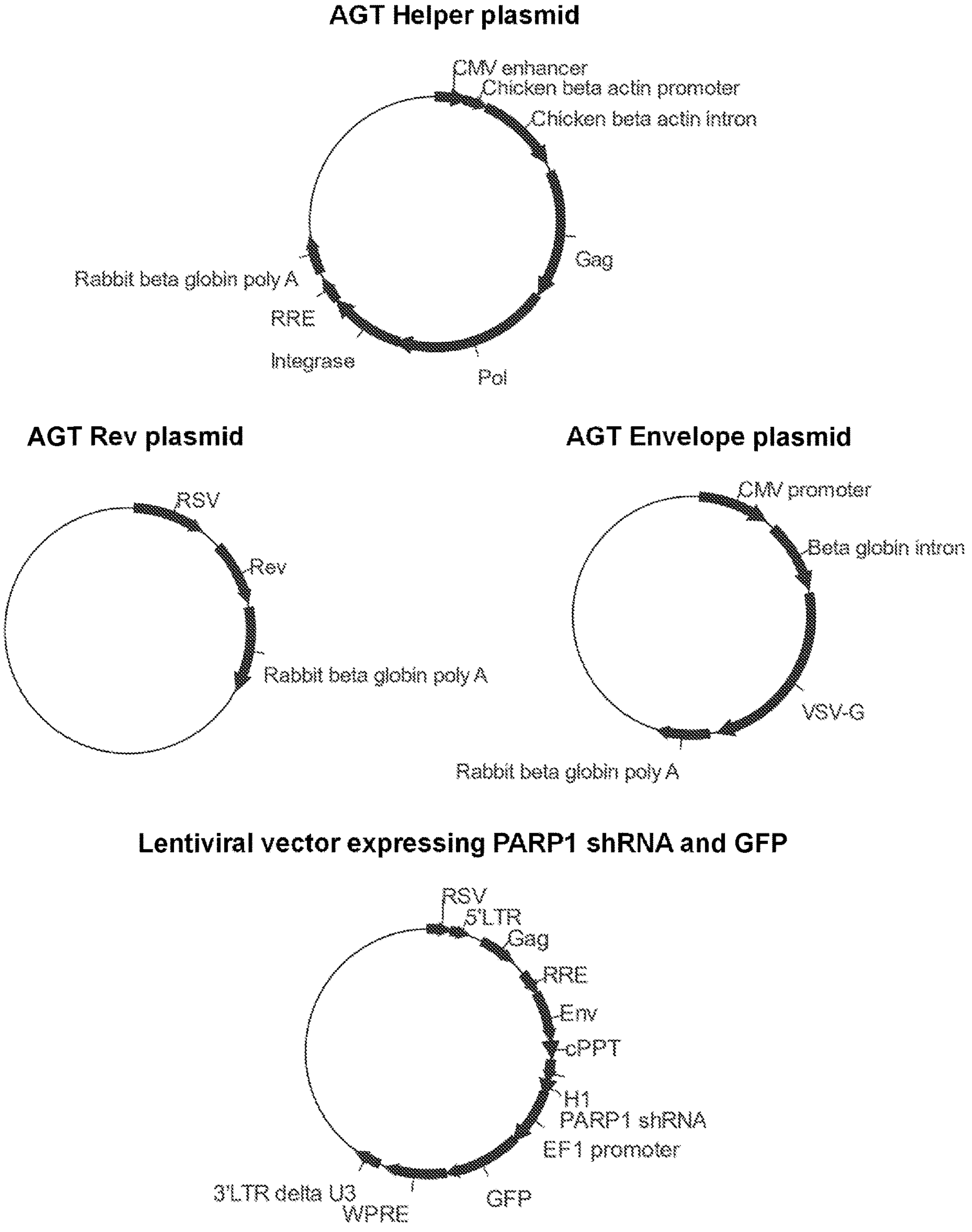
FIG. 1D depicts an exemplary 4-vector lentiviral vector system in a circularized form that includes the experimental therapeutic vector detailed in FIG. 1A.
Figure 1E:
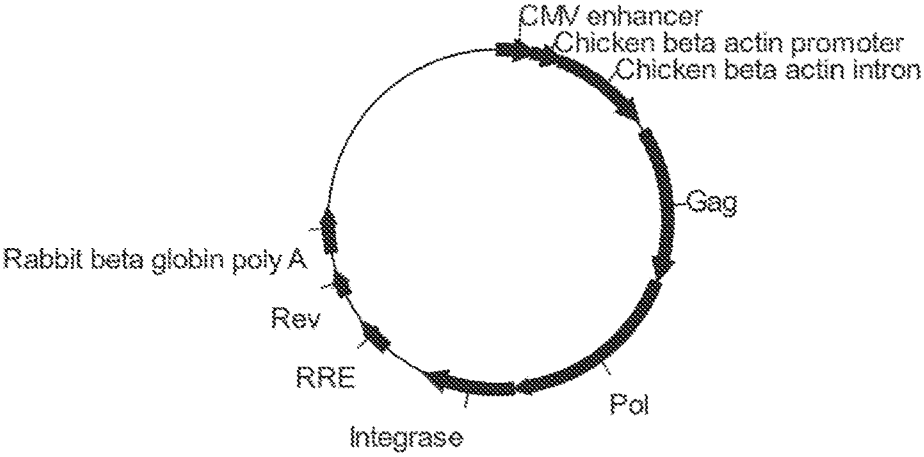
FIG. 1E depicts an exemplary 3-vector lentiviral vector system in a circularized form that includes the therapeutic vector detailed in FIG. 1B.
Figure 1E:
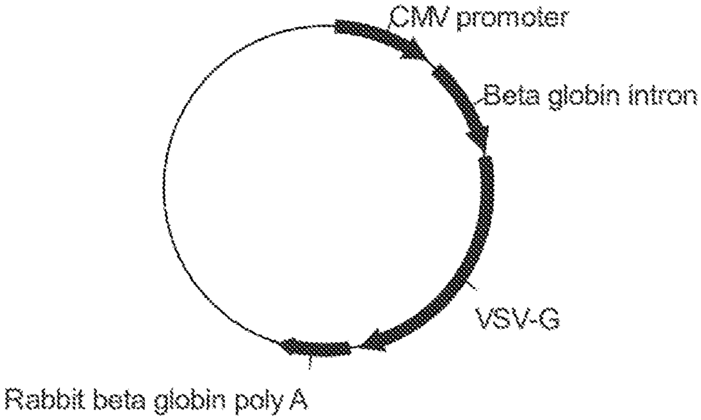
Figure 1E:
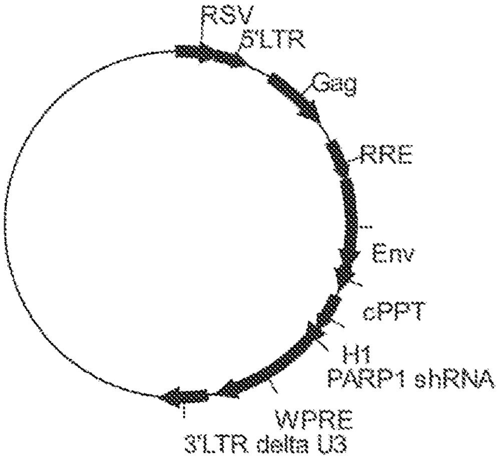

A 3-vector system (i.e., a 2-vector lentiviral packaging system) was designed for the production of lentiviral panicles. A schematic of the 3-vector system is shown in FIGS. 1A, 1C, and Briefly, and with reference to FIGS. 1C and 1E, the top-most vector is a helper plasmid, which, in this case, includes Rev. The vector appearing in the middle of FIGS. 1C and 1E is the envelope plasmid. The bottom-most vector is the therapeutic vector, as described herein.

Figure 1F:
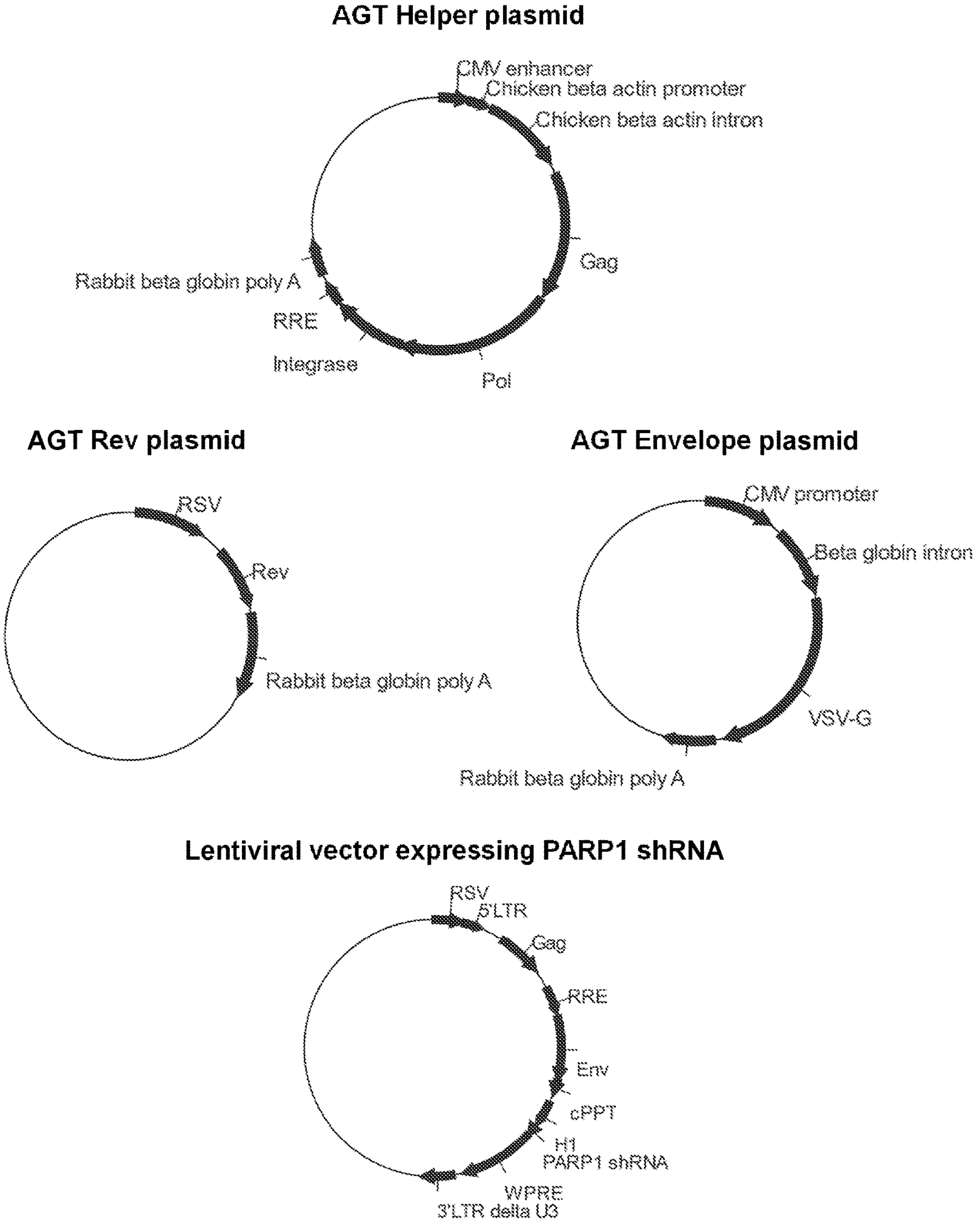
FIG. 1F depicts an exemplary 4-vector lentiviral vector system in a circularized form that includes the therapeutic vector detailed in FIG. 18.

Referring to FIGS. 1C and 1F, the Helper plus Rev plasmid includes a CMV enhancer (SEQ ID NO: 32); a chicken beta actin promoter (SEQ ID NO: 33); a chicken beta actin intron (SEQ ID NO: 34); a HIV gag (SEQ ID NO: 23); a HIV Pol (SEQ ID NO: 35); a HIV Int (SEQ ID NO: 36); a HIV RRE (SEQ ID NO: 24); a HIV Rev (SEQ ID NO: 37); and a rabbit beta globin poly A (SEQ ID NO: 38). The Helper plus Rev plasmid is also shown in a linear form in FIG. 1A.

Referring to FIGS. 1C and 1E, the Envelope plasmid includes a CMV promoter (SEQ ID NO: 39); a beta globin intron (SEQ ID NO: 40); a VSV-G (SEQ ID NO: 25); and a rabbit beta globin poly A (SEQ ID NO: 38). The Envelope plasmid is also shown in a linear form in FIG. 1A.)

Synthesis of a 2-Vector Lentiviral Packaging System Including Helper (Phis Rev) and Envelope Plasmids Materials and Methods:

Construction of the Helper Plasmid:

The helper plasmid was constructed by initial PCR amplification of a DNA fragment from the pNL4-3 HIV plasmid (NIH Aids Reagent Program) containing Gag, Pol, and Integrase genes. Primers were designed to amplify the fragment with EcoRI and NotI restriction sites which could be used to insert at the same sites in the pCDNA3 plasmid (Invitrogen). The forward primer was (5'-TAAGCAGAATTC ATGAATTTGCCAGGAAGAT-3') (SEQ ID NO: 41) and reverse primer was (5% CCATACAATGAATGGACACTAGGCGGCCGCACGAAT-3') (SEQ ID NO: 42).

The sequence for the Gag, Pol, Integrase fragment was as follows:

(SEQ ID NO: 43)

GAATTCATGAATTTGCCAGGAAGATGGAAACCAAAAATGATAGGGGGAATTGGA

GGTTTTATCAAAGTAAGACAGTATGATCAGATACTCATAGAAATCTGCGGACATA

-continued

AAGCTATAGGTACAGTATTAGTAGGACCTACACCTGTCAACATAATTGGAAGAA

ATCTGTTGACTCAGATTGGCTGCACTTTAAATTTTCCCATTAGTCCTATTGAGACT

GTACCAGTAAAATTAAAGCCAGGAATGGATGGCCCAAAAGTTAAACAATGGCCA

TTGACAGAAGAAAAAATAAAAGCATTAGTAGAAATTTGTACAGAAATGGAAAAG

GAAGGAAAAATTTCAAAAATTGGGCCTGAAAATCCATACAATACTCCAGTATTT

GCCATAAAGAAAAAAGACAGTACTAAATGGAGAAAATTAGTAGATTTCAGAGAA

CTTAATAAGAGAACTCAAGATTTCTGGGAAGTTCAATTAGGAATACCACATCCTG

CAGGGTTAAAACAGAAAAAATCAGTAACAGTACTGGATGTGGGCGATGCATATT

TTTCAGTTCCCTTAGATAAAGACTTCAGGAAGTATACTGCATTTACCATACCTAG

TATAAACAATGAGACACCAGGGATTAGATATCAGTACAATGTGCTTCCACAGGG

ATGGAAAGGATCACCAGCAATATTCCAGTGTAGCATGACAAAAATCTTAGAGCC

TTTTAGAAAACAAAATCCAGACATAGTCATCTATCAATACATGGATGATTTGTAT

GTAGGATCTGACTTAGAAATAGGGCAGCATAGAACAAAAATAGAGGAACTGAG

ACAACATCTGTTGAGGTGGGGATTTACCACACCAGACAAAAAACATCAGAAAGA

ACCTCCATTCCTTTGGATGGGTTATGAACTCCATCCTGATAAATGGACAGTACAG

CCTATAGTGCTGCCAGAAAAGGACAGCTGGACTGTCAATGACATACAGAAATTA

GTGGGAAAATTGAATTGGGCAAGTCAGATTTATGCAGGGATTAAAGTAAGGCAA

TTATGTAAACTTCTTAGGGGAACCAAAGCACTAACAGAAGTAGTACCACTAACA

GAAGAAGCAGAGCTAGAACTGGCAGAAAACAGGGAGATTCTAAAAGAACCGGT

ACATGGAGTGTATTATGACCCATCAAAAGACTTAATAGCAGAAATACAGAAGCA

GGGGCAAGGCCAATGGACATATCAAATTTATCAAGAGCCATTTAAAAATCTGAA

AACAGGAAAGTATGCAAGAATGAAGGGTGCCCACACTAATGATGTGAAACAATT

AACAGAGGCAGTACAAAAAATAGCCACAGAAAGCATAGTAATATGGGGAAAGA

CTCCTAAATTTAAATTACCCATACAAAAGGAAACATGGGAAGCATGGTGGACAG

AGTATTGGCAAGCCACCTGGATTCCTGAGTGGGAGTTTGTCAATACCCCTCCCTT

AGTGAAGTTATGGTACCAGTTAGAGAAAGAACCCATAATAGGAGCAGAAACTTT

CTATGTAGATGGGGCAGCCAATAGGGAAACTAAATTAGGAAAAGCAGGATATGT

AACTGACAGAGGAAGACAAAAAGTTGTCCCCCTAACGGACACAACAAATCAGAA

GACTGAGTTACAAGCAATTCATCTAGCTTTGCAGGATTCGGGATTAGAAGTAAAC

ATAGTGACAGACTCACAATATGCATTGGGAATCATTCAAGCACAACCAGATAAG

AGTGAATCAGAGTTAGTCAGTCAAATAATAGAGCAGTTAATAAAAAAGGAAAAA

GTCTACCTGGCATGGGTACCAGCACACAAAGGAATTGGAGGAAATGAACAAGTA

GATAAATTGGTCAGTGCTGGAATCAGGAAAGTACTATTTTTAGATGGAATAGATA

AGGCCCAAGAAGAACATGAGAAATATCACAGTAATTGGAGAGCAATGGCTAGTG

ATTTTAACCTACCACCTGTAGTAGCAAAAGAAATAGTAGCCAGCTGTGATAAATG

TCAGCTAAAAGGGGAAGCCATGCATGGACAAGTAGACTGTAGCCCAGGAATATG

GCAGCTAGATTGTACACATTTAGAAGGAAAAGTTATCTTGGTAGCAGTTCATGTA

GCCAGTGGATATATAGAAGCAGAAGTAATTCCAGCAGAGACAGGGCAAGAAAC

AGCATACTTCCTCTTAAAATTAGCAGGAAGATGGCCAGTAAAAACAGTACATAC

AGACAATGGCAGCAATTTCACCAGTACTACAGTTAAGGCCGCCTGTTGGTGGGC

-continued

GGGGATCAAGCAGGAATTTGGCATTCCCTACAATCCCCAAAGTCAAGGAGTAAT

AGAATCTATGAATAAAGAATTAAAGAAAATTATAGGACAGGTAAGAGATCAGGC

TGAACATCTTAAGACAGCAGTACAAATGGCAGTATTCATCCACAATTTTAAAAGA

AAAGGGGGGATTGGGGGGTACAGTGCAGGGGAAAGAATAGTAGACATAATAGC

AACAGACATACAAACTAAAGAATTACAAAAACAAATTACAAAAATTCAAAATTT

TCGGGTTTATTACAGGGACAGCAGAGATCCAGTTTGGAAAGGACCAGCAAAGCT

CCTCTGGAAAGGTGAAGGGGCAGTAGTAATACAAGATAATAGTGACATAAAAGT

AGTGCCAAGAAGAAAAGCAAAGATCATCAGGGATTATGGAAAACAGATGGCAG

GTGATGATTGTGTGGCAAGTAGACAGGATGAGGATTAA

Next, a DNA fragment containing the Rev, RRE, and rabbit beta globin poly A sequence with XbaI and XmaI flanking restriction sites was synthesized by MWG Operon. The DNA fragment was then inserted into the plasmid at the XbaI and XmaI restriction sites The DNA sequence was as follows:

(SEQ ID NO: 44)

TCTAGAATGGCAGGAAGAAGCGGAGACAGCGACGAAGAGCTCATCAGAA

CAGTCAGACTCATCAAGCTTCTCTATCAAAGCAACCCACCTCCCAATCC

CGAGGGGACCCGACAGGCCCGAAGGAATAGAAGAAGAAGGTGGAGAGAG

AGACAGAGACAGATCCATTCGATTAGTGAACGGATCCTTGGCACTTATC

TGGGACGATCTGCGGAGCCTGTGCCTCTTCAGCTACCACCGCTTGAGAG

ACTTACTCTTGATTGTAACGAGGATTGTGGAACTTCTGGGACGCAGGGG

GTGGGAAGCCCTCAAATATTGGTGGAATCTCCTACAATATTGGAGTCAG

GAGCTAAAGAATAGAGGAGCTTTGTTCCTTGGGTTCTTGGGAGCAGCAG

GAAGCACTATGGGCGCAGCGTCAATGACGCTGACGGTACAGGCCAGACA

ATTATTGTCTGGTATAGTGCAGCAGCAGAACAATTTGCTGAGGGCTATT

GAGGCGCAACAGCATCTGTTGCAACTCACAGTCTGGGGCATCAAGCAGC

TCCAGGCAAGAATCCTGGCTGTGGAAAGATACCTAAAGGATCAACAGCT

CCTAGATCTTTTTCCCTCTGCCAAAAATTATGGGGACATCATGAAGCCC

CTTGAGCATCTGACTTCTGGCTAATAAAGGAAATTTATTTTCATTGCAA

TAGTGTGTTGGAATTTTTTGTGTCTCTCACTCGGAAGGACATATGGGAG

GGCAAATCATTTAAAACATCAGAATGAGTATTTGGTTTAGAGTTTGGCA

ACATATGCCATATGCTGGCTGCCATGAACAAAGGTGGCTATAAAGAGGT

CATCAGTATATGAAACAGCCCCCTGCTGTCCATTCCTTATTCCATAGAA

AAGCCTTGACTTGAGGTTAGATTTTTTTTATATTTTGTTTTGTGTTATT

TTTTTCTTTAACATCCCTAAAATTTTCCTTACATGTTTTACTAGCCAGA

TTTTTCCTCCTCTCCTGACTACTCCCAGTCATAGCTGTCCCTCTTCTCT

TATGAAGATCCCTCGACCTGCAGCCCAAGCTTGGCGTAATCATGGTCAT

AGCTGTTTCCTGTGTGAAATTGTTATCCGCTCACAATTCCACACAACAT

ACGAGCCGGAAGCATAAAGTGTAAAGCCTGGGGTGCCTAATGAGTGAGC

TAACTCACATTAATTGCGTTGCGCTCACTGCCCGCTTTCCAGTCGGGAA

ACCTGTCGTGCCAGCGGATCCGCATCTCAATTAGTCAGCAACCATAGTC

-continued

CCGCCCCTAACTCCGCCCATCCCGCCCCTAACTCCGCCCAGTTCCGCCC

ATTCTCCGCCCCATGGCTGACTAATTTTTTTTATTTATGCAGAGGCCGA

GGCCGCCTCGGCCTCTGAGCTATTCCAGAAGTAGTGAGGAGGCTTTTTT

GGAGGCCTAGGCTTTTGCAAAAAGCTAACTTGTTTATTGCAGCTTATAA

TGGTTACAAATAAAGCAATAGCATCACAAATTTCACAAATAAAGCATTT

TTTTCACTGCATTCTAGTTGTGGTTTGTCCAAACTCATCAATGTATCTT

ATCAGCGGCCGCCCCGGG

Finally, the CMV promoter of pCDNA3.1 was replaced with the CAG enhancer/promoter plus a chicken beta actin intron sequence. A DNA fragment containing the CAG enhancer/promoter/intron sequence with MluI and EcoRI flanking restriction sites was synthesized by MWG Operon. The DNA fragment was then inserted into the plasmid at the MluI and EcoRI restriction sites. The DNA sequence was as follows:

(SEQ ID NO: 45)

ACGCGTTAGTTATTAATAGTAATCAATTACGGGGTCATTAGTTCATAGC

CCATATATGGAGTTCCGCGTTACATAACTTACGGTAAATGGCCCGCCTG

GCTGACCGCCCAACGACCCCCGCCCATTGACGTCAATAATGACGTATGT

TCCCATAGTAACGCCAATAGGGACTTTCCATTGACGTCAATGGGTGGAC

TATTTACGGTAAACTGCCCACTTGGCAGTACATCAAGTGTATCATATGC

CAAGTACGCCCCCTATTGACGTCAATGACGGTAAATGGCCCGCCTGGCA

TTATGCCCAGTACATGACCTTATGGGACTTTCCTACTTGGCAGTACATC

TACGTATTAGTCATCGCTATTACCATGGGTCGAGGTGAGCCCCACGTTC

TGCTTCACTCTCCCCATCTCCCCCCCCTCCCCACCCCCAATTTTGTATT

TATTTATTTTTTAATTATTTTGTGCAGCGATGGGGGCGGGGGGGGGGGG

GGCGCGCGCCAGGCGGGGCGGGGCGGGGCGAGGGGCGGGGCGGGGCGAG

GCGGAGAGGTGCGGCGGCAGCCAATCAGAGCGGCGCGCTCCGAAAGTTT

CCTTTTATGGCGAGGCGGCGGCGGCGGCGGCCCTATAAAAAGCGAAGCG

CGCGGCGGGCGGGAGTCGCTGCGTTGCCTTCGCCCCGTGCCCCGCTCCG

CGCCGCCTCGCGCCGCCCGCCCCGGCTCTGACTGACCGCGTTACTCCCA

CAGGTGAGCGGGCGGGACGGCCCTTCTCCTCCGGGCTGTAATTAGCGCT

TGGTTTAATGACGGCTCGTTTCTTTTCTGTGGCTGCGTGAAAGCCTTAA

-continued

AGGGCTCCGGGAGGGCCCTTTGTGCGGGGGGGAGCGGCTCGGGGGGTGC

GTGCGTGTGTGTGTGCGTGGGGAGCGCCGCGTGCGGCCCGCGCTGCCCG

GCGGCTGTGAGCGCTGCGGGCGCGGCGCGGGGCTTTGTGCGCTCCGCGT

GTGCGCGAGGGGAGCGCGGCCGGGGGCGGTGCCCCGCGGTGCGGGGGGG

CTGCGAGGGGAACAAAGGCTGCGTGCGGGGTGTGTGCGTGGGGGGGTGA

GCAGGGGGTGTGGGCGCGGCGGTCGGGCTGTAACCCCCCCCTGCACCCC

CCTCCCCGAGTTGCTGAGCACGGCCCGGCTTCGGGTGCGGGGCTCCGTG

CGGGGCGTGGCGCGGGGCTCGCCGTGCCGGGCGGGGGGTGGCGGCAGGT

GGGGGTGCCGGGCGGGGCGGGGCCGCCTCGGGCCGGGGAGGGCTCGGGG

GAGGGGCGCGGCGGCCCCGGAGCGCCGGCGGCTGTCGAGGCGCGGCGAG

CCGCAGCCATTGCCTTTTATGGTAATCGTGCGAGAGGGCGCAGGGACTT

CCTTTGTCCCAAATCTGGCGGAGCCGAAATCTGGGAGGCGCCGCCGCAC

CCCCTCTAGCGGGCGCGGGCGAAGCGGTGCGGCGCCGGCAGGAAGGAAA

TGGGCGGGGAGGGCCTTCGTGCGTCGCCGCGCCGCCGTCCCCTTCTCCA

TCTCCAGCCTCGGGGCTGCCGCAGGGGGACGGCTGCCTTCGGGGGGGAC

GGGGCAGGGCGGGGTTCGGCTTCTGGCGTGTGACCGGCGGGAATTC

Construction of the HSV-G Envelope Plasmid:

The vesicular stomatitis Indiana virus glycoprotein (VSV-G) sequence was synthesized by MWG Operon with thinking EcoRI restriction sites. The DNA fragment was then inserted into the pCDNA3.1 plasmid (Invitrogen) at the EcoRI restriction site and the correct orientation was determined by sequencing using a CMV specific primer. The DNA sequence was as Follows:

(SEQ ID NO: 46)

GAATTCATGAAGTGCCTTTTGTACTTAGCCTTTTTATTCATTGGGGTGA

ATTGCAAGTTCACCATAGTTTTTCCACACAACCAAAAAGGAAACTGGAA

AAATGTTCCTTCTAATTACCATTATTGCCCGTCAAGCTCAGATTTAAAT

TGGCATAATGACTTAATAGGCACAGCCTTACAAGTCAAAATGCCCAAGA

GTCACAAGGCTATTCAAGCAGACGGTTGGATGTGTCATGCTTCCAAATG

GGTCACTACTTGTGATTTCCGCTGGTATGGACCGAAGTATATAACACAT

TCCATCCGATCCTTCACTCCATCTGTAGAACAATGCAAGGAAAGCATTG

AACAAACGAAACAAGGAACTTGGCTGAATCCAGGCTTCCCTCCTCAAAG

TTGTGGATATGCAACTGTGACGGATGCCGAAGCAGTGATTGTCCAGGTG

ACTCCTCACCATGTGCTGGTTGATGAATACACAGGAGAATGGGTTGATT

CACAGTTCATCAACGGAAAATGCAGCAATTACATATGCCCCACTGTCCA

TAACTCTACAACCTGGCATTCTGACTATAAGGTCAAAGGGCTATGTGAT

TCTAACCTCATTTCCATGGACATCACCTTCTTCTCAGAGGACGGAGAGC

TATCATCCCTGGGAAAGGAGGGCACAGGGTTCAGAAGTAACTACTTTGC

TTATGAAACTGGAGGCAAGGCCTGCAAAATGCAATACTGCAAGCATTGG

GGAGTCAGACTCCCATCAGGTGTCTGGTTCGAGATGGCTGATAAGGATC

TCTTTGCTGCAGCCAGATTCCCTGAATGCCCAGAAGGGTCAAGTATCTC

TGCTCCATCTCAGACCTCAGTGGATGTAAGTCTAATTCAGGACGTTGAG

-continued

AGGATCTTGGATTATTCCCTCTGCCAAGAAACCTGGAGCAAAATCAGAG

CGGGTCTTCCAATCTCTCCAGTGGATCTCAGCTATCTTGCTCCTAAAAA

CCCAGGAACCGGTCCTGCTTTCACCATAATCAATGGTACCCTAAAATAC

TTTGAGACCAGATACATCAGAGTCGATATTGCTGCTCCAATCCTCTCAA

GAATGGTCGGAATGATCAGTGGAACTACCACAGAAAGGGAACTGTGGGA

TGACTGGGCACCATATGAAGACGTGGAAATTGGACCCAATGGAGTTCTG

AGGACCAGTTCAGGATATAAGTTTCCTTTATACATGATTGGACATGGTA

TGTTGGACTCCGATCTTCATCTTAGCTCAAAGGCTCAGGTGTTCGAACA

TCCTCACATTCAAGACGCTGCTTCGCAACTTCCTGATGATGAGAGTTTA

TTTTTTGGTGATACTGGGCTATCCAAAAATCCAATCGAGCTTGTAGAAG

GTTGGTTCAGTAGTTGGAAAAGCTCTATTGCCTCTTTTTTCTTTATCAT

AGGGTTAATCATTGGACTATTCTTGGTTCTCCGAGTTGGTATCCATCTT

TGCATTAAATTAAAGCACACCAAGAAAAGACAGATTTATACAGACATAG

AGATGAGAATTC

A 4-vector system (i.e., a 3-vector lentiviral packaging system) has also been designed and produced using the methods and materials described herein. A schematic of the 4-vector system is shown in FIGS. 1D and 1F. Briefly, and with reference to FIGS. 1D and 1F, the top-most vector is a helper plasmid, which, in this case, does not include Rev. The vector second from the top, oriented at the left aspect of the page, is a separate Rev plasmid. The vector second from the bottom, oriented at the right aspect of the page, is the envelope plasmid. The bottom-most vector is an experimental therapeutic vector.

Referring to FIGS. 1D and 1F, the Helper plasmid includes a CMV enhancer (SEQ 113 NO: 32); a chicken beta actin promoter (SEQ ID NO: 33); a chicken beta actin intron (SEQ ID NO: 34); a HIV gag (SEQ ID NO: 23); a HIV Pol (SEQ ID NO: 35); a HIV Int (SEQ ID NO: 36); a HIV RRE (SEQ ID NO: 24); and a rabbit beta globin poly A (SEQ ID NO: 38).

Referring to FIGS. 1D and 1F, the Rev plasmid includes a RSV promoter (SEQ ID NO: 47); a HIV Rev (SEQ ID NO: 37); and a rabbit beta globin poly A (SEQ ID NO: 38).

Referring to FIGS. 1D and 1F, the Envelope plasmid includes a CMV promoter (SEQ ID NO: 39); a beta globin intron (SEQ ID NO: 40); a VSV-G (SEQ ID NO: 25); and a rabbit beta globin poly A (SEQ ID NO: 38). The Envelope plasmid is also shown in a linear form in FIG. 1A.

Synthesis of a 3-Vector Lentiviral Packaging System Including Helper, Rev, and Envelope Plasmas Materials and Methods:

Construction of the Helper Plasmid without Rev:

The Helper plasmid without Rev was constructed by inserting a DNA fragment containing the RRE and rabbit beta globin poly A sequence. This sequence was synthesized by MWG Operon with flanking XbaI and XmaI restriction sites. The RRE/rabbit poly A beta globin sequence was then inserted into the Helper plasmid at the XbaI and XmaI restriction sites. The DNA sequence is as follows:

(SEQ ID NO: 44)

TCTAGAAGGAGCTTTGTTCCTTGGGTTCTTGGGAGCAGCAGGAAGCACT

ATGGGCGCAGCGTCAATGACGCTGACGGTACAGGCCAGACAATTATTGT

CTGGTATAGTGCAGCAGCAGAACAATTTGCTGAGGGCTATTGAGGCGCA

ACAGCATCTGTTGCAACTCACAGTCTGGGGCATCAAGCAGCTCCAGGCA

AGAATCCTGGCTGTGGAAAGATACCTAAAGGATCAACAGCTCCTAGATC

TTTTTCCCTCTGCCAAAAATTATGGGGACATCATGAAGCCCCTTGAGCA

TCTGACTTCTGGCTAATAAAGGAAATTTATTTTCATTGCAATAGTGTGT

TGGAATTTTTTGTGTCTCTCACTCGGAAGGACATATGGGAGGGCAAATC

ATTTAAAACATCAGAATGAGTATTTGGTTTAGAGTTTGGCAACATATGC

CATATGCTGGCTGCCATGAACAAAGGTGGCTATAAAGAGGTCATCAGTA

TATGAAACAGCCCCCTGCTGTCCATTCCTTATTCCATAGAAAAGCCTTG

ACTTGAGGTTAGATTTTTTTTATATTTTGTTTTGTGTTATTTTTTTCTT

TAACATCCCTAAAATTTTCCTTACATGTTTTACTAGCCAGATTTTTCCT

CCTCTCCTGACTACTCCCAGTCATAGCTGTCCCTCTTCTCTTATGAAGA

TCCCTCGACCTGCAGCCCAAGCTTGGCGTAATCATGGTCATAGCTGTTT

CCTGTGTGAAATTGTTATCCGCTCACAATTCCACACAACATACGAGCCG

GAAGCATAAAGTGTAAAGCCTGGGGTGCCTAATGAGTGAGCTAACTCAC

ATTAATTGCGTTGCGCTCACTGCCCGCTTTCCAGTCGGGAAACCTGTCG

TGCCAGCGGATCCGCATCTCAATTAGTCAGCAACCATAGTCCCGCCCCT

AACTCCGCCCATCCCGCCCCTAACTCCGCCCAGTTCCGCCCATTCTCCG

CCCCATGGCTGACTAATTTTTTTTATTTATGCAGAGGCCGAGGCCGCCT

CGGCCTCTGAGCTATTCCAGAAGTAGTGAGGAGGCTTTTTTGGAGGCCT

AGGCTTTTGCAAAAAGCTAACTTGTTTATTGCAGCTTATAATGGTTACA

AATAAAGCAATAGCATCACAAATTTCACAAATAAAGCATTTTTTTCACT

GCATTCTAGTTGTGGTTTGTCCAAACTCATCAATGTATCTTATCACCCG

GG

Construction of the Rev Plasmid:

The RSV promoter and HIV Rev sequence was synthesized as a single DNA fragment by MWG Operon with flanking MfeI and XbaI restriction sites. The DNA fragment was then inserted into the pCDNA3.1 plasmid (Invitrogen) at the MfeI and XbaI restriction sites in which the CMV promoter is replaced with the RSV promoter. The DNA sequence was as follows:

(SEQ ID NO: 48)

CAATTGCGATGTACGGGCCAGATATACGCGTATCTGAGGGGACTAGGGT

GTGTTTAGGCGAAAAGCGGGGCTTCGGTTGTACGCGGTTAGGAGTCCCC

TCAGGATATAGTAGTTTCGCTTTTGCATAGGGAGGGGGAAATGTAGTCT

TATGCAATACACTTGTAGTCTTGCAACATGGTAACGATGAGTTAGCAAC

ATGCCTTACAAGGAGAGAAAAAGCACCGTGCATGCCGATTGGTGGAAGT

AAGGTGGTACGATCGTGCCTTATTAGGAAGGCAACAGACAGGTCTGACA

TGGATTGGACGAACCACTGAATTCCGCATTGCAGAGATAATTGTATTTA

AGTGCCTAGCTCGATACAATAAACGCCATTTGACCATTCACCACATTGG

-continued

TGTGCACCTCCAAGCTCGAGCTCGTTTAGTGAACCGTCAGATCGCCTGG

AGACGCCATCCACGCTGTTTTGACCTCCATAGAAGACACCGGGACCGAT

CCAGCCTCCCCTCGAAGCTAGCGATTAGGCATCTCCTATGGCAGGAAGA

AGCGGAGACAGCGACGAAGAACTCCTCAAGGCAGTCAGACTCATCAAGT

TTCTCTATCAAAGCAACCCACCTCCCAATCCCGAGGGGACCCGACAGGC

CCGAAGGAATAGAAGAAGAAGGTGGAGAGAGAGACAGAGACAGATCCAT

TCGATTAGTGAACGGATCCTTAGCACTTATCTGGGACGATCTGCGGAGC

CTGTGCCTCTTCAGCTACCACCGCTTGAGAGACTTACTCTTGATTGTAA

CGAGGATTGTGGAACTTCTGGGACGCAGGGGGTGGGAAGCCCTCAAATA

TTGGTGGAATCTCCTACAATATTGGAGTCAGGAGCTAAAGAATAGTCTA

GA

The plasmids for the 3-vector and 4-vector packaging systems can be modified with similar elements and the intron sequences could potentially be removed without loss of vector function. For example, the following elements could replace similar elements in the 3-vector and 4-vector packaging system:

Promoters: Elongation Factor-1 (EF-1) (SEQ ID NO: 28), phosphoglycerate kinase (PGK) (SEQ ID NO: 49), and ubiquitin C (UbC) (SEQ ID NO: 50) can replace the CMV or CAG promoter (SEQ ID NO: 39). These sequences can also be further varied by addition, substitution, deletion or mutation.

Poly A sequences: SV40 poly A (SEQ ID NO: 51) and bGH poly A (SEQ ID NO: 52) can replace the rabbit beta globin poly A (SEQ ID NO: 38). These sequences can also be further varied by addition, substitution, deletion or mutation.

HIV Gag, Pol, and Integrase sequences: the HIV sequences in the Helper plasmid can be constructed from different HIV strains or clades. For example, HIV Gag (SEQ ID NO: 23); HIV P01 (SEQ ID NO: 35); and HIV Int (SEQ ID NO: 36) from the Bal strain can be interchanged with the gag, poi, and int sequences contained in the helper/helper plus Rev plasmids as outlined herein. These sequences can also be further varied by addition, substitution, deletion or mutation.

Envelope: The VSV-G glycoprotein can be substituted with membrane glycoproteins from feline endogenous virus (RD114) (SEQ ID NO: 53), gibbon ape leukemia virus (GALV) (SEQ ID NO: 54), Rabies (FUG) (SEQ ID NO: 55), lymphocytic choriomeningitis virus (MCMV) (SEQ ID NO: 56), influenza A fowl plague virus (FPV) (SEQ ID NO: 57), Ross River alphavirus (RRV) (SEQ 11) NO: 58), murine leukemia virus 10A1 (MLV) (SEQ ID NO: 59), or Ebola virus (EboV) (SEQ ID NO: 60). Sequences for these envelopes are identified in the sequence portion herein. Further, these sequences can also be further varied by addition, substitution, deletion or mutation.

In summary, the 3-vector versus 4-vector systems can be compared and contrasted, in part, as follows. The 3-vector lentiviral vector system contains: 1. Helper plasmid: HIV Gag. Pol, Integrase, and Rev/Tat; 2. Envelope plasmid: VSV-G envelope; and 3. Therapeutic vector: RSV/5' LTR, HIV Gag; RRE, Env, cPPT, shPARP1, EF1, GFP, WPRE, and a 3'LTR Δ U3. The 4-vector lentiviral vector system contains: I. Helper plasmid: HIV Gag, 1.0 Pol, and Integrase; 2. Rev plasmid: Rev; 3. Envelope plasmid: VSV-G envelope; and 4. Therapeutic vector: RSV/5' LTR, HIV Gag, RRE, Env, a cPPT, a element, shPARP1, EF1, GFP, WPRE, and a 3'Δ LTR. Sequences corresponding with the above elements are identified in the sequence listings portion herein.

Example 2. Development of PARP1 Inhibitory RNA for USC in a Lentiviral Vector in the Lentiviral Vector System The purpose of this Example was to develop a PARP1 inhibitor RNA lentivirus vector.

Inhibitory RNA Design.

The sequence of *Homo sapiens* poly ADP-ribose polymerase (PARP1) mRNA (NM_001618) or *Mus musculus* Parp1 mRNA (NM_007415) was used to search for potential siRNA or shRNA candidates to knock-down PARP1 levels in human or mouse cells, Potential RNA interference sequences were chosen from candidates selected by siRNA or shRNA design programs such as those from the Broad Institute (MIT) Genetic Perturbation Platform (GPP) Web Portal or the BLOCK-iT™ RNAi Designer from ThermoFisher Scientific. Potential RNA interference sequences were chosen from candidates selected by siRNA or shRNA design programs such as from GPP Web Portal hosted by the Broad Institute (portals.broadinstitute.org/gpp/public/) or the BLOCK-iT RNAi Designer from Thermo Scientific (maidesigner, thermofisher.com/maiexpress/).

Vector construction. For PARP1 shRNAs, oligonucleotide sequences containing BamHI and EcoRI restriction sites were synthesized by MWG operon. Oligonucleotide sequences were annealed by incubation at 70 degrees Celsius and cooling to room temperature. Annealed Oligonucleotides were digested with the restriction enzymes BamHI and EcoRI for one hour at 37 degrees Celsius and then the enzymes were heat-inactivated at 70 degrees Celsius for 20 minutes. In parallel, a lentiviral vector was digested with the restriction enzymes BamHI and EcoRI for one hour at 37 degrees Celsius. The digested lentiviral vector was purified by agarose gel electrophoresis and extracted from the gel using a DNA gel extraction kit from Invitrogen. The DNA concentration was determined by spectrophotometry at the absorbance wavelength of 260 nm. The vector and oligonucleotide sequences were ligated in the ratio 3:1 (insert to vector). The ligation reaction was carried out with T4 DNA ligase for 30 minutes at room temperature. 2.5 microliters of the ligation mixture was added to 25 microliters of STBL3 competent bacterial cells. Transformation was carried out by heat-shock at 42 degrees Celsius. Bacterial cells wore streaked onto agar plates containing ampicillin and then colonies were expanded in LB broth. To check for insertion or the oligo sequences, plasmid DNA was extracted from harvested bacteria cultures with the Invitrogen DNA mini prep kit. Insertion of the shRNA sequence in the lentiviral vector was verified by DNA sequencing using a specific primer for which ever promoter is used to regulate shRNA expression. The lentiviral vectors containing a correct PARP1 sequence were then used to package lentiviral particles to test for their ability to knockdown PARP1, Mammalian cells were transduced with lentiviral particles either in the presence or absence of polybrene. Cells were collected after 2-4 days and protein was analyzed by western blot for PARP1 expression.

The *Homo sapiens* PARP1 target sequences summarized in Table 1 were identified in respect of these experiments and in relation to the shRNA oligonucleotide sequences outlined in Table 2 herein.

TABLE 1

*Homo sapiens* PARP1 Target Sequences

| SEQ ID NO.: | Sequence |
|---|---|
| 1 | CTTCGTTAGAATGTCTGCCTT |
| 2 | GCAGCTTCATAACCGAAGATT |
| 3 | CCGAGAAATCTCTTACCTCAA |
| 4 | CGACCTGATCTGGAACATCAA |
| 5 | GTTGCTGATGGGTAGTACC |

The following *Homo sapiens* PARP1 shRNA oligonucleotide sequences summarized in Table 2 were used in these experiments:

TABLE 2

*Homo sapiens* PARP1 shRNA Oligonucleotide Sequences

| SEQ ID NO.: | Sequence |
|---|---|
| 6 | CTTCGTTAGAATGTCTGCCTTCTCGAGAAGGCAGACATTCTAACGAAGTTTTT |
| 7 | GCAGCTTCATAACCGAAGATTCTCGAGAATCTTCGGTTATGAAGCTGCTTTTT |
| 8 | CCGAGAAATCTCTTACCTCAACTCGAGTTGAGGTAAGAGATTTCTCGGTTTTT |
| 9 | CGACCTGATCTGGAACATCAACTCGAGTTGATGTTCCAGATCAGGTCGTTTTT |
| 10 | GTTGCTGATGGGTAGTACCTTCAAGAGAGGTACTACCCATCAGCAACTTTTT |

The *Mus musculus* PARP1 target sequences summarized in Table 3 were identified in respect of these experiments and in relation to the shRNA oligonucleotide sequences outlined in Table 4 herein:

TABLE 3

*Mus musculus* PARP1 Target Sequences

| SEQ ID NO.: | Sequence |
|---|---|
| 11 | GCACTTCATGAAGCTGTATGA |
| 12 | GCACAGTTATCGGCAGTAACA |
| 13 | GGAGGCAAGTTGACAGGATCT |
| 14 | TCGACGTCAACTACGAGAAAC |
| 15 | GCCCTTGGAAACATGTATGAA |

The following *Mus musculus* PARP1 shRNA oligonucleotide sequences summarized in Table 4 were used in these experiments:

TABLE 4

| *Mus musculus* PARP1 shRNA Oligonucleotide Sequences | |
|---|---|
| SEQ ID NO.: | Sequence |
| 16 | GCACTTCATGAAGCTGTATGACTCGAGTCATACAGCTTC ATGAAGTGCTTTTT |
| 17 | GCACAGTTATCGGCAGTAACACTCGAGTGTTACTGCCGA TAACTGTGCTTTTT |
| 18 | GGAGGCAAGTTGACAGGATCTCTCGAGAGATCCTGTCAA CTTGCCTCCTTTTT |
| 19 | TCGACGTCAACTACGAGAAACCTCGAGGTTTCTCGTAGT TGACGTCGATTTTT |
| 20 | GCCCTTGGAAACATGTATGAACTCGAGTTCATACATGTT TCCAAGGGCTTTTT |

The *Homo sapiens* and *Mus musculus* PARP1 shRNA oligonucleotide sequences outlined in this Example were used in conjunction with the lentiviral vector system discussed herein.

An experimental therapeutic vector was designed as shown in FIG. 1A (linear form), and FIGS. 1C and 1D (circularized forms), Referring to the circularized vector map shown in FIGS. 1C and 1D, the experimental therapeutic vector includes: a hybrid 5' long terminal repeat (RSV/5' LTR) (SEQ ID NOS: 21-22), a WV gag (SEQ ID NO: 23), a RRE (Rev-response element) (SEQ ID NO: 24), a Env element (SEQ ID NO: 25), a cPPT (SEQ ID NO: 26), a H1 promoter (SEQ ID NO: 27), a shRNA targeting PARP1 (shPARP1) (SEQ ID NOS: 6-10), a promoter (SEQ ID NO: 28), a GFP element (SEQ ID NO: 29), a Woodchuck Post-Transcriptional Regulatory Element (WPRE) (SEQ ID NO: 30), and a 3' LTR delta U3 (SEQ ID NO: 31). The presence of GFP is for experimental purposes due to its usefulness in demonstrating transduction in in vitro and in vivo model systems.

Further, referring to circularized vector maps shown in FIGS. 1E and 1F, a therapeutic or lentiviral vector has been designed which includes: a hybrid 5' long terminal repeat (RSV/5' LTR) (SEQ ED NOS: 21-22), a HIV gag (SEQ ID NO: 23), a RRE (Rev-response element) (SEQ ID NO: 24), a Env element (SEQ ID NO: 23), a cPPT (SEQ ID NO: 26), a H1 promoter (SEQ ID NO: 27), a shRNA targeting PARP1 (shPARP1. (SEQ ID NOS: 6-10), a Woodchuck Post-Transcriptional Regulator), Element (WPRE) (SEQ ID NO: 30), and a 3' LTR delta U3 (SEQ ID NO: 31). The therapeutic or lentiviral vector detailed in FIGS. 1E and 1F does not contain GFP.

Example 3, shRNA-Mediated Decrease of PARP1 Protein Expression shRNAs designed against *Homo sapiens* PARP1 were tested for their ability to downregulate PARP1 gene expression. The lentiviral vector containing human PAR1 shRNA was packaged as lentiviral particles. Lentiviral particles at a MOI of 1-10 were added to human U251 glioblastoma cells. After 48 hours, cells were lysed and PARP1 expression was measured by immunoblot analysis with a PARP1 specific antibody.

As shown in Table 5 below, five of the shRNAs designed against PARP1 showed an ability to downregulate PARP1 protein expression. Compared to a 100% control shRNA sequence: Sequence 6 (SEQ ID NO: 6) resulted in 57.1% of PARP1 protein expression; Sequence 7 (SEQ ID NO: 7) resulted in 45.8% of PARP1 protein expression; Sequence 8 (SEQ ID NO: 8) resulted in 47.2% of PARR1 protein expression; Sequence 9 (SEQ ID NO: 9) resulted in 48.8% of PARP1 protein expression; and Sequence 10 (SEQ ID NO: 10) resulted in 27.1% of PARP1 protein expression.

TABLE 5

| shRNA-mediated downregulation of *Homo sapiens* PARP1 | |
|---|---|
| shRNA against *Homo sapiens* PARP1 | Percentage protein expression (Control shRNA = 100%) after transduction with lentivirus expressing shRNA |
| Control shRNA Sequence (SEQ ID NO: 61) | 100 |
| Human PARP1 Sequence 6 (SEQ ID NO: 6) | 57.1 |
| Human PARP1 Sequence 7 (SEQ ID NO: 7) | 45.8 |
| Human PARP1 Sequence 8 (SEQ ID NO: 8) | 47.2 |
| Human PARP1 Sequence 9 (SEQ ID NO: 9) | 48.8 |
| Human PARP1 Sequence 10 (SEQ ID NO: 10) | 27.1 |

shRNAs designed against *Mus musculus* PARP1 were tested for their ability to downregulate PARP1 gene expression. The lentiviral vector containing mouse PARP1 sit RNA was packaged as *lenti* viral particles. Lentiviral particles at a MOI of 1-10 was added to mouse Hepa1-6 hepatoma cells. After 48 hours, cells were lysed and PARP1 expression was measured by immunoblot analysis with a PARP1 specific antibody. As shown in Table 6 below, five of the shRNAs designed against PARP1 showed an ability to downregulate PARP1 protein expression. Compared to a. 100% control shRNA sequence: Sequence 16 (SEQ ID NO: 16) resulted in 22.8% of PARP1 protein expression; Sequence 17 (SEQ ID NO: 17) resulted in 47.7% of PARP1 protein expression; Sequence 18 (SEQ ID NO: 18) resulted in 2% of PARP1 protein expression; Sequence 19 (SEQ ID NO:19) resulted in 0.2% of PARP1 protein expression; and Sequence 20 (SEQ ID NO: 20) resulted in 2% of PARP1 protein expression.

TABLE 6

| shRNA-mediated downregulation of *Mus musculus* PARP1 | |
|---|---|
| shRNA against *Mus musculus* PARP1 | Percentage protein expression (Control shRNA = 100%) after transduction with lentivirus expressing shRNA |
| Control shRNA Sequence (SEQ ID NO: 61) | 100 |
| Mouse PARP1 Sequence 16 (SEQ ID NO: 16) | 22.8 |
| Mouse PARP1 Sequence 17 (SEQ ID NO: 17) | 47.7 |
| Mouse PARP1 Sequence 18 (SEQ ID NO: 18) | 2 |
| Mouse PARP1 Sequence 19 (SEQ ID NO: 19) | 0.2 |
| Mouse PARP1 Sequence 20 (SEQ ID NO: 20) | 2 |

Figure 2:
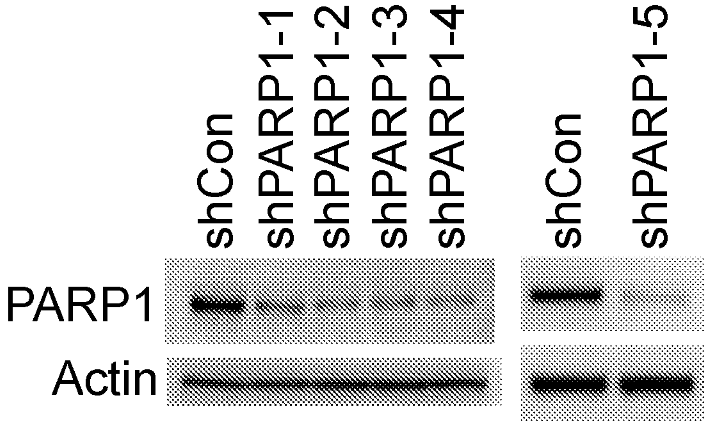
FIG. 2 depicts results from a knockdown experiment involving PARP1 in human cells.

PARP1 protein expression was found to be reduced in human and mouse cells following shRNA administration. Referring first to FIG. 2, a reduction in PARP1 protein in U251 human glioblastoma cell lines is demonstrated following treatment with lentivirus vectors expressing shRNA. The cell line U251 contains measurable PARP1 protein in cell lysates as indicated in the lanes identified as shCon (i.e., a lentivirus vector containing an irrelevant shRNA sequence that does not affect PARP1 protein expression). Individual shRNA sequences 6-10 (as referred to in Table 2 herein) were cloned into lentivirus vectors, expressed as infectious virus particles and used to transduce U251 cells. 48 hours after transduction, cells were lysed, proteins were separated by polyacrylamide gel electrophoresis and detected by immunoblot assay using anti-PARP1 antibody (Cell Signaling Technology).

Still referring to FIG. 2, Sequence 6 corresponds with lane shPARP1-1; Sequence 7 corresponds with lane shPARP1-2; Sequence 8 corresponds with lane shPARP1-3: Sequence 9 corresponds with lane shPARP1-4; and Sequence 10 corresponds with lane shPARP1-5, The housekeeping protein Actin was detected with Anti-Actin antibody (Sigma-Aldrich) to confirm that similar amounts of protein were analyzed in each lane of the gel. Sequence 10 was identified as being the most effective for reducing PARP1 protein in human 0251 cells.

Figure 3:
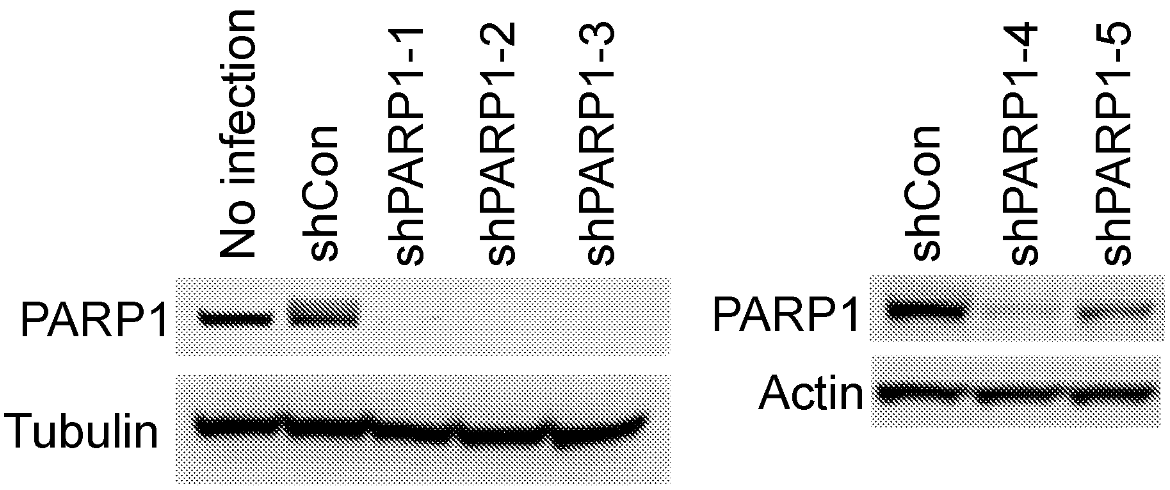
FIG. 3 depicts results from a knockdown experiment involving PARP1 in mouse cells.

Turning to mouse cell experiments, and with reference to FIG. 3, a reduction in PARP1 protein levels in Hepa1-6 mouse hepatoma cells was observed following administration of lentivirus vectors expressing shRNAs. The cell line Hepa1-6 contains measurable PARP1 protein in cell lysates as indicated in, lanes identified as No infection (no lentivirus used) or shCon (lentivirus vector containing an irrelevant shRNA sequence that does not affect PARP1 protein expression). Individual shRNA constructs 16-20 (as referred to in Table 4 herein) were cloned into lentivirus vectors, expressed as infectious virus particles and used to transduce Hepa1-6 cells. 48 hours after transduction, cells were lysed, proteins were separated by polyacrylamide gel electrophoresis and detected by immunoblot assay using anti-PARP1 antibody (Cell Signaling Technology). Still referring to FIG. 3, Sequence 16 corresponds with lane shPARP1-1; Sequence 17 corresponds with lane shPARP1-2; Sequence 18 corresponds with lane shPARP1-3; Sequence 19 corresponds with lane shPARP1-4; and Sequence 20 corresponds with lane shPARP1-5. The housekeeping proteins Actin or Tubulin were detected with antibody reagents (Sigma-Aldrich) as controls for the amount of protein loaded in each lane of the gel. shRNA 16, 17 and 18 were potent for inhibiting PARP1 protein expression. Sequence 1.9 was identified as being most effective for reducing PARP1 protein in murine Hepa1-6.

Example 4. Lentiviral Vector Transduction in Mouse Neurons

Figure 4:
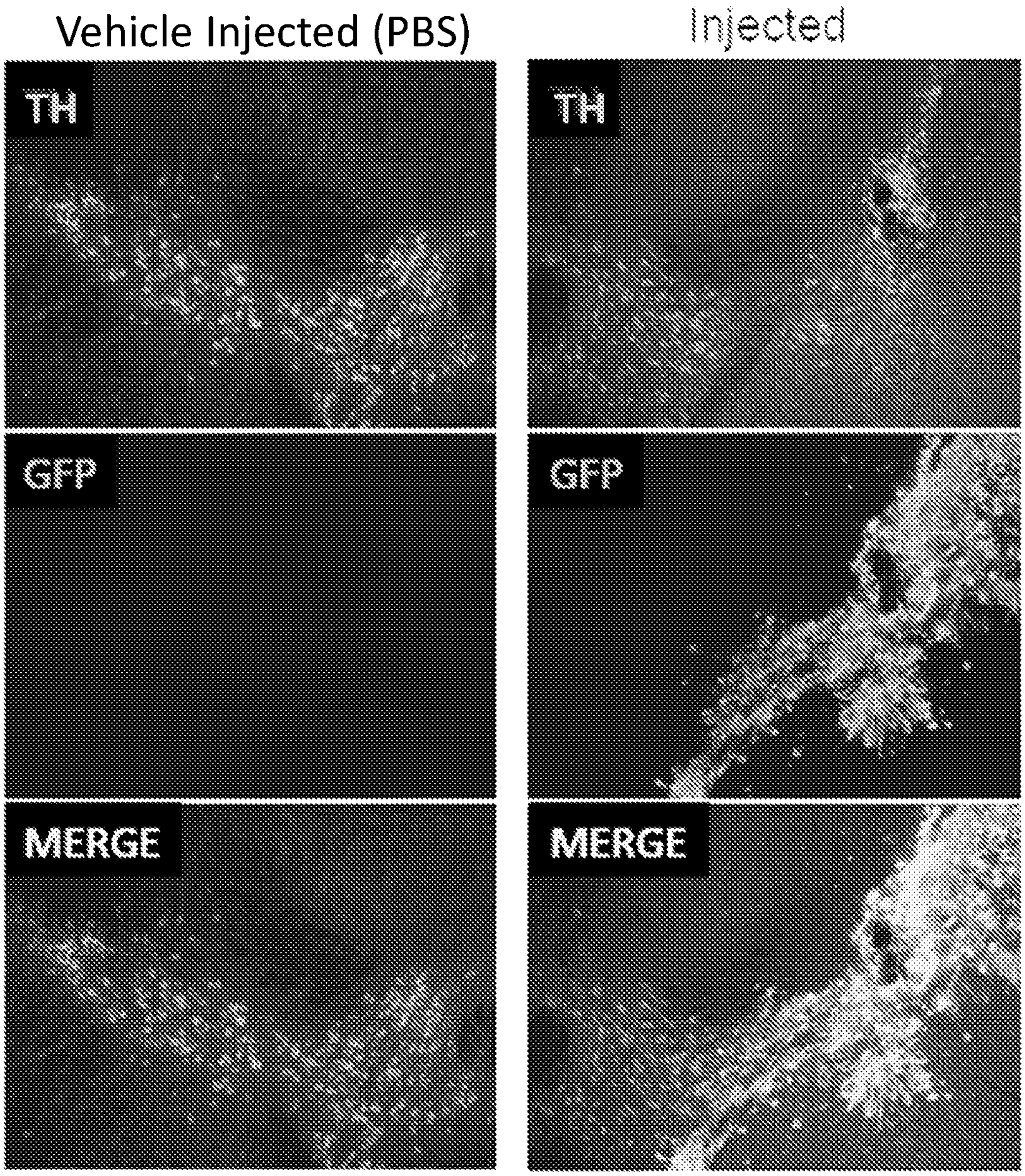
FIG. 4 depicts neurons transduced with an exemplary lentiviral vector.

The lentiviral vector system outlined herein has been found to be capable of transduction in mouse neurons. With reference to FIG. 4, wild-type mice were injected with mock (no lentivirus) in the left column of micrographs or LV-shPARP1 also expressing green fluorescence protein in the right column of micrographs, via a steel needle inserted into the substantia nigra region of the mouse brain. The IN-shPARP1-GFP was dosed at 0.1 ml containing approximately $1 \times 10^8$ transducing units. 14 days later, mice were sacrificed and the substantia nigra region was excised from the brain, fixed in formaldehyde, and embedded in paraffin. Thin sections were mounted on glass slides and visualized with a fluorescence microscope. TH+ neurons (expressing high levels of tyrosine hydroxylase) generally identify the substantia nigra region and appear red (or white in gray-scale photographs) in FIG. 4. The middle panels depict cells that were transduced with mock (left column) or LV-shPARP1-GFP (see: green [or white in gray-scale photographs] staining in right column), Due to the high intensity of light emitted by GFP, indicating efficient transduction and transgene expression, positively transduced neurons appeared black in this figure and were not present, as expected, in the sham control (left column). The lower panels merge the TH+ neuron staining and GFP+ neuron staining from lentivirus transductions to demonstrate the presence of transduced cells within the substantia nigra including within TH+ neurons.

Example 5. Therapeutic Treatment of Neuronal Death Using Lentiviral Vector System The chemical neurotoxin 1-Methyl-4-phenyl-1,2,3,6-tetrahydropyridine (MPTP) causes severe and irreversible motor abnormalities in mice, and is widely used to model human PD. See, e.g., Kopin & Markey, 11 *Annu. Rev. Neurosci,* 81-96 (1988). Treating mice with MPTP lowers the levels of striatal dopamine and its metabolites, because drug neurotoxicity reduces the number of dopamine producing cells in the substantia nigra. The model has been used to test the protective effects of compounds including nitric oxide, which prevent neuronal death after MPTP exposure. See, e.g., Przedborski el al., 93 *Proc. Natl. Acad. Sci. USA.,* 44565-4571 (1996), This model can be employed to measure the potential for preventing death of dopaminergic neurons by pretreating mice with lentivirus vector designed to express a short hairpin RNA sequence (sh) that will reduce neuronal cell expression of PARP (LV-shPARP). The vector can be further modified to express the green fluorescence protein marker that will identify transduced cells (LV-shPARP-GFP) and is compared to a vector that does not express shPARP (LV-GFP).

Suspensions of LV-shPARP-GFP or LV-GFP are injected into the substantia nigra of healthy adult mice. Doses are escalated until a toxic level is reached, which results in severe motor impairment or death of the mouse. Using the maximum tolerated dose, mice are treated with LV-shPARP-GFP or control vector. Two weeks later, sentinel animals from each group are sacrificed to confirm transduction of neurons in the substantia nigra. The remaining animals (in groups of 10) are treated with MPTP-HCl, 20 mg/kg dose in saline given four times via intraperitoneal injection with 2 hour intervals. Between 2 and 7 days later, groups of mice are sacrificed, the brain in removed, fixed and embedded in paraffin for sectioning. The substantia nigra region is identified by staining for tyrosine hydroxylase-expressing 1.0 neurons (TH+) and transduced neurons are identified by expression of GFP. Therapeutic impact of LV-shPARP-GFP is determined by counting the numbers of TH+ or GFP+ neurons in substantia nigra from mice treated with LV-shPARP-GFP or control vector. MPTP is expected to destroy much of the substantia nigra T14+ cells and LV-shPARP-GFP is expected to protect these cells and preserve normal appearance of the substantia nigra. In additional groups of mice treated in the same way with both LV vectors and MPTP, the brains are removed at 7 days after MPTP dosing, the substantia nigra region is isolated by dissection and tissue is frozen at −80 degrees Celsius. Subsequently, the tissue specimens are thawed and dopamine is extracted according to published methods (see: Przedborski of al., infra). LV-shPARP-GFP is expected to preserve normal levels of dopamine production after MPTP treatment, and dopamine levels will be significantly higher in mice treated with LV-shPARP-GFP than mice treated with control vector.

Example 6. Lentiviral Targeting to Neurons Using Variants of Envelope Glycoproteins Properties of individual envelope glycoproteins impact tissue tropism and the efficiency of delivery of therapeutic genes to the sites of disease. To treat PD, a target for gene therapy is a TH+ cell of the substantia nigra. To optimize targeting to a TH+ cell, various envelope glycoproteins will be compared for their role in improving transduction efficiencies in the TH+ cells of the mouse substantia nigra. As described above in Example 1, an envelope plasmid has been designed and produced which contains the vesicular stomatitis virus G glycoprotein (VSV-G). This envelope plasmid can be compared to other designed envelope plasmids which, in place of VSV-G, includes FUG-C (N-terminal region of rabies vines glycoprotein), gp64 envelope glycoprotein from baculovirus, envelope glycoprotein from baboon endogenous virus or other suitable alternatives for packaging lentivirus particles. In each case, using the envelope plasmid variants, lentivirus vector stocks are produced, injected into mouse brains, and the efficiency of transduction into TH+ cells of the mouse substantia nigra is examined.

Example 7. Testing PARP Genes for Therapeutic Effect of PD

The studies described herein include a focus on PARP1 and how its modulation can be used to therapeutically treat PD. However, PARP1 is only 1 of approximately 16 closely related PARP genes with similar functions. Using the techniques for target identification, shRNA production and conversion into lentivirus-delivered miRNA as described herein, the other PARP genes can be tested for their ability to be effective therapeutic vectors in treating PD. Briefly, lentiviral vectors containing the other PARP genes can be injected into a mouse to test for PD correction using the methods, techniques and materials described herein.

Example 8. Method of Designing Synthetic miRNAs for Insertion into a Lentiviral Vector System Target short-hairpin sequences that are 19-22 nucleotides long are chosen from a snRNA design program such as, for example, the invitrogen Block-iT RNAi designer or the RNAi design program from the Broad Institute (MIT). Several sequences are tested for efficient knockdown of a particular gene, such as, for example, PARP. A shRNA sequence that decreases the target gene expression at least 80% is then inserted within a defined microRNA hairpin backbone. MicroRNA (miRNA) hairpin structures can be obtained from the miRBase.org website.

The chosen shRNA sequence is then inserted within the hairpin structure while leaving the loop sequence unchanged. The antisense shRNA sequence is inserted within the 5-prime sequence of the miRNA hairpin to become the seed sequence for gene targeting. The sense shRNA sequence is modified according to the particular miRNA hairpin structure chosen. As an example, nucleotides 9 and 10 of the sense strand are removed for the miR30 hairpin structure. A miR sequence containing a target sequence such as PARP and a backbone sequence are synthesized with BsrGI and Noff restriction sites by either MWG Operon or IDT. This sequence is inserted into the BsrG1 and Notl sites of the miR-acceptor lentiviral vector.

Example 9. Treatment of Human Patients with PD

Twelve patients aged 35-75 years at least 5 years after initial diagnosis of PD receive bilateral, stereotactic, intraputaminal injections of LV-shPARP compositions (based, for example, on the lentiviral construct shown in FIG. 1B) as described herein (cGMP grade) in a dose escalation study. The likely dose range is $10^8$ transducing units of LV-shPARP in 5 ml of sterile saline [1 transducing unit is the amount of LV-shPARP required to achieve on average, 1 copy of the transgene integrated into the chromosome of a single target cell]. The upper range is expected to be approximately $10^{10}$ transducing units of LV-shPARP. Treated patients are followed for at least 1 year and up to 5 years for changes in locomotor status.

Changes in clinical status are determined using the Unified Parkinson's Disease Rating Scale, comparing, LV-treated to off medication status for a matched group of patients with PD. Patients are also asked to record clinical status in terms of time without troubling 1.0 dyskinesia, and may also undergo testing with the Purdue pegboard test of hand dexterity, and activities of daily living score. See, e.g., Marks Jr., et al., 9(12) *Lancet Neurol.,* 1164-72 (2010). Patient outcomes after LV-shPARP therapy are compared to previous gene therapy trials testing Adeno-associated virus delivery of glutamic acid decarboxylase gene or aromatic L-amino acid decarboxylase to increase L-DOPA production or studies using 1.5 Adeno-associated virus delivery of the neurotrophic growth factor neurturin. See, e.g., Kaplitt et al, 369 (9579) *Lancet Neurol:* 2097-105 (2007); see also Christine et al., 73(20) *Neurology,* 1662-9, (2009). It is rationally predicted that subjects receiving LV-shPARP compositions show improvements in PD and PD-related symptoms.

The disclosure of the above example embodiments is intended to be illustrative, but not limiting, of the scope of the inventions, which are set forth in the following claims and their equivalents. Although exemplary embodiments of the inventions have been described in some detail for purposes of clarity of understanding, it will be apparent that certain changes and modifications can be practiced within the scope of the following claims. In the following claims, elements and/or steps do not imply any particular order of operation, unless explicitly stated in the claims or implicitly required by the disclosure.

Sequences

| SEQ ID NO: | Description | Sequence |
|---|---|---|
| 1 | *Homo sapiens* PARP1 Target Sequence 1 | CTTCGTTAGAATGTCTGCCTT |

-continued

Sequences

| SEQ ID NO: | Description | Sequence |
|---|---|---|
| 2 | *Homo sapiens* PARP1 Target Sequence 2 | GCAGCTTCATAACCGAAGATT |
| 3 | *Homo sapiens* PARP1 Target Sequence 3 | CCGAGAAATCTCTTACCTCAA |
| 4 | *Homo sapiens* PARP1 Target Sequence 4 | CGACCTGATCTGGAACATCAA |
| 5 | *Homo sapiens* PARP1 Target Sequence 5 | GTTGCTGATGGGTAGTACC |
| 6 | *Homo sapiens* PARP1 shRNA Oligonucleotide Sequence 1 | CTTCGTTAGAATGTCTGCCTTCTCGAGAAGGCAGACAT TCTAACGAAGTTTTT |
| 7 | *Homo sapiens* PARP1 shRNA Oligonucleotide Sequence 2 | GCAGCTTCATAACCGAAGATTCTCGAGAATCTTCGGTT ATGAAGCTGCTTTTT |
| 8 | *Homo sapiens* PARP1 shRNA Oligonucleotide Sequence 3 | CCGAGAAATCTCTTACCTCAACTCGAGTTGAGGTAAGA GATTTCTCGGTTTTT |
| 9 | *Homo sapiens* PARP1 shRNA Oligonucleotide Sequence 4 | CGACCTGATCTGGAACATCAACTCGAGTTGATGTTCCA GATCAGGTCGTTTTT |
| 10 | *Homo sapiens* PARP1 shRNA Oligonucleotide Sequence 5 | GTTGCTGATGGGTAGTACCTTCAAGAGAGGTACTACCC ATCAGCAACTTTTT |
| 11 | *Mus musculus* PARP1 Target Sequence 1 | GCACTTCATGAAGCTGTATGA |
| 12 | *Mus musculus* PARP1 Target Sequence 2 | GCACAGTTATCGGCAGTAACA |
| 13 | *Mus musculus* PARP1 Target Sequence 3 | GGAGGCAAGTTGACAGGATCT |
| 14 | *Mus musculus* PARP1 Target Sequence 4 | TCGACGTCAACTACGAGAAAC |
| 15 | *Mus musculus* PARP1 Target Sequence 5 | GCCCTTGGAAACATGTATGAA |
| 16 | *Mus musculus* PARP1 shRNA Oligonucleotide Sequence 1 | GCACTTCATGAAGCTGTATGACTCGAGTCATACAGCTT CATGAAGTGCTTTTT |
| 17 | *Mus musculus* PARP1 shRNA Oligonucleotide Sequence 2 | GCACAGTTATCGGCAGTAACACTCGAGTGTTACTGCCG ATAACTGTGCTTTTT |

-continued

Sequences

| SEQ ID NO: | Description | Sequence |
|---|---|---|
| 18 | *Mus musculus* PARP1 shRNA Oligonucleotide Sequence 3 | GGAGGCAAGTTGACAGGATCTCTCGAGAGATCCTGTC AACTTGCCTCCTTTTT |
| 19 | *Mus musculus* PARP1 shRNA Oligonucleotide Sequence 4 | TCGACGTCAACTACGAGAAACCTCGAGGTTTCTCGTAG TTGACGTCGATTTTT |
| 20 | *Mus musculus* PARP1 shRNA Oligonucleotide Sequence 5 | GCCCTTGGAAACATGTATGAACTCGAGTTCATACATGT TTCCAAGGGCTTTTT |
| 21 | *Rous Sarcoma* virus (RSV) promoter | GTAGTCTTATGCAATACTCTTGTAGTCTTGCAACATGGT AACGATGAGTTAGCAACATGCCTTACAAGGAGAGAAA AAGCACCGTGCATGCCGATTGGTGGAAGTAAGGTGGTA CGATCGTGCCTTATTAGGAAGGCAACAGACGGGTCTGA CATGGATTGGACGAACCACTGAATTGCCGCATTGCAGA GATATTGTATTTAAGTGCCTAGCTCGATACAATAAACG |
| 22 | 5' Long terminal repeat (LTR) | GGTCTCTCTGGTTAGACCAGATCTGAGCCTGGGAGCTC TCTGGCTAACTAGGGAACCCACTGCTTAAGCCTCAATA AAGCTTGCCTTGAGTGCTTCAAGTAGTGTGTGCCCGTCT GTTGTGTGACTCTGGTAACTAGAGATCCCTCAGACCCTT TTAGTCAGTGTGGAAAATCTCTAGCA |
| 23 | Helper/Rev; HIV Gag; Viral capsid | ATGGGTGCGAGAGCGTCAGTATTAAGCGGGGGAGAAT TAGATCGATGGGAAAAAATTCGGTTAAGGCCAGGGGG AAAGAAAAAATATAAATTAAAACATATAGTATGGGCA AGCAGGGAGCTAGAACGATTCGCAGTTAATCCTGGCCT GTTAGAAACATCAGAAGGCTGTAGACAAATACTGGGA CAGCTACAACCATCCCTTCAGACAGGATCAGAAGAACT TAGATCATTATATAATACAGTAGCAACCCTCTATTGTGT GCATCAAAGGATAGAGATAAAAGACACCAAGGAAGCT TTAGACAAGATAGAGGAAGAGCAAAACAAAAGTAAGA AAAAAGCACAGCAAGCAGCAGCTGACACAGGACACAG CAATCAGGTCAGCCAAAATTACCCTATAGTGCAGAACA TCCAGGGGCAAATGGTACATCAGGCCATATCACCTAGA ACTTTAAATGCATGGGTAAAAGTAGTAGAAGAGAAGG CTTTCAGCCCAGAAGTGATACCCATGTTTTCAGCATTAT CAGAAGGAGCCACCCCACAAGATTTAAACACCATGCTA AACACAGTGGGGGGACATCAAGCAGCCATGCAAATGT TAAAAGAGACCATCAATGAGGAAGCTGCAGAATGGGA TAGAGTGCATCCAGTGCATGCAGGGCCTATTGCACCAG GCCAGATGAGAGAACCAAGGGGAAGTGACATAGCAGG AACTACTAGTACCCTTCAGGAACAAATAGGATGGATGA CACATAATCCACCTATCCCAGTAGGAGAAATCTATAAA AGATGGATAATCCTGGGATTAAATAAAATAGTAAGAAT GTATAGCCCTACCAGCATTCTGGACATAAGACAAGGAC CAAAGGAACCCTTTAGAGACTATGTAGACCGATTCTAT AAAACTCTAAGAGCCGAGCAAGCTTCACAAGAGGTAA AAAATTGGATGACAGAAACCTTGTTGGTCCAAAATGCG AACCCAGATTGTAAGACTATTTTAAAAGCATTGGGACC AGGAGCGACACTAGAAGAAATGATGACAGCATGTCAG GGAGTGGGGGGACCCGGCCATAAAGCAAGAGTTTTGG CTGAAGCAATGAGCCAAGTAACAAATCCAGCTACCATA ATGATACAGAAAGGCAATTTTAGGAACCAAAGAAAGA CTGTTAAGTGTTTCAATTGTGGCAAAGAAGGGCACATA GCCAAAAATTGCAGGGCCCCTAGGAAAAAGGGCTGTT GGAAATGTGGAAAGGAAGGACACCAAATGAAAGATTG TACTGAGAGACAGGCTAATTTTTTAGGGAAGATCTGGC CTTCCCACAAGGGAAGGCCAGGGAATTTTCTTCAGAGC AGACCAGAGCCAACAGCCCCACCAGAAGAGAGCTTCA GGTTTGGGGAAGAGACAACAACTCCCTCTCAGAAGCAG GAGCCGATAGACAAGGAACTGTATCCTTTAGCTTCCCT CAGATCACTCTTTGGCAGCGACCCCTCGTCACAATAA |

-continued

Sequences

| SEQ ID NO: | Description | Sequence |
|---|---|---|
| 24 | Rev response element (RRE) | AGGAGCTTTGTTCCTTGGGTTCTTGGGAGCAGCAGGAA<br>GCACTATGGGCGCAGCCTCAATGACGCTGACGGTACAG<br>GCCAGACAATTATTGTCTGGTATAGTGCAGCAGCAGAA<br>CAATTTGCTGAGGGCTATTGAGGCGCAACAGCATCTGT<br>TGCAACTCACAGTCTGGGGCATCAAGCAGCTCCAGGCA<br>AGAATCCTGGCTGTGGAAAGATACCTAAAGGATCAACA<br>GCTCC |
| 25 | Envelope; VSV-G; Glycoprotein envelope-cell entry | ATGAAGTGCCTTTTGTACTTAGCCTTTTTATTCATTGGG<br>GTGAATTGCAAGTTCACCATAGTTTTTCCACACAACCA<br>AAAAGGAAACTGGAAAAATGTTCCTTCTAATTACCATT<br>ATTGCCCGTCAAGCTCAGATTTAAATTGGCATAATGAC<br>TTAATAGGCACAGCCTTACAAGTCAAAATGCCCAAGAG<br>TCACAAGGCTATTCAAGCAGACGGTTGGATGTGTCATG<br>CTTCCAAATGGGTCACTACTTGTGATTTCCGCTGGTATG<br>GACCGAAGTATATAACACATTCCATCCGATCCTTCACT<br>CCATCTGTAGAACAATGCAAGGAAAGCATTGAACAAA<br>CGAAACAAGGAACTTGGCTGAATCCAGGCTTCCCTCCT<br>CAAAGTTGTGGATATGCAACTGTGACGGATGCCGAAGC<br>AGTGATTGTCCAGGTGACTCCTCACCATGTGCTGGTTG<br>ATGAATACACAGGAGAATGGGTTGATTCACAGTTCATC<br>AACGGAAAATGCAGCAATTACATATGCCCCACTGTCCA<br>TAACTCTACAACCTGGCATTCTGACTATAAGGTCAAAG<br>GGCTATGTGATTCTAACCTCATTTCCATGGACATCACCT<br>TCTTCTCAGAGGACGGAGAGCTATCATCCCTGGGAAAG<br>GAGGGCACAGGGTTCAGAAGTAACTACTTTGCTTATGA<br>AACTGGAGGCAAGGCCTGCAAAATGCAATACTGCAAG<br>CATTGGGGAGTCAGACTCCCATCAGGTGTCTGGTTCGA<br>GATGGCTGATAAGGATCTCTTTGCTGCAGCCAGATTCC<br>CTGAATGCCCAGAAGGGTCAAGTATCTCTGCTCCATCT<br>CAGACCTCAGTGGATGTAAGTCTAATTCAGGACGTTGA<br>GAGGATCTTGGATTATTCCCTCTGCCAAGAAACCTGGA<br>GCAAAATCAGAGCGGGTCTTCCAATCTCTCCAGTGGAT<br>CTCAGCTATCTTGCTCCTAAAAACCCAGGAACCGGTCC<br>TGCTTTCACCATAATCAATGGTACCCTAAAATACTTTGA<br>GACCAGATACATCAGAGTCGATATTGCTGCTCCAATCC<br>TCTCAAGAATGGTCGGAATGATCAGTGGAACTACCACA<br>GAAAGGGAACTGTGGGATGACTGGGCACCATATGAAG<br>ACGTGGAAATTGGACCCAATGGAGTTCTGAGGACCAGT<br>TCAGGATATAAGTTTCCTTTATACATGATTGGACATGGT<br>ATGTTGGACTCCGATCTTCATCTTAGCTCAAAGGCTCAG<br>GTGTTCGAACATCCTCACATTCAAGACGCTGCTTCGCA<br>ACTTCCTGATGATGAGAGTTTATTTTTTGGTGATACTGG<br>GCTATCCAAAAATCCAATCGAGCTTGTAGAAGGTTGGT<br>TCAGTAGTTGGAAAAGCTCTATTGCCTCTTTTTTCTTTA<br>TCATAGGGTTAATCATTGGACTATTCTTGGTTCTCCGAG<br>TTGGTATCCATCTTTGCATTAAATTAAAGCACACCAAG<br>AAAAGACAGATTTATACAGACATAGAGATGA |
| 26 | Central polypurine tract (cPPT) | TTTTAAAAGAAAAGGGGGGATTGGGGGGTACAGTGCA<br>GGGGAAAGAATAGTAGACATAATAGCAACAGACATAC<br>AAACTAAAGAATTACAAAAACAAATTACAAAATTCAA<br>AATTTTA |
| 27 | Polymerase III shRNA promoters; H1 promoter | GAACGCTGACGTCATCAACCCGCTCCAAGGAATCGCGG<br>GCCCAGTGTCACTAGGCGGGAACACCCAGCGCGCGTGC<br>GCCCTGGCAGGAAGATGGCTGTGAGGGACAGGGGAGT<br>GGCGCCCTGCAATATTTGCATGTCGCTATGTGTTCTGGG<br>AAATCACCATAAACGTGAAATGTCTTTGGATTTGGGAA<br>TCTTATAAGTTCTGTATGAGACCACTT |
| 28 | EF1 | GCTCCGGTGCCCGTCAGTGGGCAGAGCGCACATCGCCC<br>ACAGTCCCCGAGAAGTTGGGGGGAGGGGTCGGCAATT<br>GAACGGGTGCCTAGAGAAGGTGGCGCGGGGTAAACTG<br>GGAAAGTGATGTCGTGTACTGGCTCCGCCTTTTTCCCGA<br>GGGTGGGGGAGAACCGTATATAAGTGCAGTAGTCGCC<br>GTGAACGTTCTTTTTCGCAACGGGTTTGCCGCCAGAAC<br>ACAGCTGAAGCTTCGAGGGGCTCGCATCTCTCCTTCAC<br>GCGCCCGCCGCCCTACCTGAGGCCGCCATCCACGCCGG<br>TTGAGTCGCGTTCTGCCGCCTCCCGCCTGTGGTGCCTCC<br>TGAACTGCGTCCGCCGTCTAGGTAAGTTTAAAGCTCAG |

-continued

| Sequences | |
|---|---|
| SEQ ID NO: Description | Sequence |
| | GTCGAGACCGGGCCTTTGTCCGGCGCTCCCTTGGAGCC<br>TACCTAGACTCAGCCGGCTCTCCACGCTTTGCCTGACCC<br>TGCTTGCTCAACTCTACGTCTTTGTTTCGTTTTCTGTTCT<br>GCGCCGTTACAGATCCAAGCTGTGACCGGCGCCTAC |
| 29 GFP | ATGGAGAGCGACGAGAGCGGCCTGCCCGCCATGGAGA<br>TCGAGTGCCGCATCACCGGCACCCTGAACGGCGTGGAG<br>TTCGAGCTGGTGGGCGGCGGAGAGGGCACCCCCAAGC<br>AGGGCCGCATGACCAACAAGATGAAGAGCACCAAAGG<br>CGCCCTGACCTTCAGCCCCTACCTGCTGAGCCACGTGA<br>TGGGCTACGGCTTCTACCACTTCGGCACCTACCCCAGC<br>GGCTACGAGAACCCCTTCCTGCACGCCATCAACAACGG<br>CGGCTACACCAACACCCGCATCGAGAAGTACGAGGAC<br>GGCGGCGTGCTGCACGTGAGCTTCAGCTACCGCTACGA<br>GGCCGGCCGCGTGATCGGCGACTTCAAGGTGGTGGGCA<br>CCGGCTTCCCCGAGGACAGCGTGATCTTCACCGACAAG<br>ATCATCCGCAGCAACGCCACCGTGGAGCACCTGCACCC<br>CATGGGCGATAACGTGCTGGTGGGCAGCTTCGCCCGCA<br>CCTTCAGCCTGCGCGACGGCGGCTACTACAGCTTCGTG<br>GTGGACAGCCACATGCACTTCAAGAGCGCCATCCACCC<br>CAGCATCCTGCAGAACGGGGGCCCCATGTTCGCCTTCC<br>GCCGCGTGGAGGAGCTGCACAGCAACACCGAGCTGGG<br>CATCGTGGAGTACCAGCACGCCTTCAAGACCCCCATCG<br>CCTTCGCCAGATCCCGCGCTCAGTCGTCCAATTCTGCCG<br>TGGACGGCACCGCCGGACCCGGCTCCACCGGATCTCGC<br>TAA |
| 30 Long WPRE sequence | AATCAACCTCTGATTACAAAATTTGTGAAAGATTGACT<br>GGTATTCTTAACTATGTTGCTCCTTTTACGCTATGTGGA<br>TACGCTGCTTTAATGCCTTTGTATCATGCTATTGCTTCC<br>CGTATGGCTTTCATTTTCTCCTCCTTGTATAAATCCTGG<br>TTGCTGTCTCTTTATGAGGAGTTGTGGCCCGTTGTCAGG<br>CAACGTGGCGTGGTGTGCACTGTGTTTGCTGACGCAAC<br>CCCCACTGGTTGGGGCATTGCCACCACCTGTCAGCTCCT<br>TTCCGGGACTTTCGCTTTCCCCCTCCCTATTGCCACGGC<br>GGAACTCATCGCCGCCTGCCTTGCCCGCTGCTGGACAG<br>GGGCTCGGCTGTTGGGCACTGACAATTCCGTGGTGTTG<br>TCGGGGAAATCATCGTCCTTTCCTTGGCTGCTCGCCTGT<br>GTTGCCACCTGGATTCTGCGCGGGACGTCCTTCTGCTAC<br>GTCCCTTCGGCCCTCAATCCAGCGGACCTTCCTTCCCGC<br>GGCCTGCTGCCGGCTCTGCGGCCTCTTCCGCGTCTTCGC<br>CTTCGCCCTCAGACGAGTCGGATCTCCCTTTGGGCCGCC<br>TCCCCGCCT |
| 31 3' delta LTR | TGGAAGGGCTAATTCACTCCCAACGAAGATAAGATCTG<br>CTTTTTGCTTGTACTGGGTCTCTCTGGTTAGACCAGATC<br>TGAGCCTGGGAGCTCTCTGGCTAACTAGGGAACCCACT<br>GCTTAAGCCTCAATAAAGCTTGCCTTGAGTGCTTCAAG<br>TAGTGTGTGCCCGTCTGTTGTGTGACTCTGGTAACTAGA<br>GATCCCTCAGACCCTTTTAGTCAGTGTGGAAAATCTCTA<br>GCAGTAGTAGTTCATGTCA |
| 32 Helper/Rev; CMV early (CAG) enhancer; Enhance Transcription | TAGTTATTAATAGTAATCAATTACGGGGTCATTAGTTCA<br>TAGCCCATATATGGAGTTCCGCGTTACATAACTTACGG<br>TAAATGGCCCGCCTGGCTGACCGCCCAACGACCCCCGC<br>CCATTGACGTCAATAATGACGTATGTTCCCATAGTAAC<br>GCCAATAGGGACTTTCCATTGACGTCAATGGGTGGACT<br>ATTTACGGTAAACTGCCCACTTGGCAGTACATCAAGTG<br>TATCATATGCCAAGTACGCCCCCTATTGACGTCAATGA<br>CGGTAAATGGCCCGCCTGGCATTATGCCCAGTACATGA<br>CCTTATGGGACTTTCCTACTTGGCAGTACATCTACGTAT<br>TAGTCATC |
| 33 Helper/Rev; Chicken beta actin (CAG) promoter; Transcription | GCTATTACCATGGGTCGAGGTGAGCCCCACGTTCTGCT<br>TCACTCTCCCCATCTCCCCCCCCTCCCCACCCCCAATTT<br>TGTATTTATTTATTTTTTAATTATTTTGTGCAGCGATGG<br>GGGCGGGGGGGGGGGGGCGCGCGCCAGGCGGGGCGG<br>GGCGGGGCGAGGGGCGGGGCGGGGCGAGGCGGAGAG<br>GTGCGGCGGCAGCCAATCAGAGCGGCGCGCTCCGAAA<br>GTTTCCTTTTATGGCGAGGCGGCGGCGGCGGCGGCCCT<br>ATAAAAAGCGAAGCGCGCGGCGGGCG |

-continued

| SEQ ID NO: | Description | Sequence |
|---|---|---|
| Sequences | | |
| 34 | Helper/Rev; Chicken beta actin intron; Enhance gene expression | GGAGTCGCTGCGTTGCCTTCGCCCCGTGCCCCGCTCCGC<br>GCCGCCTCGCGCCGCCCGCCCCGGCTCTGACTGACCGC<br>GTTACTCCCACAGGTGAGCGGGCGGGACGGCCCTTCTC<br>CTCCGGGCTGTAATTAGCGCTTGGTTTAATGACGGCTC<br>GTTTCTTTTCTGTGGCTGCGTGAAAGCCTTAAAGGGCTC<br>CGGGAGGGCCCTTTGTGCGGGGGGGAGCGGCTCGGGG<br>GGTGCGTGCGTGTGTGTGTGCGTGGGGAGCGCCGCGTG<br>CGGCCCGCGCTGCCCGGCGGCTGTGAGCGCTGCGGGCG<br>CGGCGCGGGGCTTTGTGCGCTCCGCGTGTGCGCGAGGG<br>GAGCGCGGCCGGGGGCGGTGCCCCGCGGTGCGGGGGG<br>GCTGCGAGGGGAACAAAGGCTGCGTGCGGGGTGTGTG<br>CGTGGGGGGGTGAGCAGGGGGTGTGGGCGCGGCGGTC<br>GGGCTGTAACCCCCCCCTGCACCCCCCTCCCCGAGTTG<br>CTGAGCACGGCCCGGCTTCGGGTGCGGGGCTCCGTGCG<br>GGGCGTGGCGCGGGGCTCGCCGTGCCGGGCGGGGGGT<br>GGCGGCAGGTGGGGGTGCCGGGCGGGGCGGGGCCGCC<br>TCGGGCCGGGGAGGGCTCGGGGGAGGGGCGCGGCGGC<br>CCCGGAGCGCCGGCGGCTGTCGAGGCGCGGCGAGCCG<br>CAGCCATTGCCTTTTATGGTAATCGTGCGAGAGGGCGC<br>AGGGACTTCCTTTGTCCCAAATCTGGCGGAGCCGAAAT<br>CTGGGAGGCGCCGCCGCACCCCCTCTAGCGGGCGCGGG<br>CGAAGCGGTGCGGCGCCGGCAGGAAGGAAATGGGCGG<br>GGAGGGCCTTCGTGCGTCGCCGCGCCGCCGTCCCCTTC<br>TCCATCTCCAGCCTCGGGGCTGCCGCAGGGGGACGGCT<br>GCCTTCGGGGGGGACGGGGCAGGGCGGGGTTCGGCTTC<br>TGGCGTGTGACCGGCGG |
| 35 | Helper/Rev; HIV Pol; Protease and reverse transcriptase | ATGAATTTGCCAGGAAGATGGAAACCAAAAATGATAG<br>GGGGAATTGGAGGTTTTATCAAAGTAGGACAGTATGAT<br>CAGATACTCATAGAAATCTGCGGACATAAAGCTATAGG<br>TACAGTATTAGTAGGACCTACACCTGTCAACATAATTG<br>GAAGAAATCTGTTGACTCAGATTGGCTGCACTTTAAAT<br>TTTCCCATTAGTCCTATTGAGACTGTACCAGTAAAATTA<br>AAGCCAGGAATGGATGGCCCAAAAGTTAAACAATGGC<br>CATTGACAGAAGAAAAAATAAAAGCATTAGTAGAAAT<br>TTGTACAGAAATGGAAAAGGAAGGAAAAATTTCAAAA<br>ATTGGGCCTGAAAATCCATACAATACTCCAGTATTTGC<br>CATAAAGAAAAAAGACAGTACTAAATGGAGAAAATTA<br>GTAGATTTCAGAGAACTTAATAAGAGAACTCAAGATTT<br>CTGGGAAGTTCAATTAGGAATACCACATCCTGCAGGGT<br>TAAAACAGAAAAAATCAGTAACAGTACTGGATGTGGG<br>CGATGCATATTTTTCAGTTCCCTTAGATAAAGACTTCAG<br>GAAGTATACTGCATTTACCATACCTAGTATAAACAATG<br>AGACACCAGGGATTAGATATCAGTACAATGTGCTTCCA<br>CAGGGATGGAAAGGATCACCAGCAATATTCCAGTGTAG<br>CATGACAAAAATCTTAGAGCCTTTTAGAAAACAAAATC<br>CAGACATAGTCATCTATCAATACATGGATGATTTGTAT<br>GTAGGATCTGACTTAGAAATAGGGCAGCATAGAACAA<br>AAATAGAGGAACTGAGACAACATCTGTTGAGGTGGGG<br>ATTTACCACACCAGACAAAAAACATCAGAAAGAACCTC<br>CATTCCTTTGGATGGGTTATGAACTCCATCCTGATAAAT<br>GGACAGTACAGCCTATAGTGCTGCCAGAAAAGGACAG<br>CTGGACTGTCAATGACATACAGAAATTAGTGGGAAAAT<br>TGAATTGGGCAAGTCAGATTTATGCAGGGATTAAAGTA<br>AGGCAATTATGTAAACTTCTTAGGGGAACCAAAGCACT<br>AACAGAAGTAGTACCACTAACAGAAGAAGCAGAGCTA<br>GAACTGGCAGAAAACAGGGAGATTCTAAAAGAACCGG<br>TACATGGAGTGTATTATGACCCATCAAAAGACTTAATA<br>GCAGAAATACAGAAGCAGGGGCAAGGCCAATGGACAT<br>ATCAAATTTATCAAGAGCCATTTAAAAATCTGAAAACA<br>GGAAAATATGCAAGAATGAAGGGTGCCCACACTAATG<br>ATGTGAAACAATTAACAGAGGCAGTACAAAAAATAGC<br>CACAGAAAGCATAGTAATATGGGGAAAGACTCCTAAA<br>TTTAAATTACCCATACAAAAGGAAACATGGGAAGCATG<br>GTGGACAGAGTATTGGCAAGCCACCTGGATTCCTGAGT<br>GGGAGTTTGTCAATACCCCTCCCTTAGTGAAGTTATGGT<br>ACCAGTTAGAGAAAGAACCCATAATAGGAGCAGAAAC<br>TTTCTATGTAGATGGGGCAGCCAATAGGGAAACTAAAT<br>TAGGAAAAGCAGGATATGTAACTGACAGAGGAAGACA<br>AAAAGTTGTCCCCCTAACGGACACAACAAATCAGAAG<br>ACTGAGTTACAAGCAATTCATCTAGCTTTGCAGGATTC<br>GGGATTAGAAGTAAACATAGTGACAGACTCACAATATG |

-continued

| SEQ ID NO: | Description | Sequence |
|---|---|---|
| | | CATTGGGAATCATTCAAGCACAACCAGATAAGAGTGAA<br>TCAGAGTTAGTCAGTCAAATAATAGAGCAGTTAATAAA<br>AAAGGAAAAAGTCTACCTGGCATGGGTACCAGCACAC<br>AAAGGAATTGGAGGAAATGAACAAGTAGATGGGTTGG<br>TCAGTGCTGGAATCAGGAAAGTACTA |
| 36 | Helper Rev; HIV Integrase; Integration of viral RNA | TTTTTAGATGGAATAGATAAGGCCCAAGAAGAACATGA<br>GAAATATCACAGTAATTGGAGAGCAATGGCTAGTGATT<br>TTAACCTACCACCTGTAGTAGCAAAAGAAATAGTAGCC<br>AGCTGTGATAAATGTCAGCTAAAAGGGGAAGCCATGC<br>ATGGACAAGTAGACTGTAGCCCAGGAATATGGCAGCTA<br>GATTGTACACATTTAGAAGGAAAAGTTATCTTGGTAGC<br>AGTTCATGTAGCCAGTGGATATATAGAAGCAGAAGTAA<br>TTCCAGCAGAGACAGGGCAAGAAACAGCATACTTCCTC<br>TTAAAATTAGCAGGAAGATGGCCAGTAAAAACAGTAC<br>ATACAGACAATGGCAGCAATTTCACCAGTACTACAGTT<br>AAGGCCGCCTGTTGGTGGGCGGGGATCAAGCAGGAATT<br>TGGCATTCCCTACAATCCCCAAAGTCAAGGAGTAATAG<br>AATCTATGAATAAAGAATTAAAGAAAATTATAGGACA<br>GGTAAGAGATCAGGCTGAACATCTTAAGACAGCAGTAC<br>AAATGGCAGTATTCATCCACAATTTTAAAAGAAAAGGG<br>GGGATTGGGGGGTACAGTGCAGGGGAAAGAATAGTAG<br>ACATAATAGCAACAGACATACAAACTAAAGAATTACA<br>AAAACAAATTACAAAAATTCAAAATTTTCGGGTTTATT<br>ACAGGGACAGCAGAGATCCAGTTTGGAAAGGACCAGC<br>AAAGCTCCTCTGGAAAGGTGAAGGGGCAGTAGTAATA<br>CAAGATAATAGTGACATAAAAGTAGTGCCAAGAAGAA<br>AAGCAAAGATCATCAGGGATTATGGAAAACAGATGGC<br>AGGTGATGATTGTGTGGCAAGTAGACAGGATGAGGATT<br>AA |
| 37 | Helper/Rev; HIV Rev; Nuclear export and stabilize viral mRNA | ATGGCAGGAAGAAGCGGAGACAGCGACGAAGAACTCC<br>TCAAGGCAGTCAGACTCATCAAGTTTCTCTATCAAAGC<br>AACCCACCTCCCAATCCCGAGGGGACCCGACAGGCCCG<br>AAGGAATAGAAGAAGAAGGTGGAGAGAGAGACAGAG<br>ACAGATCCATTCGATTAGTGAACGGATCCTTAGCACTT<br>ATCTGGGACGATCTGCGGAGCCTGTGCCTCTTCAGCTA<br>CCACCGCTTGAGAGACTTACTCTTGATTGTAACGAGGA<br>TTGTGGAACTTCTGGGACGCAGGGGGTGGGAAGCCCTC<br>AAATATTGGTGGAATCTCCTACAATATTGGAGTCAGGA<br>GCTAAAGAATAG |
| 38 | Helper/Rev; Rabbit beta globin poly A; RNA stability | AGATCTTTTTCCCTCTGCCAAAAATTATGGGGACATCAT<br>GAAGCCCCTTGAGCATCTGACTTCTGGCTAATAAAGGA<br>AATTTATTTTCATTGCAATAGTGTGTTGGAATTTTTTGT<br>GTCTCTCACTCGGAAGGACATATGGGAGGGCAAATCAT<br>TTAAAACATCAGAATGAGTATTTGGTTTAGAGTTTGGC<br>AACATATGCCATATGCTGGCTGCCATGAACAAAGGTGG<br>CTATAAAGAGGTCATCAGTATATGAAACAGCCCCCTGC<br>TGTCCATTCCTTATTCCATAGAAAAGCCTTGACTTGAGG<br>TTAGATTTTTTTTATATTTTGTTTTGTGTTATTTTTTTCTT<br>TAACATCCCTAAAATTTTCCTTACATGTTTTACTAGCCA<br>GATTTTTCCTCCTCTCCTGACTACTCCCAGTCATAGCTG<br>TCCCTCTTCTCTTATGAAGATC |
| 39 | Envelope; CMV promoter; Transcription | ACATTGATTATTGACTAGTTATTAATAGTAATCAATTAC<br>GGGGTCATTAGTTCATAGCCCATATATGGAGTTCCGCG<br>TTACATAACTTACGGTAAATGGCCCGCCTGGCTGACCG<br>CCCAACGACCCCCGCCCATTGACGTCAATAATGACGTA<br>TGTTCCCATAGTAACGCCAATAGGGACTTTCCATTGAC<br>GTCAATGGGTGGAGTATTTACGGTAAACTGCCCACTTG<br>GCAGTACATCAAGTGTATCATATGCCAAGTACGCCCCC<br>TATTGACGTCAATGACGGTAAATGGCCCGCCTGGCATT<br>ATGCCCAGTACATGACCTTATGGGACTTTCCTACTTGGC<br>AGTACATCTACGTATTAGTCATCGCTATTACCATGGTGA<br>TGCGGTTTTGGCAGTACATCAATGGGCGTGGATAGCGG<br>TTTGACTCACGGGGATTTCCAAGTCTCCACCCCATTGAC<br>GTCAATGGGAGTTTGTTTTGGCACCAAAATCAACGGGA<br>CTTTCCAAAATGTCGTAACAACTCCGCCCCATTGACGC<br>AAATGGGCGGTAGGCGTGTACGGTGGGAGGTCTATATA<br>AGC |

-continued

| SEQ ID NO: | Description | Sequence |
|---|---|---|
| 40 | Envelope; Beta globin intron; Enhance gene expression | GTGAGTTTGGGGACCCTTGATTGTTCTTTCTTTTTCGCT ATTGTAAAATTCATGTTATATGGAGGGGGCAAAGTTTT CAGGGTGTTGTTTAGAATGGGAAGATGTCCCTTGTATC ACCATGGACCCTCATGATAATTTTGTTTCTTTCACTTTC TACTCTGTTGACAACCATTGTCTCCTCTTATTTTCTTTTC ATTTTCTGTAACTTTTTCGTTAAACTTTAGCTTGCATTTG TAACGAATTTTTAAATTCACTTTTGTTTATTTGTCAGAT TGTAAGTACTTTCTCTAATCACTTTTTTTTCAAGGCAAT CAGGGTATATTATATTGTACTTCAGCACAGTTTTAGAG AACAATTGTTATAATTAAATGATAAGGTAGAATATTTC TGCATATAAATTCTGGCTGGCGTGGAAATATTCTTATTG GTAGAAACAACTACACCCTGGTCATCATCCTGCCTTTCT CTTTATGGTTACAATGATATACACTGTTTGAGATGAGG ATAAAATACTCTGAGTCCAAACCGGGCCCCTCTGCTAA CCATGTTCATGCCTTCTTCTCTTTCCTACAG |
| 41 | Primer | TAAGCAGAATTCATGAATTTGCCAGGAAGAT |
| 42 | Primer | CCATACAATGAATGGACACTAGGCGGCCGCACGAAT |
| 43 | Gag, Pol, Integrase fragment | GAATTCATGAATTTGCCAGGAAGATGGAAACCAAAAAT GATAGGGGGAATTGGAGGTTTTATCAAAGTAAGACAGT ATGATCAGATACTCATAGAAATCTGCGGACATAAAGCT ATAGGTACAGTATTAGTAGGACCTACACCTGTCAACAT AATTGGAAGAAATCTGTTGACTCAGATTGGCTGCACTT TAAATTTTCCCATTAGTCCTATTGAGACTGTACCAGTAA AATTAAAGCCAGGAATGGATGGCCCAAAAGTTAAACA ATGGCCATTGACAGAAGAAAAAATAAAAGCATTAGTA GAAATTTGTACAGAAATGGAAAAGGAAGGAAAAATTT CAAAAATTGGGCCTGAAAATCCATACAATACTCCAGTA TTTGCCATAAAGAAAAAAGACAGTACTAAATGGAGAA AATTAGTAGATTTCAGAGAACTTAATAAGAGAACTCAA GATTTCTGGGAAGTTCAATTAGGAATACCACATCCTGC AGGGTTAAAACAGAAAAAATCAGTAACAGTACTGGAT GTGGGCGATGCATATTTTTCAGTTCCCTTAGATAAAGA CTTCAGGAAGTATACTGCATTTACCATACCTAGTATAA ACAATGAGACACCAGGGATTAGATATCAGTACAATGTG CTTCCACAGGGATGGAAAGGATCACCAGCAATATTCCA GTGTAGCATGACAAAAATCTTAGAGCCTTTTAGAAAAC AAAATCCAGACATAGTCATCTATCAATACATGGATGAT TTGTATGTAGGATCTGACTTAGAAATAGGGCAGCATAG AACAAAAATAGAGGAACTGAGACAACATCTGTTGAGG TGGGGATTTACCACACCAGACAAAAAACATCAGAAAG AACCTCCATTCCTTTGGATGGGTTATGAACTCCATCCTG ATAAATGGACAGTACAGCCTATAGTGCTGCCAGAAAAG GACAGCTGGACTGTCAATGACATACAGAAATTAGTGGG AAAATTGAATTGGGCAAGTCAGATTTATGCAGGGATTA AAGTAAGGCAATTATGTAAACTTCTTAGGGGAACCAAA GCACTAACAGAAGTAGTACCACTAACAGAAGAAGCAG AGCTAGAACTGGCAGAAAACAGGGAGATTCTAAAAGA ACCGGTACATGGAGTGTATTATGACCCATCAAAAGACT TAATAGCAGAAATACAGAAGCAGGGGCAAGGCCAATG GACATATCAAATTTATCAAGAGCCATTTAAAAATCTGA AAACAGGAAAGTATGCAAGAATGAAGGGTGCCCACAC TAATGATGTGAAACAATTAACAGAGGCAGTACAAAAA ATAGCCACAGAAAGCATAGTAATATGGGGAAAGACTC CTAAATTTAAATTACCCATACAAAAGGAAACATGGGAA GCATGGTGGACAGAGTATTGGCAAGCCACCTGGATTCC TGAGTGGGAGTTTGTCAATACCCCTCCCTTAGTGAAGTT ATGGTACCAGTTAGAGAAAGAACCCATAATAGGAGCA GAAACTTTCTATGTAGATGGGGCAGCCAATAGGGAAAC TAAATTAGGAAAAGCAGGATATGTAACTGACAGAGGA AGACAAAAAGTTGTCCCCCTAACGGACACAACAAATCA GAAGACTGAGTTACAAGCAATTCATCTAGCTTTGCAGG ATTCGGGATTAGAAGTAAACATAGTGACAGACTCACAA TATGCATTGGGAATCATTCAAGCACAACCAGATAAGAG TGAATCAGAGTTAGTCAGTCAAATAATAGAGCAGTTAA TAAAAAAGGAAAAAGTCTACCTGGCATGGGTACCAGC ACACAAAGGAATTGGAGGAAATGAACAAGTAGATAAA TTGGTCAGTGCTGGAATCAGGAAAGTACTATTTTTAGA TGGAATAGATAAGGCCCAAGAAGAACATGAGAAATAT CACAGTAATTGGAGAGCAATGGCTAGTGATTTTAACCT |

-continued

| SEQ ID NO: Description | Sequence |
|---|---|
| | ACCACCTGTAGTAGCAAAAGAAATAGTAGCCAGCTGTG<br>ATAAATGTCAGCTAAAAGGGGAAGCCATGCATGGACA<br>AGTAGACTGTAGCCCAGGAATATGGCAGCTAGATTGTA<br>CACATTTAGAAGGAAAAGTTATCTTGGTAGCAGTTCAT<br>GTAGCCAGTGGATATATAGAAGCAGAAGTAATTCCAGC<br>AGAGACAGGGCAAGAAACAGCATACTTCCTCTTAAAAT<br>TAGCAGGAAGATGGCCAGTAAAAACAGTACATACAGA<br>CAATGGCAGCAATTTCACCAGTACTACAGTTAAGGCCG<br>CCTGTTGGTGGGCGGGGATCAAGCAGGAATTTGGCATT<br>CCCTACAATCCCCAAAGTCAAGGAGTAATAGAATCTAT<br>GAATAAAGAATTAAAGAAAATTATAGGACAGGTAAGA<br>GATCAGGCTGAACATCTTAAGACAGCAGTACAAATGGC<br>AGTATTCATCCACAATTTTAAAAGAAAAGGGGGGATTG<br>GGGGGTACAGTGCAGGGGAAAGAATAGTAGACATAAT<br>AGCAACAGACATACAAACTAAAGAATTACAAAAACAA<br>ATTACAAAAATTCAAAATTTTCGGGTTTATTACAGGGA<br>CAGCAGAGATCCAGTTTGGAAAGGACCAGCAAAGCTC<br>CTCTGGAAAGGTGAAGGGGCAGTAGTAATACAAGATA<br>ATAGTGACATAAAAGTAGTGCCAAGAAGAAAAGCAAA<br>GATCATCAGGGATTATGGAAAACAGATGGCAGGTGAT<br>GATTGTGTGGCAAGTAGACAGGATGAGGATTAA |
| 44 DNA Fragment containing Rev, RRE and rabbit beta globin poly A | TCTAGAATGGCAGGAAGAAGCGGAGACAGCGACGAAG<br>AGCTCATCAGAACAGTCAGACTCATCAAGCTTCTCTAT<br>CAAAGCAACCCACCTCCCAATCCCGAGGGGACCCGACA<br>GGCCCGAAGGAATAGAAGAAGAAGGTGGAGAGAGAG<br>ACAGAGACAGATCCATTCGATTAGTGAACGGATCCTTG<br>GCACTTATCTGGGACGATCTGCGGAGCCTGTGCCTCTTC<br>AGCTACCACCGCTTGAGAGACTTACTCTTGATTGTAAC<br>GAGGATTGTGGAACTTCTGGGACGCAGGGGGTGGGAA<br>GCCCTCAAATATTGGTGGAATCTCCTACAATATTGGAG<br>TCAGGAGCTAAAGAATAGAGGAGCTTTGTTCCTTGGGT<br>TCTTGGGAGCAGCAGGAAGCACTATGGGCGCAGCGTCA<br>ATGACGCTGACGGTACAGGCCAGACAATTATTGTCTGG<br>TATAGTGCAGCAGCAGAACAATTTGCTGAGGGCTATTG<br>AGGCGCAACAGCATCTGTTGCAACTCACAGTCTGGGGC<br>ATCAAGCAGCTCCAGGCAAGAATCCTGGCTGTGGAAAG<br>ATACCTAAAGGATCAACAGCTCCTAGATCTTTTTCCCTC<br>TGCCAAAAATTATGGGGACATCATGAAGCCCCTTGAGC<br>ATCTGACTTCTGGCTAATAAAGGAAATTTATTTTCATTG<br>CAATAGTGTGTTGGAATTTTTTGTGTCTCTCACTCGGAA<br>GGACATATGGGAGGGCAAATCATTTAAAACATCAGAAT<br>GAGTATTTGGTTTAGAGTTTGGCAACATATGCCATATG<br>CTGGCTGCCATGAACAAAGGTGGCTATAAAGAGGTCAT<br>CAGTATATGAAACAGCCCCCTGCTGTCCATTCCTTATTC<br>CATAGAAAAGCCTTGACTTGAGGTTAGATTTTTTTTATA<br>TTTTGTTTTGTGTTATTTTTTTCTTTAACATCCCTAAAAT<br>TTTCCTTACATGTTTTACTAGCCAGATTTTTCCTCCTCTC<br>CTGACTACTCCCAGTCATAGCTGTCCCTCTTCTCTTATG<br>AAGATCCCTCGACCTGCAGCCCAAGCTTGGCGTAATCA<br>TGGTCATAGCTGTTTCCTGTGTGAAATTGTTATCCGCTC<br>ACAATTCCACACAACATACGAGCCGGAAGCATAAAGT<br>GTAAAGCCTGGGGTGCCTAATGAGTGAGCTAACTCACA<br>TTAATTGCGTTGCGCTCACTGCCCGCTTTCCAGTCGGGA<br>AACCTGTCGTGCCAGCGGATCCGCATCTCAATTAGTCA<br>GCAACCATAGTCCCGCCCCTAACTCCGCCCATCCCGCC<br>CCTAACTCCGCCCAGTTCCGCCCATTCTCCGCCCCATGG<br>CTGACTAATTTTTTTTATTTATGCAGAGGCCGAGGCCGC<br>CTCGGCCTCTGAGCTATTCCAGAAGTAGTGAGGAGGCT<br>TTTTTGGAGGCCTAGGCTTTTGCAAAAAGCTAACTTGTT<br>TATTGCAGCTTATAATGGTTACAAATAAAGCAATAGCA<br>TCACAAATTTCACAAATAAAGCATTTTTTTCACTGCATT<br>CTAGTTGTGGTTTGTCCAAACTCATCAATGTATCTTATC<br>AGCGGCCGCCCCGGG |
| 45 DNA fragment containing the CAG enhancer/promoter/ intron sequence | ACGCGTTAGTTATTAATAGTAATCAATTACGGGGTCAT<br>TAGTTCATAGCCCATATATGGAGTTCCGCGTTACATAA<br>CTTACGGTAAATGGCCCGCCTGGCTGACCGCCCAACGA<br>CCCCCGCCCATTGACGTCAATAATGACGTATGTTCCCAT<br>AGTAACGCCAATAGGGACTTTCCATTGACGTCAATGGG<br>TGGACTATTTACGGTAAACTGCCCACTTGGCAGTACAT<br>CAAGTGTATCATATGCCAAGTACGCCCCCTATTGACGT<br>CAATGACGGTAAATGGCCCGCCTGGCATTATGCCCAGT |

-continued

Sequences

| SEQ ID NO: Description | Sequence |
| --- | --- |
| | ACATGACCTTATGGGACTTTCCTACTTGGCAGTACATCT<br>ACGTATTAGTCATCGCTATTACCATGGGTCGAGGTGAG<br>CCCCACGTTCTGCTTCACTCTCCCCATCTCCCCCCCCTC<br>CCCACCCCCAATTTTGTATTTATTTATTTTTTAATTATTT<br>TGTGCAGCGATGGGGGCGGGGGGGGGGGGGGCGCGCG<br>CCAGGCGGGGCGGGGCGGGGCGAGGGGCGGGGCGGGG<br>CGAGGCGGAGAGGTGCGGCGGCAGCCAATCAGAGCGG<br>CGCGCTCCGAAAGTTTCCTTTTATGGCGAGGCGGCGGC<br>GGCGGCGGCCCTATAAAAAGCGAAGCGCGCGGCGGGC<br>GGGAGTCGCTGCGTTGCCTTCGCCCCGTGCCCCGCTCC<br>GCGCCGCCTCGCGCCGCCCGCCCCGGCTCTGACTGACC<br>GCGTTACTCCCACAGGTGAGCGGGCGGGACGGCCCTTC<br>TCCTCCGGGCTGTAATTAGCGCTTGGTTTAATGACGGCT<br>CGTTTCTTTTCTGTGGCTGCGTGAAAGCCTTAAAGGGCT<br>CCGGGAGGGCCCTTTGTGCGGGGGGGAGCGGCTCGGG<br>GGGTGCGTGCGTGTGTGTGTGCGTGGGGAGCGCCGCGT<br>GCGGCCCGCGCTGCCCGGCGGCTGTGAGCGCTGCGGGC<br>GCGGCGCGGGGCTTTGTGCGCTCCGCGTGTGCGCGAGG<br>GGAGCGCGGCCGGGGGCGGTGCCCCGCGGTGCGGGGG<br>GGCTGCGAGGGGAACAAAGGCTGCGTGCGGGGTGTGT<br>GCGTGGGGGGGTGAGCAGGGGGTGTGGGCGCGGCGGT<br>CGGGCTGTAACCCCCCCCTGCACCCCCCTCCCCGAGTT<br>GCTGAGCACGGCCCGGCTTCGGGTGCGGGGCTCCGTGC<br>GGGGCGTGGCGCGGGGCTCGCCGTGCCGGGCGGGGGG<br>TGGCGGCAGGTGGGGGTGCCGGGCGGGGCGGGGCCGC<br>CTCGGGCCGGGGAGGGCTCGGGGGAGGGGCGCGGCGG<br>CCCCGGAGCGCCGGCGGCTGTCGAGGCGCGGCGAGCC<br>GCAGCCATTGCCTTTTATGGTAATCGTGCGAGAGGGCG<br>CAGGGACTTCCTTTGTCCCAAATCTGGCGGAGCCGAAA<br>TCTGGGAGGCGCCGCCGCACCCCCTCTAGCGGGCGCGG<br>GCGAAGCGGTGCGGCGCCGGCAGGAAGGAAATGGGCG<br>GGGAGGGCCTTCGTGCGTCGCCGCGCCGCCGTCCCCTT<br>CTCCATCTCCAGCCTCGGGGCTGCCGCAGGGGGACGGC<br>TGCCTTCGGGGGGGACGGGGCAGGGCGGGGTTCGGCTT<br>CTGGCGTGTGACCGGCGGGAATTC |
| 46 DNA fragment containing VSV-G | GAATTCATGAAGTGCCTTTTGTACTTAGCCTTTTTATTC<br>ATTGGGGTGAATTGCAAGTTCACCATAGTTTTTCCACAC<br>AACCAAAAAGGAAACTGGAAAAATGTTCCTTCTAATTA<br>CCATTATTGCCCGTCAAGCTCAGATTTAAATTGGCATA<br>ATGACTTAATAGGCACAGCCTTACAAGTCAAAATGCCC<br>AAGAGTCACAAGGCTATTCAAGCAGACGGTTGGATGTG<br>TCATGCTTCCAAATGGGTCACTACTTGTGATTTCCGCTG<br>GTATGGACCGAAGTATATAACACATTCCATCCGATCCT<br>TCACTCCATCTGTAGAACAATGCAAGGAAAGCATTGAA<br>CAAACGAAACAAGGAACTTGGCTGAATCCAGGCTTCCC<br>TCCTCAAAGTTGTGGATATGCAACTGTGACGGATGCCG<br>AAGCAGTGATTGTCCAGGTGACTCCTCACCATGTGCTG<br>GTTGATGAATACACAGGAGAATGGGTTGATTCACAGTT<br>CATCAACGGAAAATGCAGCAATTACATATGCCCCACTG<br>TCCATAACTCTACAACCTGGCATTCTGACTATAAGGTC<br>AAAGGGCTATGTGATTCTAACCTCATTTCCATGGACAT<br>CACCTTCTTCTCAGAGGACGGAGAGCTATCATCCCTGG<br>GAAAGGAGGGCACAGGGTTCAGAAGTAACTACTTTGCT<br>TATGAAACTGGAGGCAAGGCCTGCAAAATGCAATACTG<br>CAAGCATTGGGGAGTCAGACTCCCATCAGGTGTCTGGT<br>TCGAGATGGCTGATAAGGATCTCTTTGCTGCAGCCAGA<br>TTCCCTGAATGCCCAGAAGGGTCAAGTATCTCTGCTCC<br>ATCTCAGACCTCAGTGGATGTAAGTCTAATTCAGGACG<br>TTGAGAGGATCTTGGATTATTCCCTCTGCCAAGAAACC<br>TGGAGCAAAATCAGAGCGGGTCTTCCAATCTCTCCAGT<br>GGATCTCAGCTATCTTGCTCCTAAAAACCCAGGAACCG<br>GTCCTGCTTTCACCATAATCAATGGTACCCTAAAATACT<br>TTGAGACCAGATACATCAGAGTCGATATTGCTGCTCCA<br>ATCCTCTCAAGAATGGTCGGAATGATCAGTGGAACTAC<br>CACAGAAAGGGAACTGTGGGATGACTGGGCACCATAT<br>GAAGACGTGGAAATTGGACCCAATGGAGTTCTGAGGA<br>CCAGTTCAGGATATAAGTTTCCTTTATACATGATTGGAC<br>ATGGTATGTTGGACTCCGATCTTCATCTTAGCTCAAAGG<br>CTCAGGTGTTCGAACATCCTCACATTCAAGACGCTGCTT<br>CGCAACTTCCTGATGATGAGAGTTTATTTTTTGGTGATA<br>CTGGGCTATCCAAAAATCCAATCGAGCTTGTAGAAGGT<br>TGGTTCAGTAGTTGGAAAAGCTCTATTGCCTCTTTTTTC |

-continued

| SEQ ID NO: | Description | Sequence |
|---|---|---|
| | | TTTATCATAGGGTTAATCATTGGACTATTCTTGGTTCTC CGAGTTGGTATCCATCTTTGCATTAAATTAAAGCACAC CAAGAAAAGACAGATTTATACAGACATAGAGATGAGA ATTC |
| 47 | Rev; RSV promoter; Transcription | ATGGCAGGAAGAAGCGGAGACAGCGACGAAGAACTCC TCAAGGCAGTCAGACTCATCAAGTTTCTCTATCAAAGC AACCCACCTCCCAATCCCGAGGGGACCCGACAGGCCCG AAGGAATAGAAGAAGAAGGTGGAGAGAGAGACAGAG ACAGATCCATTCGATTAGTGAACGGATCCTTAGCACTT ATCTGGGACGATCTGCGGAGCCTGTGCCTCTTCAGCTA CCACCGCTTGAGAGACTTACTCTTGATTGTAACGAGGA TTGTGGAACTTCTGGGACGCAGGGGGTGGGAAGCCCTC AAATATTGGTGGAATCTCCTACAATATTGGAGTCAGGA GCTAAAGAATAG |
| 48 | RSV promoter and HIV Rev | CAATTGCGATGTACGGGCCAGATATACGCGTATCTGAG GGGACTAGGGTGTGTTTAGGCGAAAAGCGGGGCTTCGG TTGTACGCGGTTAGGAGTCCCCTCAGGATATAGTAGTT TCGCTTTTGCATAGGGAGGGGGAAATGTAGTCTTATGC AATACACTTGTAGTCTTGCAACATGGTAACGATGAGTT AGCAACATGCCTTACAAGGAGAGAAAAAGCACCGTGC ATGCCGATTGGTGGAAGTAAGGTGGTACGATCGTGCCT TATTAGGAAGGCAACAGACAGGTCTGACATGGATTGGA CGAACCACTGAATTCCGCATTGCAGAGATAATTGTATT TAAGTGCCTAGCTCGATACAATAAACGCCATTTGACCA TTCACCACATTGGTGTGCACCTCCAAGCTCGAGCTCGTT TAGTGAACCGTCAGATCGCCTGGAGACGCCATCCACGC TGTTTTGACCTCCATAGAAGACACCGGGACCGATCCAG CCTCCCCTCGAAGCTAGCGATTAGGCATCTCCTATGGC AGGAAGAAGCGGAGACAGCGACGAAGAACTCCTCAAG GCAGTCAGACTCATCAAGTTTCTCTATCAAAGCAACCC ACCTCCCAATCCCGAGGGGACCCGACAGGCCCGAAGG AATAGAAGAAGAAGGTGGAGAGAGAGACAGAGACAG ATCCATTCGATTAGTGAACGGATCCTTAGCACTTATCTG GGACGATCTGCGGAGCCTGTGCCTCTTCAGCTACCACC GCTTGAGAGACTTACTCTTGATTGTAACGAGGATTGTG GAACTTCTGGGACGCAGGGGGTGGGAAGCCCTCAAAT ATTGGTGGAATCTCCTACAATATTGGAGTCAGGAGCTA AAGAATAGTCTAGA |
| 49 | Promoter; PGK | GGGGTTGGGGTTGCGCCTTTTCCAAGGCAGCCCTGGGT TTGCGCAGGGACGCGGCTGCTCTGGGCGTGGTTCCGGG AAACGCAGCGGCGCCGACCCTGGGTCTCGCACATTCTT CACGTCCGTTCGCAGCGTCACCCGGATCTTCGCCGCTA CCCTTGTGGGCCCCCCGGCGACGCTTCCTGCTCCGCCCC TAAGTCGGGAAGGTTCCTTGCGGTTCGCGGCGTGCCGG ACGTGACAAACGGAAGCCGCACGTCTCACTAGTACCCT CGCAGACGGACAGCGCCAGGGAGCAATGGCAGCGCGC CGACCGCGATGGGCTGTGGCCAATAGCGGCTGCTCAGC AGGGCGCGCCGAGAGCAGCGGCCGGGAAGGGGCGGTG CGGGAGGCGGGGTGTGGGGCGGTAGTGTGGGCCCTGTT CCTGCCCGCGCGGTGTTCCGCATTCTGCAAGCCTCCGG AGCGCACGTCGGCAGTCGGCTCCCTCGTTGACCGAATC ACCGACCTCTCTCCCCAG |
| 50 | Promoter; UbC | GCGCCGGGTTTTGGCGCCTCCCGCGGGCGCCCCCCTCC TCACGGCGAGCGCTGCCACGTCAGACGAAGGGCGCAG GAGCGTTCCTGATCCTTCCGCCCGGACGCTCAGGACAG CGGCCCGCTGCTCATAAGACTCGGCCTTAGAACCCCAG TATCAGCAGAAGGACATTTTAGGACGGGACTTGGGTGA CTCTAGGGCACTGGTTTTCTTTCCAGAGAGCGGAACAG GCGAGGAAAAGTAGTCCCTTCTCGGCGATTCTGCGGAG GGATCTCCGTGGGGCGGTGAACGCCGATGATTATATAA GGACGCGCCGGGTGTGGCACAGCTAGTTCCGTCGCAGC CGGGATTTGGGTCGCGGTTCTTGTTTGTGGATCGCTGTG ATCGTCACTTGGTGAGTTGCGGGCTGCTGGGCTGGCCG GGGCTTTCGTGGCCGCCGGGCCGCTCGGTGGGACGGAA GCGTGTGGAGAGACCGCCAAGGGCTGTAGTCTGGGTCC GCGAGCAAGGTTGCCCTGAACTGGGGGTTGGGGGGAG CGCACAAAATGGCGGCTGTTCCCGAGTCTTGAATGGAA GACGCTTGTAAGGCGGGCTGTGAGGTCGTTGAAACAAG GTGGGGGGCATGGTGGGCGGCAAGAACCCAAGGTCTT |

-continued

| SEQ ID NO: | Description | Sequence |
|---|---|---|
| | | GAGGCCTTCGCTAATGCGGGAAAGCTCTTATTCGGGTG AGATGGGCTGGGGCACCATCTGGGGACCCTGACGTGAA GTTTGTCACTGACTGGAGAACTCGGGTTTGTCGTCTGGT TGCGGGGGCGGCAGTTATGCGGTGCCGTTGGGCAGTGC ACCCGTACCTTTGGGAGCGCGCGCCTCGTCGTGTCGTG ACGTCACCCGTTCTGTTGGCTTATAATGCAGGGTGGGG CCACCTGCCGGTAGGTGTGCGGTAGGCTTTTCTCCGTCG CAGGACGCAGGGTTCGGGCCTAGGGTAGGCTCTCCTGA ATCGACAGGCGCCGGACCTCTGGTGAGGGGAGGGATA AGTGAGGCGTCAGTTTCTTTGGTCGGTTTTATGTACCTA TCTTCTTAAGTAGCTGAAGCTCCGGTTTTGAACTATGCG CTCGGGGTTGGCGAGTGTGTTTTGTGAAGTTTTTTAGGC ACCTTTTGAAATGTAATCATTTGGGTCAATATGTAATTT TCAGTGTTAGACTAGTAAA |
| 51 | Poly A; SV40 | GTTTATTGCAGCTTATAATGGTTACAAATAAAGCAATA GCATCACAAATTTCACAAATAAAGCATTTTTTTCACTGC ATTCTAGTTGTGGTTTGTCCAAACTCATCAATGTATCTT ATCA |
| 52 | Poly A; bGH | GACTGTGCCTTCTAGTTGCCAGCCATCTGTTGTTTGCCC CTCCCCCGTGCCTTCCTTGACCCTGGAAGGTGCCACTCC CACTGTCCTTTCCTAATAAAATGAGGAAATTGCATCGC ATTGTCTGAGTAGGTGTCATTCTATTCTGGGGGGTGGG GTGGGGCAGGACAGCAAGGGGGAGGATTGGGAAGACA ATAGCAGGCATGCTGGGGATGCGGTGGGCTCTATGG |
| 53 | Envelope; RD114 | ATGAAACTCCCAACAGGAATGGTCATTTTATGTAGCCT AATAATAGTTCGGGCAGGGTTTGACGACCCCCGCAAGG CTATCGCATTAGTACAAAAACAACATGGTAAACCATGC GAATGCAGCGGAGGGCAGGTATCCGAGGCCCCACCGA ACTCCATCCAACAGGTAACTTGCCCAGGCAAGACGGCC TACTTAATGACCAACCAAAAATGGAAATGCAGAGTCAC TCCAAAAAATCTCACCCCTAGCGGGGGAGAACTCCAGA ACTGCCCCTGTAACACTTTCCAGGACTCGATGCACAGT TCTTGTTATACTGAATACCGGCAATGCAGGGCGAATAA TAAGACATACTACACGGCCACCTTGCTTAAAATACGGT CTGGGAGCCTCAACGAGGTACAGATATTACAAAACCCC AATCAGCTCCTACAGTCCCCTTGTAGGGGCTCTATAAA TCAGCCCGTTTGCTGGAGTGCCACAGCCCCCATCCATA TCTCCGATGGTGGAGGACCCCTCGATACTAAGAGAGTG TGGACAGTCCAAAAAAGGCTAGAACAAATTCATAAGG CTATGCATCCTGAACTTCAATACCACCCCTTAGCCCTGC CCAAAGTCAGAGATGACCTTAGCCTTGATGCACGGACT TTTGATATCCTGAATACCACTTTTAGGTTACTCCAGATG TCCAATTTTAGCCTTGCCCAAGATTGTTGGCTCTGTTTA AAACTAGGTACCCCTACCCCTCTTGCGATACCCACTCCC TCTTTAACCTACTCCCTAGCAGACTCCCTAGCGAATGCC TCCTGTCAGATTATACCTCCCCTCTTGGTTCAACCGATG CAGTTCTCCAACTCGTCCTGTTTATCTTCCCCTTTCATTA ACGATACGGAACAAATAGACTTAGGTGCAGTCACCTTT ACTAACTGCACCTCTGTAGCCAATGTCAGTAGTCCTTTA TGTGCCCTAAACGGGTCAGTCTTCCTCTGTGGAAATAA CATGGCATACACCTATTTACCCCAAAACTGGACAGGAC TTTGCGTCCAAGCCTCCCTCCTCCCCGACATTGACATCA TCCCGGGGGATGAGCCAGTCCCCATTCCTGCCATTGAT CATTATATACATAGACCTAAACGAGCTGTACAGTTCAT CCCTTTACTAGCTGGACTGGGAATCACCGCAGCATTCA CCACCGGAGCTACAGGCCTAGGTGTCTCCGTCACCCAG TATACAAAATTATCCCATCAGTTAATATCTGATGTCCAA GTCTTATCCGGTACCATACAAGATTTACAAGACCAGGT AGACTCGTTAGCTGAAGTAGTTCTCCAAAATAGGAGGG GACTGGACCTACTAACGGCAGAACAAGGAGGAATTTGT TTAGCCTTACAAGAAAAATGCTGTTTTTATGCTAACAA GTCAGGAATTGTGAGAAACAAAATAAGAACCCTACAA GAAGAATTACAAAAACGCAGGGAAAGCCTGGCATCCA ACCCTCTCTGGACCGGGCTGCAGGGCTTTCTTCCGTACC TCCTACCTCTCCTGGGACCCCTACTCACCCTCCTACTCA TACTAACCATTGGGCCATGCGTTTTCAATCGATTGGTCC AATTTGTTAAAGACAGGATCTCAGTGGTCCAGGCTCTG GTTTTGACTCAGCAATATCACCAGCTAAAACCCATAGA GTACGAGCCATGA |

-continued

Sequences

| SEQ ID NO: | Description | Sequence |
|---|---|---|
| 54 | Envelope; GALV | ATGCTTCTCACCTCAAGCCCGCACCACCTTCGGCACCA<br>GATGAGTCCTGGGAGCTGGAAAAGACTGATCATCCTCT<br>TAAGCTGCGTATTCGGAGACGGCAAAACGAGTCTGCA<br>GAATAAGAACCCCCACCAGCCTGTGACCCTCACCTGGC<br>AGGTACTGTCCCAAACTGGGGACGTTGTCTGGGACAAA<br>AAGGCAGTCCAGCCCCTTTGGACTTGGTGGCCCTCTCT<br>TACACCTGATGTATGTGCCCTGGCGGCCGGTCTTGAGT<br>CCTGGGATATCCCGGGATCCGATGTATCGTCCTCTAAA<br>AGAGTTAGACCTCCTGATTCAGACTATACTGCCGCTTA<br>TAAGCAAATCACCTGGGGAGCCATAGGGTGCAGCTAC<br>CCTCGGGCTAGGACCAGGATGGCAAATTCCCCCTTCTA<br>CGTGTGTCCCCGAGCTGGCCGAACCCATTCAGAAGCTA<br>GGAGGTGTGGGGGGCTAGAATCCCTATACTGTAAAGA<br>ATGGAGTTGTGAGACCACGGGTACCGTTTATTGGCAAC<br>CCAAGTCCTCATGGGACCTCATAACTGTAAAATGGGAC<br>CAAAATGTGAAATGGGAGCAAAAATTTCAAAAGTGTG<br>AACAAACCGGCTGGTGTAACCCCCTCAAGATAGACTTC<br>ACAGAAAAAGGAAAACTCTCCAGAGATTGGATAACGG<br>AAAAAACCTGGGAATTAAGGTTCTATGTATATGGACAC<br>CCAGGCATACAGTTGACTATCCGCTTAGAGGTCACTAA<br>CATGCCGGTTGTGGCAGTGGGCCCAGACCCTGTCCTTG<br>CGGAACAGGGACCTCCTAGCAAGCCCCTCACTCTCCCT<br>CTCTCCCCACGGAAAGCGCCGCCCACCCCTCTACCCCC<br>GGCGGCTAGTGAGCAAACCCCTGCGGTGCATGGAGAA<br>ACTGTTACCCTAAACTCTCCGCCTCCCACCAGTGGCGA<br>CCGACTCTTTGGCCTTGTGCAGGGGGCCTTCCTAACCTT<br>GAATGCTACCAACCCAGGGGCCACTAAGTCTTGCTGGC<br>TCTGTTTGGGCATGAGCCCCCCTTATTATGAAGGGATA<br>GCCTCTTCAGGAGAGGTCGCTTATACCTCCAACCATAC<br>CCGATGCCACTGGGGGGCCCAAGGAAAGCTTACCCTCA<br>CTGAGGTCTCCGGACTCGGGTCATGCATAGGGAAGGTG<br>CCTCTTACCCATCAACATCTTTGCAACCAGACCTTACCC<br>ATCAATTCCTCTAAAAACCATCAGTATCTGCTCCCCTCA<br>AACCATAGCTGGTGGGCCTGCAGCACTGGCCTCACCCC<br>CTGCCTCTCCACCTCAGTTTTTAATCAGTCTAAAGACTT<br>CTGTGTCCAGGTCCAGCTGATCCCCCGCATCTATTACC<br>ATTCTGAAGAAACCTTGTTACAAGCCTATGACAAATCA<br>CCCCCCAGGTTTAAAAGAGAGCCTGCCTCACTTACCCT<br>AGCTGTCTTCCTGGGGTTAGGGATTGCGGCAGGTATAG<br>GTACTGGCTCAACCGCCCTAATTAAAGGGCCCATAGAC<br>CTCCAGCAAGGCCTAACCAGCCTCCAAATCGCCATTGA<br>CGCTGACCTCCGGGCCCTTCAGGACTCAATCAGCAAGC<br>TAGAGGACTCACTGACTTCCCTATCTGAGGTAGTACTC<br>CAAAATAGGAGAGGCCTTGACTTACTATTCCTTAAAGA<br>AGGAGGCCTCTGCGCGGCCCTAAAAGAAGAGTGCTGTT<br>TTTATGTAGACCACTCAGGTGCAGTACGAGACTCCATG<br>AAAAAACTTAAAGAAAGACTAGATAAAAGACAGTTAG<br>AGCGCCAGAAAAACCAAAACTGGTATGAAGGGTGGTT<br>CAATAACTCCCCTTGGTTTACTACCCTACTATCAACCAT<br>CGCTGGGCCCCTATTGCTCCTCCTTTTGTTACTCACTCT<br>TGGGCCCTGCATCATCAATAAATTAATCCAATTCATCA<br>ATGATAGGATAAGTGCAGTCAAAATTTTAGTCCTTAGA<br>CAGAAATATCAGACCCTAGATAACGAGGAAAACCTTT<br>AA |
| 55 | Envelope; FUG | ATGGTTCCGCAGGTTCTTTTGTTTGTACTCCTTCTGGGT<br>TTTTCGTTGTGTTTCGGGAAGTTCCCCATTTACACGATA<br>CCAGACGAACTTGGTCCCTGGAGCCCTATTGACATACA<br>CCATCTCAGCTGTCCAAATAACCTGGTTGTGGAGGATG<br>AAGGATGTACCAACCTGTCCGAGTTCTCCTACATGGAA<br>CTCAAAGTGGGATACATCTCAGCCATCAAAGTGAACGG<br>GTTCACTTGCACAGGTGTTGTGACAGAGGCAGAGACCT<br>ACACCAACTTTGTTGGTTATGTCACAACCACATTCAAG<br>AGAAAGCATTTCCGCCCCACCCCAGACGCATGTAGAGC<br>CGCGTATAACTGGAAGATGGCCGGTGACCCCAGATATG<br>AAGAGTCCCTACACAATCCATACCCCGACTACCACTGG<br>CTTCGAACTGTAAGAACCACCAAAGAGTCCCTCATTAT<br>CATATCCCCAAGTGTGACAGATTTGGACCCATATGACA<br>AATCCCTTCACTCAAGGGTCTTCCCTGGCGGAAAGTGC<br>TCAGGAATAACGGTGTCCTCTACCTACTGCTCAACTAA<br>CCATGATTACACCATTTGGATGCCCGAGAATCCGAGAC<br>CAAGGACACCTTGTGACATTTTTACCAATAGCAGAGGG<br>AAGAGAGCATCCAACGGGAACAAGACTTGCGGCTTTG |

-continued

| Sequences | |
|---|---|
| SEQ ID NO:Description | Sequence |
| | TGGATGAAAGAGGCCTGTATAAGTCTCTAAAAGGAGC ATGCAGGCTCAAGTTATGTGGAGTTCTTGGACTTAGAC TTATGGATGGAACATGGGTCGCGATGCAAACATCAGAT GAGACCAAATGGTGCCCTCCAGATCAGTTGGTGAATTT GCACGACTTTCGCTCAGACGAGATCGAGCATCTCGTTG TGGAGGAGTTAGTTAAGAAAAGAGAGGAATGTCTGGA TGCATTAGAGTCCATCATGACCACCAAGTCAGTAAGTT TCAGACGTCTCAGTCACCTGAGAAAACTTGTCCCAGGG TTTGGAAAAGCATATACCATATTCAACAAAACCTTGAT GGAGGCTGATGCTCACTACAAGTCAGTCCGGACCTGGA ATGAGATCATCCCCTCAAAAGGGTGTTTGAAAGTTGGA GGAAGGTGCCATCCTCATGTGAACGGGGTGTTTTTCAA TGGTATAATATTAGGGCCTGACGACCATGTCCTAATCC CAGAGATGCAATCATCCCTCCTCCAGCAACATATGGAG TTGTTGGAATCTTCAGTTATCCCCCTGATGCACCCCCTG GCAGACCCTTCTACAGTTTTCAAAGAAGGTGATGAGGC TGAGGATTTTGTTGAAGTTCACCTCCCCGATGTGTACA AACAGATCTCAGGGGTTGACCTGGGTCTCCCGAACTGG GGAAAGTATGTATTGATGACTGCAGGGGCCATGATTGG CCTGGTGTTGATATTTTCCCTAATGACATGGTGCAGAG TTGGTATCCATCTTTGCATTAAATTAAAGCACACCAAG AAAAGACAGATTTATACAGACATAGAGATGAACCGAC TTGGAAAGTAA |
| 56 Envelope; LCMV | ATGGGTCAGATTGTGACAATGTTTGAGGCTCTGCCTCA CATCATCGATGAGGTGATCAACATTGTCATTATTGTGC TTATCGTGATCACGGGTATCAAGGCTGTCTACAATTTT GCCACCTGTGGGATATTCGCATTGATCAGTTTCCTACTT CTGGCTGGCAGGTCCTGTGGCATGTACGGTCTTAAGGG ACCCGACATTTACAAAGGAGTTTACCAATTTAAGTCAG TGGAGTTTGATATGTCACATCTGAACCTGACCATGCCC AACGCATGTTCAGCCAACAACTCCCACCATTACATCAG TATGGGGACTTCTGGACTAGAATTGACCTTCACCAATG ATTCCATCATCAGTCACAACTTTTGCAATCTGACCTCTG CCTTCAACAAAAAGACCTTTGACCACACACTCATGAGT ATAGTTTCGAGCCTACACCTCAGTATCAGAGGGAACTC CAACTATAAGGCAGTATCCTGCGACTTCAACAATGGCA TAACCATCCAATACAACTTGACATTCTCAGATCGACAA AGTGCTCAGAGCCAGTGTAGAACCTTCAGAGGTAGAGT CCTAGATATGTTTAGAACTGCCTTCGGGGGGAAATACA TGAGGAGTGGCTGGGGCTGGACAGGCTCAGATGGCAA GACCACCTGGTGTAGCCAGACGAGTTACCAATACCTGA TTATACAAAATAGAACCTGGGAAAACCACTGCACATAT GCAGGTCCTTTTGGGATGTCCAGGATTCTCCTTTCCCAA GAGAAGACTAAGTTCTTCACTAGGAGACTAGCGGGCA CATTCACCTGGACTTTGTCAGACTCTTCAGGGGTGGAG AATCCAGGTGGTTATTGCCTGACCAAATGGATGATTCT TGCTGCAGAGCTTAAGTGTTTCGGGAACACAGCAGTTG CGAAATGCAATGTAAATCATGATGCCGAATTCTGTGAC ATGCTGCGACTAATTGACTACAACAAGGCTGCTTTGAG TAAGTTCAAAGAGGACGTAGAATCTGCCTTGCACTTAT TCAAAACAACAGTGAATTCTTTGATTTCAGATCAACTA CTGATGAGGAACCACTTGAGAGATCTGATGGGGGTGCC ATATTGCAATTACTCAAAGTTTTGGTACCTAGAACATG CAAAGACCGGCGAAACTAGTGTCCCCAAGTGCTGGCTT GTCACCAATGGTTCTTACTTAAATGAGACCCACTTCAG TGATCAAATCGAACAGGAAGCCGATAACATGATTACA GAGATGTTGAGGAAGGATTACATAAAGAGGCAGGGGA GTACCCCCCTAGCATTGATGGACCTTCTGATGTTTTCCA CATCTGCATATCTAGTCAGCATCTTCCTGCACCTTGTCA AAATACCAACACACAGGCACATAAAAGGTGGCTCATG TCCAAAGCCACACCGATTAACCAACAAAGGAATTTGTA GTTGTGGTGCATTTAAGGTGCCTGGTGTAAAAACCGTC TGGAAAAGACGCTGA |
| 57 Envelope; FPV | ATGAACACTCAAATCCTGGTTTTCGCCCTTGTGGCAGT CATCCCCACAAATGCAGACAAAATTTGTCTTGGACATC ATGCTGTATCAAATGGCACCAAAGTAAACACACTCACT GAGAGAGGAGTAGAAGTTGTCAATGCAACGGAAACAG TGGAGCGGACAAACATCCCCAAAATTTGCTCAAAAGG GAAAAGAACCACTGATCTTGGCCAATGCGGACTGTTAG GGACCATTACCGGACCACCTCAATGCGACCAATTTCTA GAATTTTCAGCTGATCTAATAATCGAGAGACGAGAAGG |

| SEQ ID NO: Description | Sequence |
|---|---|
| | AAATGATGTTTGTTACCCGGGGAAGTTTGTTAATGAAG<br>AGGCATTGCGACAAATCCTCAGAGGATCAGGTGGGATT<br>GACAAAGAAACAATGGGATTCACATATAGTGGAATAA<br>GGACCAACGGAACAACTAGTGCATGTAGAAGATCAGG<br>GTCTTCATTCTATGCAGAAATGGAGTGGCTCCTGTCAA<br>ATACAGACAATGCTGCTTTCCCACAAATGACAAAATCA<br>TACAAAAACACAAGGAGAGAATCAGCTCTGATAGTCT<br>GGGGAATCCACCATTCAGGATCAACCACCGAACAGAC<br>CAAACTATATGGGAGTGGAAATAAACTGATAACAGTC<br>GGGAGTTCCAAATATCATCAATCTTTTGTGCCGAGTCC<br>AGGAACACGACCGCAGATAAATGGCCAGTCCGGACGG<br>ATTGATTTTCATTGGTTGATCTTGGATCCCAATGATACA<br>GTTACTTTTAGTTTCAATGGGGCTTTCATAGCTCCAAAT<br>CGTGCCAGCTTCTTGAGGGGAAAGTCCATGGGGATCCA<br>GAGCGATGTGCAGGTTGATGCCAATTGCGAAGGGGAA<br>TGCTACCACAGTGGAGGGACTATAACAAGCAGATTGCC<br>TTTTCAAAACATCAATAGCAGAGCAGTTGGCAAATGCC<br>CAAGATATGTAAAACAGGAAAGTTTATTATTGGCAACT<br>GGGATGAAGAACGTTCCCGAACCTTCCAAAAAAAGGA<br>AAAAAAGAGGCCTGTTTGGCGCTATAGCAGGGTTTATT<br>GAAAATGGTTGGGAAGGTCTGGTCGACGGGTGGTACG<br>GTTTCAGGCATCAGAATGCACAAGGAGAAGGAACTGC<br>AGCAGACTACAAAAGCACCCAATCGGCAATTGATCAG<br>ATAACCGGAAAGTTAAATAGACTCATTGAGAAAACCA<br>ACCAGCAATTTGAGCTAATAGATAATGAATTCACTGAG<br>GTGGAAAAGCAGATTGGCAATTTAATTAACTGGACCAA<br>AGACTCCATCACAGAAGTATGGTCTTACAATGCTGAAC<br>TTCTTGTGGCAATGGAAAACCAGCACACTATTGATTTG<br>GCTGATTCAGAGATGAACAAGCTGTATGAGCGAGTGA<br>GGAAACAATTAAGGGAAAATGCTGAAGAGGATGGCAC<br>TGGTTGCTTTGAAATTTTTCATAAATGTGACGATGATTG<br>TATGGCTAGTATAAGGAACAATACTTATGATCACAGCA<br>AATACAGAGAAGAAGCGATGCAAAATAGAATACAAAT<br>TGACCCAGTCAAATTGAGTAGTGGCTACAAAGATGTGA<br>TACTTTGGTTTAGCTTCGGGGCATCATGCTTTTTGCTTC<br>TTGCCATTGCAATGGGCCTTGTTTTCATATGTGTGAAGA<br>ACGGAAACATGCGGTGCACTATTTGTATATAA |
| 58 Envelope; RRV | AGTGTAACAGAGCACTTTAATGTGTATAAGGCTACTAG<br>ACCATACCTAGCACATTGCGCCGATTGCGGGGACGGGT<br>ACTTCTGCTATAGCCCAGTTGCTATCGAGGAGATCCGA<br>GATGAGGCGTCTGATGGCATGCTTAAGATCCAAGTCTC<br>CGCCCAAATAGGTCTGGACAAGGCAGGCACCCACGCC<br>CACACGAAGCTCCGATATATGGCTGGTCATGATGTTCA<br>GGAATCTAAGAGAGATTCCTTGAGGGTGTACACGTCCG<br>CAGCGTGCTCCATACATGGGACGATGGGACACTTCATC<br>GTCGCACACTGTCCACCAGGCGACTACCTCAAGGTTTC<br>GTTCGAGGACGCAGATTCGCACGTGAAGGCATGTAAG<br>GTCCAATACAAGCACAATCCATTGCCGGTGGGTAGAGA<br>GAAGTTCGTGGTTAGACCACACTTTGGCGTAGAGCTGC<br>CATGCACCTCATACCAGCTGACAACGGCTCCCACCGAC<br>GAGGAGATTGACATGCATACACCGCCAGATATACCGG<br>ATCGCACCCTGCTATCACAGACGGCGGGCAACGTCAAA<br>ATAACAGCAGGCGGCAGGACTATCAGGTACAACTGTA<br>CCTGCGGCCGTGACAACGTAGGCACTACCAGTACTGAC<br>AAGACCATCAACACATGCAAGATTGACCAATGCCATGC<br>TGCCGTCACCAGCCATGACAAATGGCAATTTACCTCTC<br>CATTTGTTCCCAGGGCTGATCAGACAGCTAGGAAAGGC<br>AAGGTACACGTTCCGTTCCCTCTGACTAACGTCACCTG<br>CCGAGTGCCGTTGGCTCGAGCGCCGGATGCCACCTATG<br>GTAAGAAGGAGGTGACCCTGAGATTACACCCAGATCA<br>TCCGACGCTCTTCTCCTATAGGAGTTTAGGAGCCGAAC<br>CGCACCCGTACGAGGAATGGGTTGACAAGTTCTCTGAG<br>CGCATCATCCCAGTGACGGAAGAAGGGATTGAGTACC<br>AGTGGGGCAACAACCCGCCGGTCTGCCTGTGGGCGCA<br>ACTGACGACCGAGGGCAAACCCCATGGCTGGCCACAT<br>GAAATCATTCAGTACTATTATGGACTATACCCCGCCGC<br>CACTATTGCCGCAGTATCCGGGGCGAGTCTGATGGCCC<br>TCCTAACTCTGGCGGCCACATGCTGCATGCTGGCCACC<br>GCGAGGAGAAAGTGCCTAACACCGTACGCCCTGACGC<br>CAGGAGCGGTGGTACCGTTGACACTGGGGCTGCTTTGC<br>TGCGCACCGAGGGCGAATGCA |

-continued

Sequences

| SEQ ID NO: Description | Sequence |
| --- | --- |
| 59 Envelope; MLV 10A1 | AGTGTAACAGAGCACTTTAATGTGTATAAGGCTACTAG ACCATACCTAGCACATTGCGCCGATTGCGGGGACGGGT ACTTCTGCTATAGCCCAGTTGCTATCGAGGAGATCCGA GATGAGGCGTCTGATGGCATGCTTAAGATCCAAGTCTC CGCCCAAATAGGTCTGGACAAGGCAGGCACCCACGCC CACACGAAGCTCCGATATATGGCTGGTCATGATGTTCA GGAATCTAAGAGAGATTCCTTGAGGGTGTACACGTCCG CAGCGTGCTCCATACATGGGACGATGGGACACTTCATC GTCGCACACTGTCCACCAGGCGACTACCTCAAGGTTTC GTTCGAGGACGCAGATTCGCACGTGAAGGCATGTAAG GTCCAATACAAGCACAATCCATTGCCGGTGGGTAGAGA GAAGTTCGTGGTTAGACCACACTTTGGCGTAGAGCTGC CATGCACCTCATACCAGCTGACAACGGCTCCCACCGAC GAGGAGATTGACATGCATACACCGCCAGATATACCGG ATCGCACCCTGCTATCACAGACGGCGGGCAACGTCAAA ATAACAGCAGGCGGCAGGACTATCAGGTACAACTGTA CCTGCGGCCGTGACAACGTAGGCACTACCAGTACTGAC AAGACCATCAACACATGCAAGATTGACCAATGCCATGC TGCCGTCACCAGCCATGACAAATGGCAATTTACCTCTC CATTTGTTCCCAGGGCTGATCAGACAGCTAGGAAAGGC AAGGTACACGTTCCGTTCCCTCTGACTAACGTCACCTG CCGAGTGCCGTTGGCTCGAGCGCCGGATGCCACCTATG GTAAGAAGGAGGTGACCCTGAGATTACACCCAGATCA TCCGACGCTCTTCTCCTATAGGAGTTTAGGAGCCGAAC CGCACCCGTACGAGGAATGGGTTGACAAGTTCTCTGAG CGCATCATCCCAGTGACGGAAGAAGGGATTGAGTACC AGTGGGGCAACAACCCGCCGGTCTGCCTGTGGGCGCA ACTGACGACCGAGGGCAAACCCCATGGCTGGCCACAT GAAATCATTCAGTACTATTATGGACTATACCCCGCCGC CACTATTGCCGCAGTATCCGGGGCGAGTCTGATGGCCC TCCTAACTCTGGCGGCCACATGCTGCATGCTGGCCACC GCGAGGAGAAAGTGCCTAACACCGTACGCCCTGACGC CAGGAGCGGTGGTACCGTTGACACTGGGGCTGCTTTGC TGCGCACCGAGGGCGAATGCA |
| 60 Envelope; Ebola | ATGGGTGTTACAGGAATATTGCAGTTACCTCGTGATCG ATTCAAGAGGACATCATTCTTTCTTTGGGTAATTATCCT TTTCCAAAGAACATTTTCCATCCCACTTGGAGTCATCCA CAATAGCACATTACAGGTTAGTGATGTCGACAAACTGG TTTGCCGTGACAAACTGTCATCCACAAATCAATTGAGA TCAGTTGGACTGAATCTCGAAGGGAATGGAGTGGCAA CTGACGTGCCATCTGCAACTAAAAGATGGGGCTTCAGG TCCGGTGTCCCACCAAAGGTGGTCAATTATGAAGCTGG TGAATGGGCTGAAAACTGCTACAATCTTGAAATCAAAA AACCTGACGGGAGTGAGTGTCTACCAGCAGCGCCAGA CGGGATTCGGGGCTTCCCCCGGTGCCGGTATGTGCACA AAGTATCAGGAACGGGACCGTGTGCCGGAGACTTTGCC TTCCACAAAGAGGGTGCTTTCTTCCTGTATGACCGACTT GCTTCCACAGTTATCTACCGAGGAACGACTTTCGCTGA AGGTGTCGTTGCATTTCTGATACTGCCCCAAGCTAAGA AGGACTTCTTCAGCTCACACCCCTTGAGAGAGCCGGTC AATGCAACGGAGGACCCGTCTAGTGGCTACTATTCTAC CACAATTAGATATCAAGCTACCGGTTTTGGAACCAATG AGACAGAGTATTTGTTCGAGGTTGACAATTTGACCTAC GTCCAACTTGAATCAAGATTCACACCACAGTTTCTGCT CCAGCTGAATGAGACAATATATACAAGTGGGAAAAGG AGCAATACCACGGGAAAACTAATTTGGAAGGTCAACC CCGAAATTGATACAACAATCGGGGAGTGGGCCTTCTGG GAAACTAAAAAAACCTCACTAGAAAAATTCGCAGTGA AGAGTTGTCTTTCACAGCTGTATCAAACAGAGCCAAAA ACATCAGTGGTCAGAGTCCGGCGCGAACTTCTTCCGAC CCAGGGACCAACACAACAACTGAAGACCACAAAATCA TGGCTTCAGAAAATTCCTCTGCAATGGTTCAAGTGCAC AGTCAAGGAAGGGAAGCTGCAGTGTCGCATCTGACAA CCCTTGCCACAATCTCCACGAGTCCTCAACCCCCCACA ACCAAACCAGGTCCGGACAACAGCACCCCACAATACAC CCGTGTATAAACTTGACATCTCTGAGGCAACTCAAGTT GAACAACATCACCGCAGAACAGACAACGACAGCACAG CCTCCGACACTCCCCCCGCCACGACCGCAGCCGGACCC CTAAAAGCAGAGAACACCAACACGAGCAAGGGTACCG ACCTCCTGGACCCCGCCACCACAACAAGTCCCCAAAAC CACAGCGAGACCGCTGGCAACAACAACACTCATCACC AAGATACCGGAGAAGAGAGTGCCAGCAGCGGGAAGCT |

-continued

| Sequences | |
|---|---|
| SEQ ID NO: Description | Sequence |
| | AGGCTTAATTACCAATACTATTGCTGGAGTCGCAGGAC TGATCACAGGCGGGAGGAGAGCTCGAAGAGAAGCAAT TGTCAATGCTCAACCCAAATGCAACCCTAATTTACATT ACTGGACTACTCAGGATGAAGGTGCTGCAATCGGACTG GCCTGGATACCATATTTCGGGCCAGCAGCCGAGGGAAT TTACATAGAGGGGCTGATGCACAATCAAGATGGTTTAA TCTGTGGGTTGAGACAGCTGGCCAACGAGACGACTCAA GCTCTTCAACTGTTCCTGAGAGCCACAACCGAGCTACG CACCTTTTCAATCCTCAACCGTAAGGCAATTGATTTCTT GCTGCAGCGATGGGGCGGCACATGCCACATTTTGGGAC CGGACTGCTGTATCGAACCACATGATTGGACCAAGAAC ATAACAGACAAAATTGATCAGATTATTCATGATTTTGT TGATAAAACCCTTCCGGACCAGGGGGACAATGACAATT GGTGGACAGGATGGAGACAATGGATACCGGCAGGTAT TGGAGTTACAGGCGTTATAATTGCAGTTATCGCTTTATT CTGTATATGCAAATTTGTCTTTTAG |
| 61 Control shRNA sequence | GCCGCTTTGTAGGATAGAGCTCGAGCTCTATCCTACAA AGCGGCTTTTT |

What is claimed is:

1. A lentiviral vector system for treating Parkinson's disease in a patient in need thereof, the system comprising:

a therapeutic vector comprising an encoded shRNA for inhibiting PARP1 expression in neurons, wherein the encoded shRNA comprises at least 80% sequence identity to the entire length of any one of SEQ ID NOs: 6, 7 or 10 an envelope plasmid comprising a neuron-specific sequence for delivering the shRNA to a neuron; and at least one helper plasmid comprising gag, pol, and rev genes, wherein when the therapeutic vector, the envelope plasmid and the at least one helper plasmid are transfected into a packaging cell line, a neuron-specific lentiviral particle capable of inhibiting PARP1 expression in neurons is produced by the packaging cell line.

2. The lentiviral vector system of claim 1, wherein the neuron-specific sequence encodes at least one of VSV-G, FUG-C, or gp64.

3. The lentiviral vector system of claim 1, wherein the neuron-specific sequence encodes a protein that is configured to enable transduction of a lentiviral particle into a neuron.

4. The lentiviral vector system of claim 1, wherein the neuron-specific sequence encodes a protein that is configured to enable transduction of a lentiviral particle into a TH+ neuron.

* * * * *

SEQUENCE LISTING

<160> NUMBER OF SEQ ID NOS: 61

<210> SEQ ID NO 1
<211> LENGTH: 21
<212> TYPE: DNA
<213> ORGANISM: Homo sapiens

<400> SEQUENCE: 1
cttcgttaga atgtctgcct t 21

<210> SEQ ID NO 2
<211> LENGTH: 21
<212> TYPE: DNA
<213> ORGANISM: Homo sapiens

<400> SEQUENCE: 2
gcagcttcat aaccgaagat t 21

<210> SEQ ID NO 3
<211> LENGTH: 21
<212> TYPE: DNA
<213> ORGANISM: Homo sapiens

<400> SEQUENCE: 3
ccgagaaatc tcttacctca a 21

<210> SEQ ID NO 4
<211> LENGTH: 21
<212> TYPE: DNA
<213> ORGANISM: Homo sapiens

<400> SEQUENCE: 4
cgacctgatc tggaacatca a 21

<210> SEQ ID NO 5
<211> LENGTH: 19
<212> TYPE: DNA
<213> ORGANISM: Homo sapiens

-continued

<400> SEQUENCE: 5
gttgctgatg ggtagtacc 19

<210> SEQ ID NO 6
<211> LENGTH: 53
<212> TYPE: DNA
<213> ORGANISM: Homo sapiens

<400> SEQUENCE: 6
cttcgttaga atgtctgcct tctcgagaag gcagacattc taacgaagtt ttt 53

<210> SEQ ID NO 7
<211> LENGTH: 53
<212> TYPE: DNA
<213> ORGANISM: Homo sapiens

<400> SEQUENCE: 7
gcagcttcat aaccgaagat tctcgagaat cttcggttat gaagctgctt ttt 53

<210> SEQ ID NO 8
<211> LENGTH: 53
<212> TYPE: DNA
<213> ORGANISM: Homo sapiens

<400> SEQUENCE: 8
ccgagaaatc tcttacctca actcgagttg aggtaagaga tttctcggtt ttt 53

<210> SEQ ID NO 9
<211> LENGTH: 53
<212> TYPE: DNA
<213> ORGANISM: Homo sapiens

<400> SEQUENCE: 9
cgacctgatc tggaacatca actcgagttg atgttccaga tcaggtcgtt ttt 53

<210> SEQ ID NO 10
<211> LENGTH: 52
<212> TYPE: DNA
<213> ORGANISM: Homo sapiens

<400> SEQUENCE: 10
gttgctgatg ggtagtacct tcaagagagg tactacccat cagcaacttt tt 52

<210> SEQ ID NO 11
<211> LENGTH: 21
<212> TYPE: DNA
<213> ORGANISM: Mus musculus

<400> SEQUENCE: 11
gcacttcatg aagctgtatg a 21

<210> SEQ ID NO 12
<211> LENGTH: 21
<212> TYPE: DNA
<213> ORGANISM: Mus musculus

<400> SEQUENCE: 12
gcacagttat cggcagtaac a 21

<210> SEQ ID NO 13
<211> LENGTH: 21
<212> TYPE: DNA
<213> ORGANISM: Mus musculus -continued

<400> SEQUENCE: 13
ggaggcaagt tgacaggatc t 21

<210> SEQ ID NO 14
<211> LENGTH: 21
<212> TYPE: DNA
<213> ORGANISM: Mus musculus

<400> SEQUENCE: 14
tcgacgtcaa ctacgagaaa c 21

<210> SEQ ID NO 15
<211> LENGTH: 21
<212> TYPE: DNA
<213> ORGANISM: Mus musculus

<400> SEQUENCE: 15
gcccttggaa acatgtatga a 21

<210> SEQ ID NO 16
<211> LENGTH: 53
<212> TYPE: DNA
<213> ORGANISM: Mus musculus

<400> SEQUENCE: 16
gcacttcatg aagctgtatg actcgagtca tacagcttca tgaagtgctt ttt 53

<210> SEQ ID NO 17
<211> LENGTH: 53
<212> TYPE: DNA
<213> ORGANISM: Mus musculus

<400> SEQUENCE: 17
gcacagttat cggcagtaac actcgagtgt tactgccgat aactgtgctt ttt 53

<210> SEQ ID NO 18
<211> LENGTH: 53
<212> TYPE: DNA
<213> ORGANISM: Mus musculus

<400> SEQUENCE: 18
ggaggcaagt tgacaggatc tctcgagaga tcctgtcaac ttgcctcctt ttt 53

<210> SEQ ID NO 19
<211> LENGTH: 53
<212> TYPE: DNA
<213> ORGANISM: Mus musculus

<400> SEQUENCE: 19
tcgacgtcaa ctacgagaaa cctcgaggtt tctcgtagtt gacgtcgatt ttt 53

<210> SEQ ID NO 20
<211> LENGTH: 53
<212> TYPE: DNA
<213> ORGANISM: Mus musculus

<400> SEQUENCE: 20
gcccttggaa acatgtatga actcgagttc atacatgttt ccaagggctt ttt 53

<210> SEQ ID NO 21
<211> LENGTH: 228
<212> TYPE: DNA

<213> ORGANISM: Rous Sarcoma virus

<400> SEQUENCE: 21
gtagtcttat gcaatactct tgtagtcttg caacatggta acgatgagtt agcaacatgc 60
cttacaagga gagaaaaagc accgtgcatg ccgattggtg gaagtaaggt ggtacgatcg 120
tgccttatta ggaaggcaac agacgggtct gacatggatt ggacgaacca ctgaattgcc 180
gcattgcaga gatattgtat ttaagtgcct agctcgatac aataaacg 228

<210> SEQ ID NO 22
<211> LENGTH: 180
<212> TYPE: DNA
<213> ORGANISM: Rous Sarcoma virus

<400> SEQUENCE: 22
ggtctctctg gttagaccag atctgagcct gggagctctc tggctaacta gggaacccac 60
tgcttaagcc tcaataaagc ttgccttgag tgcttcaagt agtgtgtgcc cgtctgttgt 120
gtgactctgg taactagaga tccctcagac ccttttagtc agtgtggaaa atctctagca 180

<210> SEQ ID NO 23
<211> LENGTH: 1503
<212> TYPE: DNA
<213> ORGANISM: Human Immunodeficiency Virus

<400> SEQUENCE: 23
atgggtgcga gagcgtcagt attaagcggg ggagaattag atcgatggga aaaaattcgg 60
ttaaggccag ggggaaagaa aaaatataaa ttaaaacata tagtatgggc aagcagggag 120
ctagaacgat tcgcagttaa tcctggcctg ttagaaacat cagaaggctg tagacaaata 180
ctgggacagc tacaaccatc ccttcagaca ggatcagaag aacttagatc attatataat 240
acagtagcaa ccctctattg tgtgcatcaa aggatagaga taaaagacac caaggaagct 300
ttagacaaga tagaggaaga gcaaaacaaa agtaagaaaa aagcacagca agcagcagct 360
gacacaggac acagcaatca ggtcagccaa aattacccta tagtgcagaa catccagggg 420
caaatggtac atcaggccat atcacctaga actttaaatg catgggtaaa agtagtagaa 480
gagaaggctt tcagcccaga agtgataccc atgttttcag cattatcaga aggagccacc 540
ccacaagatt taaacaccat gctaaacaca gtggggggac atcaagcagc catgcaaatg 600
ttaaaagaga ccatcaatga ggaagctgca gaatgggata gagtgcatcc agtgcatgca 660
gggcctattg caccaggcca gatgagagaa ccaaggggaa gtgacatagc aggaactact 720
agtacccttc aggaacaaat aggatggatg acacataatc cacctatccc agtaggagaa 780
atctataaaa gatggataat cctgggatta aataaaatag taagaatgta tagccctacc 840
agcattctgg acataagaca aggaccaaag gaacccttta gagactatgt agaccgattc 900
tataaaactc taagagccga gcaagcttca caagaggtaa aaaattggat gacagaaacc 960
ttgttggtcc aaaatgcgaa cccagattgt aagactattt taaaagcatt gggaccagga 1020
gcgacactag aagaaatgat gacagcatgt cagggagtgg ggggacccgg ccataaagca 1080
agagttttgg ctgaagcaat gagccaagta acaaatccag ctaccataat gatacagaaa 1140
ggcaatttta ggaaccaaag aaagactgtt aagtgtttca attgtggcaa agaagggcac 1200
atagccaaaa attgcagggc ccctaggaaa aagggctgtt ggaaatgtgg aaaggaagga 1260
caccaaatga aagattgtac tgagagacag gctaattttt tagggaagat ctggccttcc 1320
cacaagggaa ggccagggaa ttttcttcag agcagaccag agccaacagc cccaccagaa 1380
gagagcttca ggtttgggga agagacaaca actccctctc agaagcagga gccgatagac 1440
aaggaactgt atcctttagc ttccctcaga tcactctttg gcagcgaccc ctcgtcacaa 1500
taa 1503

<210> SEQ ID NO 24
<211> LENGTH: 233
<212> TYPE: DNA
<213> ORGANISM: Human Immunodeficiency Virus

<400> SEQUENCE: 24
aggagctttg ttccttgggt tcttgggagc agcaggaagc actatgggcg cagcctcaat 60
gacgctgacg gtacaggcca gacaattatt gtctggtata gtgcagcagc agaacaattt 120
gctgagggct attgaggcgc aacagcatct gttgcaactc acagtctggg gcatcaagca 180
gctccaggca agaatcctgg ctgtggaaag atacctaaag gatcaacagc tcc 233

<210> SEQ ID NO 25
<211> LENGTH: 1519
<212> TYPE: DNA
<213> ORGANISM: Vesicular Stomatitis Indiana Virus

<400> SEQUENCE: 25
atgaagtgcc ttttgtactt agccttttta ttcattgggg tgaattgcaa gttcaccata 60
gtttttccac acaaccaaaa aggaaactgg aaaaatgttc cttctaatta ccattattgc 120
ccgtcaagct cagatttaaa ttggcataat gacttaatag gcacagcctt acaagtcaaa 180
atgcccaaga gtcacaaggc tattcaagca gacggttgga tgtgtcatgc ttccaaatgg 240
gtcactactt gtgatttccg ctggtatgga ccgaagtata taacacattc catccgatcc 300
ttcactccat ctgtagaaca atgcaaggaa agcattgaac aaacgaaaca aggaacttgg 360
ctgaatccag gcttccctcc tcaaagttgt ggatatgcaa ctgtgacgga tgccgaagca 420
gtgattgtcc aggtgactcc tcaccatgtg ctggttgatg aatacacagg agaatgggtt 480
gattcacagt tcatcaacgg aaaatgcagc aattacatat gccccactgt ccataactct 540
acaacctggc attctgacta taaggtcaaa gggctatgtg attctaacct catttccatg 600
gacatcacct tcttctcaga ggacggagag ctatcatccc tgggaaagga gggcacaggg 660
ttcagaagta actactttgc ttatgaaact ggaggcaagg cctgcaaaat gcaatactgc 720
aagcattggg gagtcagact cccatcaggt gtctggttcg agatggctga taaggatctc 780
tttgctgcag ccagattccc tgaatgccca gaagggtcaa gtatctctgc tccatctcag 840
acctcagtgg atgtaagtct aattcaggac gttgagagga tcttggatta ttccctctgc 900
caagaaacct ggagcaaaat cagagcgggt cttccaatct ctccagtgga tctcagctat 960
cttgctccta aaaacccagg aaccggtcct gctttcacca taatcaatgg taccctaaaa 1020
tactttgaga ccagatacat cagagtcgat attgctgctc caatcctctc aagaatggtc 1080
ggaatgatca gtggaactac cacagaaagg gaactgtggg atgactgggc accatatgaa 1140
gacgtggaaa ttggacccaa tggagttctg aggaccagtt caggatataa gtttccttta 1200
tacatgattg gacatggtat gttggactcc gatcttcatc ttagctcaaa ggctcaggtg 1260
ttcgaacatc ctcacattca agacgctgct tcgcaacttc ctgatgatga gagtttattt 1320
tttggtgata ctgggctatc caaaaatcca atcgagcttg tagaaggttg gttcagtagt 1380
tggaaaagct ctattgcctc tttttcttt atcatagggt taatcattgg actattcttg 1440

-continued gttctccgag ttggtatcca tctttgcatt aaattaaagc acaccaagaa aagacagatt 1500
tatacagaca tagagatga 1519

<210> SEQ ID NO 26
<211> LENGTH: 118
<212> TYPE: DNA
<213> ORGANISM: Rous Sarcoma virus

<400> SEQUENCE: 26
ttttaaaaga aaaggggga ttgggggta cagtgcaggg gaaagaatag tagacataat 60
agcaacagac atacaaacta aagaattaca aaaacaaatt acaaaattca aaatttta 118

<210> SEQ ID NO 27
<211> LENGTH: 217
<212> TYPE: DNA
<213> ORGANISM: Rous Sarcoma virus

<400> SEQUENCE: 27
gaacgctgac gtcatcaacc cgctccaagg aatcgcgggc ccagtgtcac taggcgggaa 60
cacccagcgc gcgtgcgccc tggcaggaag atggctgtga gggacagggg agtggcgccc 120
tgcaatattt gcatgtcgct atgtgttctg ggaaatcacc ataaacgtga aatgtctttg 180
gatttgggaa tcttataagt tctgtatgag accactt 217

<210> SEQ ID NO 28
<211> LENGTH: 532
<212> TYPE: DNA
<213> ORGANISM: Rous Sarcoma virus

<400> SEQUENCE: 28
gctccggtgc ccgtcagtgg gcagagcgca catcgcccac agtccccgag aagttggggg 60
gaggggtcgg caattgaacg ggtgcctaga gaaggtggcg cggggtaaac tgggaaagtg 120
atgtcgtgta ctggctccgc ctttttcccg agggtggggg agaaccgtat ataagtgcag 180
tagtcgccgt gaacgttctt tttcgcaacg ggtttgccgc cagaacacag ctgaagcttc 240
gaggggctcg catctctcct tcacgcgccc gccgccctac ctgaggccgc catccacgcc 300
ggttgagtcg cgttctgccg cctcccgcct gtggtgcctc ctgaactgcg tccgccgtct 360
aggtaagttt aaagctcagg tcgagaccgg gcctttgtcc ggcgctccct tggagcctac 420
ctagactcag ccggctctcc acgctttgcc tgaccctgct tgctcaactc tacgtctttg 480
tttcgttttc tgttctgcgc cgttacagat ccaagctgtg accggcgcct ac 532

<210> SEQ ID NO 29
<211> LENGTH: 759
<212> TYPE: DNA
<213> ORGANISM: Aequorea victoria

<400> SEQUENCE: 29
atggagagcg acgagagcgg cctgcccgcc atggagatcg agtgccgcat caccggcacc 60
ctgaacggcg tggagttcga gctggtgggc ggcggagagg gcacccccaa gcagggccgc 120
atgaccaaca agatgaagag caccaaaggc gccctgacct tcagcccccta cctgctgagc 180 cacgtgatgg gctacggctt ctaccacttc ggcacctacc ccagcggcta cgagaacccc 240
ttcctgcacg ccatcaacaa cggcggctac accaacaccc gcatcgagaa gtacgaggac 300
ggcggcgtgc tgcacgtgag cttcagctac cgctacgagg ccggccgcgt gatcggcgac 360
ttcaaggtgg tgggcaccgg cttccccgag gacagcgtga tcttcaccga caagatcatc 420
cgcagcaacg ccaccgtgga gcacctgcac cccatgggcg ataacgtgct ggtgggcagc 480
ttcgcccgca ccttcagcct gcgcgacggc ggctactaca gcttcgtggt ggacagccac 540
atgcacttca agagcgccat ccaccccagc atcctgcaga acgggggccc catgttcgcc 600
ttccgccgcg tggaggagct gcacagcaac accgagctgg gcatcgtgga gtaccagcac 660
gccttcaaga cccccatcgc cttcgccaga tcccgcgctc agtcgtccaa ttctgccgtg 720
gacggcaccg ccggacccgg ctccaccgga tctcgctaa 759

<210> SEQ ID NO 30
<211> LENGTH: 590
<212> TYPE: DNA
<213> ORGANISM: Woodchuck hepatitis B virus

<400> SEQUENCE: 30
aatcaacctc tgattacaaa atttgtgaaa gattgactgg tattcttaac tatgttgctc 60
cttttacgct atgtggatac gctgctttaa tgcctttgta tcatgctatt gcttcccgta 120
tggctttcat tttctcctcc ttgtataaat cctggttgct gtctctttat gaggagttgt 180
ggcccgttgt caggcaacgt ggcgtggtgt gcactgtgtt tgctgacgca acccccactg 240
gttggggcat tgccaccacc tgtcagctcc tttccgggac tttcgctttc cccctcccta 300
ttgccacggc ggaactcatc gccgcctgcc ttgcccgctg ctggacaggg gctcggctgt 360
tgggcactga caattccgtg gtgttgtcgg ggaaatcatc gtcctttcct tggctgctcg 420
cctgtgttgc cacctggatt ctgcgcggga cgtccttctg ctacgtccct tcggccctca 480
atccagcgga ccttccttcc cgcggcctgc tgccggctct gcggcctctt ccgcgtcttc 540
gccttcgccc tcagacgagt cggatctccc tttgggccgc ctccccgcct 590

<210> SEQ ID NO 31
<211> LENGTH: 250
<212> TYPE: DNA
<213> ORGANISM: Human Immunodeficiency Virus

<400> SEQUENCE: 31
tggaagggct aattcactcc caacgaagat aagatctgct ttttgcttgt actgggtctc 60
tctggttaga ccagatctga gcctgggagc tctctggcta actagggaac ccactgctta 120
agcctcaata aagcttgcct tgagtgcttc aagtagtgtg tgcccgtctg ttgtgtgact 180
ctggtaacta gagatccctc agaccctttt agtcagtgtg gaaaatctct agcagtagta 240
gttcatgtca 250

<210> SEQ ID NO 32
<211> LENGTH: 352
<212> TYPE: DNA
<213> ORGANISM: artificial sequence
<220> FEATURE:
<223> OTHER INFORMATION: Helper/Rev CMV early (CAG) enhancer DNA
construct

<400> SEQUENCE: 32
tagttattaa tagtaatcaa ttacggggtc attagttcat agcccatata tggagttccg 60
cgttacataa cttacggtaa atggcccgcc tggctgaccg cccaacgacc cccgcccatt 120
gacgtcaata atgacgtatg ttcccatagt aacgccaata gggactttcc attgacgtca 180
atgggtggac tatttacggt aaactgccca cttggcagta catcaagtgt atcatatgcc 240
aagtacgccc cctattgacg tcaatgacgg taaatggccc gcctggcatt atgcccagta 300
catgacctta tgggactttc ctacttggca gtacatctac gtattagtca tc 352

<210> SEQ ID NO 33
<211> LENGTH: 290
<212> TYPE: DNA
<213> ORGANISM: artificial sequence
<220> FEATURE:
<223> OTHER INFORMATION: Helper/Rev Chicken beta actin (CAG) promoter DNA construct

<400> SEQUENCE: 33
gctattacca tgggtcgagg tgagccccac gttctgcttc actctcccca tctccccccc 60
ctccccaccc ccaattttgt atttatttat tttttaatta ttttgtgcag cgatgggggc 120
gggggggggg ggggcgcgcg ccaggcgggg cggggcgggg cgaggggcgg ggcggggcga 180
ggcggagagg tgcggcggca gccaatcaga gcggcgcgct ccgaaagttt ccttttatgg 240
cgaggcggcg gcggcggcgg ccctataaaa agcgaagcgc gcggcgggcg 290

<210> SEQ ID NO 34
<211> LENGTH: 960
<212> TYPE: DNA
<213> ORGANISM: artificial sequence
<220> FEATURE:
<223> OTHER INFORMATION: Helper/Rev Chicken beta actin intron DNA construct

<400> SEQUENCE: 34
ggagtcgctg cgttgccttc gccccgtgcc ccgctccgcg ccgcctcgcg ccgcccgccc 60
cggctctgac tgaccgcgtt actcccacag gtgagcgggc gggacggccc ttctcctccg 120
ggctgtaatt agcgcttggt ttaatgacgg ctcgtttctt ttctgtggct gcgtgaaagc 180
cttaaagggc tccgggaggg ccctttgtgc ggggggggagc ggctcggggg gtgcgtgcgt 240
gtgtgtgtgc gtggggagcg ccgcgtgcgg cccgcgctgc ccggcggctg tgagcgctgc 300
gggcgcggcg cggggctttg tgcgctccgc gtgtgcgcga ggggagcgcg gccgggggcg 360
gtgccccgcg gtgcgggggg gctgcgaggg gaacaaaggc tgcgtgcggg gtgtgtgcgt 420
gggggggtga gcagggggtg tgggcgcggc ggtcgggctg taaccccccc ctgcaccccc 480
ctccccgagt tgctgagcac ggcccggctt cgggtgcggg gctccgtgcg gggcgtggcg 540
cggggctcgc cgtgccgggc ggggggtggc ggcaggtggg ggtgccgggc ggggcggggc 600
cgcctcgggc cggggagggc tcgggggagg ggcgcggcgg ccccggagcg ccggcggctg 660
tcgaggcgcg gcgagccgca gccattgcct tttatggtaa tcgtgcgaga gggcgcaggg 720
acttcctttg tcccaaatct ggcggagccg aaatctggga ggcgccgccg caccccctct 780
agcgggcgcg ggcgaagcgg tgcggcgccg gcaggaagga aatgggcggg gagggccttc 840
gtgcgtcgcc gcgccgccgt ccccttctcc atctccagcc tcggggctgc cgcagggggga 900 cggctgcctt cggggggggac ggggcagggc ggggttcggc ttctggcgtg tgaccggcgg 960

<210> SEQ ID NO 35
<211> LENGTH: 1872
<212> TYPE: DNA
<213> ORGANISM: artificial sequence
<220> FEATURE:
<223> OTHER INFORMATION: Helper/Rev HIV Pol DNA construct

<400> SEQUENCE: 35
atgaatttgc caggaagatg gaaaccaaaa atgatagggg gaattggagg ttttatcaaa 60

```
gtaggacagt atgatcagat actcatagaa atctgcggac ataaagctat aggtacagta    120
ttagtaggac ctacacctgt caacataatt ggaagaaatc tgttgactca gattggctgc    180
actttaaatt ttcccattag tcctattgag actgtaccag taaaattaaa gccaggaatg    240
gatggcccaa aagttaaaca atggccattg acagaagaaa aaataaaagc attagtagaa    300
atttgtacag aaatggaaaa ggaaggaaaa atttcaaaaa ttgggcctga aaatccatac    360
aatactccag tatttgccat aaagaaaaaa gacagtacta aatggagaaa attagtagat    420
ttcagagaac ttaataagag aactcaagat ttctgggaag ttcaattagg aataccacat    480
cctgcagggt taaaacagaa aaaatcagta acagtactgg atgtgggcga tgcatatttt    540
tcagttccct tagataaaga cttcaggaag tatactgcat ttaccatacc tagtataaac    600
aatgagacac cagggattag atatcagtac aatgtgcttc cacagggatg gaaaggatca    660
ccagcaatat tccagtgtag catgacaaaa atcttagagc cttttagaaa acaaaatcca    720
gacatagtca tctatcaata catggatgat ttgtatgtag gatctgactt agaaataggg    780
cagcatagaa caaaaataga ggaactgaga caacatctgt tgaggtgggg atttaccaca    840
ccagacaaaa aacatcagaa agaacctcca ttcctttgga tgggttatga actccatcct    900
gataaatgga cagtacagcc tatagtgctg ccagaaaagg acagctggac tgtcaatgac    960
atacagaaat tagtgggaaa attgaattgg gcaagtcaga tttatgcagg gattaaagta   1020
aggcaattat gtaaacttct taggggaacc aaagcactaa cagaagtagt accactaaca   1080
gaagaagcag agctagaact ggcagaaaac agggagattc taaaagaacc ggtacatgga   1140
gtgtattatg acccatcaaa agacttaata gcagaaatac agaagcaggg gcaaggccaa   1200
tggacatatc aaatttatca agagccattt aaaaatctga aaacaggaaa atatgcaaga   1260
atgaagggtg cccacactaa tgatgtgaaa caattaacag aggcagtaca aaaaatagcc   1320
acagaaagca tagtaatatg gggaaagact cctaaattta aattacccat acaaaaggaa   1380
acatgggaag catggtggac agagtattgg caagccacct ggattcctga gtgggagttt   1440
gtcaataccc ctcccttagt gaagttatgg taccagttag agaaagaacc cataatagga   1500
gcagaaactt tctatgtaga tggggcagcc aatagggaaa ctaaattagg aaaagcagga   1560
tatgtaactg acagaggaag acaaaaagtt gtccccctaa cggacacaac aaatcagaag   1620
actgagttac aagcaattca tctagctttg caggattcgg gattagaagt aaacatagtg   1680
acagactcac aatatgcatt gggaatcatt caagcacaac cagataagag tgaatcagag   1740
ttagtcagtc aaataataga gcagttaata aaaaaggaaa aagtctacct ggcatgggta   1800
ccagcacaca aaggaattgg aggaaatgaa caagtagatg ggttggtcag tgctggaatc   1860
aggaaagtac ta                                                       1872
```

<210> SEQ ID NO 36
<211> LENGTH: 867
<212> TYPE: DNA
<213> ORGANISM: artificial sequence
<220> FEATURE:
<223> OTHER INFORMATION: Helper Rev HIV Integrase DNA construct

<400> SEQUENCE: 36

```
tttttagatg gaatagataa ggcccaagaa gaacatgaga aatatcacag taattggaga     60
gcaatggcta gtgattttaa cctaccacct gtagtagcaa aagaaatagt agccagctgt    120
gataaatgtc agctaaaagg ggaagccatg catggacaag tagactgtag cccaggaata    180
tggcagctag attgtacaca tttagaagga aaagttatct tggtagcagt tcatgtagcc    240
```

agtggatata tagaagcaga agtaattcca gcagagacag ggcaagaaac agcatacttc 300
ctcttaaaat tagcaggaag atggccagta aaaacagtac atacagacaa tggcagcaat 360
ttcaccagta ctacagttaa ggccgcctgt tggtgggcgg ggatcaagca ggaatttggc 420
attccctaca atccccaaag tcaaggagta atagaatcta tgaataaaga attaaagaaa 480
attataggac aggtaagaga tcaggctgaa catcttaaga cagcagtaca aatggcagta 540
ttcatccaca attttaaaag aaaagggggg attggggggt acagtgcagg ggaaagaata 600
gtagacataa tagcaacaga catacaaact aaagaattac aaaaacaaat tacaaaaatt 660
caaaattttc gggtttatta cagggacagc agagatccag tttggaaagg accagcaaag 720
ctcctctgga aaggtgaagg ggcagtagta atacaagata atagtgacat aaaagtagtg 780
ccaagaagaa aagcaaagat catcagggat tatggaaaac agatggcagg tgatgattgt 840
gtggcaagta gacaggatga ggattaa 867

<210> SEQ ID NO 37
<211> LENGTH: 351
<212> TYPE: DNA
<213> ORGANISM: artificial sequence
<220> FEATURE:
<223> OTHER INFORMATION: Helper/Rev HIV Rev DNA construct

<400> SEQUENCE: 37
atggcaggaa gaagcggaga cagcgacgaa gaactcctca aggcagtcag actcatcaag 60
tttctctatc aaagcaaccc acctcccaat cccgagggga cccgacaggc ccgaaggaat 120
agaagaagaa ggtggagaga gagacagaga cagatccatt cgattagtga acggatcctt 180
agcacttatc tgggacgatc tgcggagcct gtgcctcttc agctaccacc gcttgagaga 240
cttactcttg attgtaacga ggattgtgga acttctggga cgcagggggt gggaagccct 300
caaatattgg tggaatctcc tacaatattg gagtcaggag ctaaagaata g 351

<210> SEQ ID NO 38
<211> LENGTH: 448
<212> TYPE: DNA
<213> ORGANISM: artificial sequence
<220> FEATURE:
<223> OTHER INFORMATION: Helper/Rev Rabbit beta globin poly A DNA
construct

<400> SEQUENCE: 38
agatcttttt ccctctgcca aaaattatgg ggacatcatg aagccccttg agcatctgac 60
ttctggctaa taaaggaaat ttattttcat tgcaatagtg tgttggaatt ttttgtgtct 120
ctcactcgga aggacatatg ggagggcaaa tcatttaaaa catcagaatg agtatttggt 180
ttagagtttg gcaacatatg ccatatgctg gctgccatga acaaaggtgg ctataaagag 240
gtcatcagta tatgaaacag ccccctgctg tccattcctt attccataga aaagccttga 300
cttgaggtta gatttttttt atattttgtt ttgtgttatt tttttcttta acatccctaa 360
aattttcctt acatgtttta ctagccagat ttttcctcct ctcctgacta ctcccagtca 420
tagctgtccc tcttctctta tgaagatc 448

<210> SEQ ID NO 39
<211> LENGTH: 577
<212> TYPE: DNA
<213> ORGANISM: Cytomegalovirus

<400> SEQUENCE: 39

```
acattgatta ttgactagtt attaatagta atcaattacg gggtcattag ttcatagccc     60

atatatggag ttccgcgtta cataacttac ggtaaatggc ccgcctggct gaccgcccaa    120

cgacccccgc ccattgacgt caataatgac gtatgttccc atagtaacgc caatagggac    180

tttccattga cgtcaatggg tggagtattt acggtaaact gcccacttgg cagtacatca    240

agtgtatcat atgccaagta cgccccctat tgacgtcaat gacggtaaat ggcccgcctg    300

gcattatgcc cagtacatga ccttatggga ctttcctact tggcagtaca tctacgtatt    360

agtcatcgct attaccatgg tgatgcggtt ttggcagtac atcaatgggc gtggatagcg    420

gtttgactca cggggatttc caagtctcca ccccattgac gtcaatggga gtttgttttg    480

gcaccaaaat caacgggact ttccaaaatg tcgtaacaac tccgccccat tgacgcaaat    540

gggcggtagg cgtgtacggt gggaggtcta tataagc                             577
```

<210> SEQ ID NO 40
<211> LENGTH: 573
<212> TYPE: DNA
<213> ORGANISM: Homo sapiens

<400> SEQUENCE: 40

```
gtgagtttgg ggacccttga ttgttctttc tttttcgcta ttgtaaaatt catgttatat     60

ggagggggca aagttttcag ggtgttgttt agaatgggaa gatgtccctt gtatcaccat    120

ggaccctcat gataattttg tttctttcac tttctactct gttgacaacc attgtctcct    180

cttattttct tttcattttc tgtaactttt tcgttaaact ttagcttgca tttgtaacga    240

atttttaaat tcacttttgt ttatttgtca gattgtaagt actttctcta atcacttttt    300

tttcaaggca atcagggtat attatattgt acttcagcac agttttagag aacaattgtt    360

ataattaaat gataaggtag aatatttctg catataaatt ctggctggcg tggaaatatt    420

cttattggta gaaacaacta caccctggtc atcatcctgc ctttctcttt atggttacaa    480

tgatatacac tgtttgagat gaggataaaa tactctgagt ccaaaccggg cccctctgct    540

aaccatgttc atgccttctt ctctttccta cag                                 573
```

<210> SEQ ID NO 41
<211> LENGTH: 31
<212> TYPE: DNA
<213> ORGANISM: artificial sequence
<220> FEATURE:
<223> OTHER INFORMATION: Primer DNA fragment

<400> SEQUENCE: 41

```
taagcagaat tcatgaattt gccaggaaga t                                    31
```

<210> SEQ ID NO 42
<211> LENGTH: 36
<212> TYPE: DNA
<213> ORGANISM: artificial sequence
<220> FEATURE:
<223> OTHER INFORMATION: Primer DNA fragment

<400> SEQUENCE: 42

```
ccatacaatg aatggacact aggcggccgc acgaat                               36
```

<210> SEQ ID NO 43
<211> LENGTH: 2745
<212> TYPE: DNA
<213> ORGANISM: artificial sequence
<220> FEATURE:

<223> OTHER INFORMATION: Gag, Pol, Integrase DNA fragment

<400> SEQUENCE: 43

```
gaattcatga atttgccagg aagatggaaa ccaaaaatga tagggggaat tggaggtttt     60
atcaaagtaa gacagtatga tcagatactc atagaaatct gcggacataa agctataggt    120
acagtattag taggacctac acctgtcaac ataattggaa gaaatctgtt gactcagatt    180
ggctgcactt taaattttcc cattagtcct attgagactg taccagtaaa attaaagcca    240
ggaatggatg gcccaaaagt taaacaatgg ccattgacag aagaaaaaat aaaagcatta    300
gtagaaattt gtacagaaat ggaaaaggaa ggaaaaattt caaaaattgg gcctgaaaat    360
ccatacaata ctccagtatt tgccataaag aaaaaagaca gtactaaatg gagaaaatta    420
gtagatttca gagaacttaa taagagaact caagatttct gggaagttca attaggaata    480
ccacatcctg cagggttaaa acagaaaaaa tcagtaacag tactggatgt gggcgatgca    540
tatttttcag ttcccttaga taaagacttc aggaagtata ctgcatttac catacctagt    600
ataaacaatg agacaccagg gattagatat cagtacaatg tgcttccaca gggatggaaa    660
ggatcaccag caatattcca gtgtagcatg acaaaaatct tagagccttt tagaaaacaa    720
aatccagaca tagtcatcta tcaatacatg gatgatttgt atgtaggatc tgacttagaa    780
atagggcagc atagaacaaa aatagaggaa ctgagacaac atctgttgag gtggggattt    840
accacaccag acaaaaaaca tcagaaagaa cctccattcc tttggatggg ttatgaactc    900
catcctgata aatggacagt acagcctata gtgctgccag aaaaggacag ctggactgtc    960
aatgacatac agaaattagt gggaaaattg aattgggcaa gtcagattta tgcagggatt   1020
aaagtaaggc aattatgtaa acttcttagg ggaaccaaag cactaacaga agtagtacca   1080
ctaacagaag aagcagagct agaactggca gaaaacaggg agattctaaa agaaccggta   1140
catggagtgt attatgaccc atcaaaagac ttaatagcag aaatacagaa gcaggggcaa   1200
ggccaatgga catatcaaat ttatcaagag ccatttaaaa atctgaaaac aggaaagtat   1260
gcaagaatga agggtgccca cactaatgat gtgaaacaat taacagaggc agtacaaaaa   1320
atagccacag aaagcatagt aatatgggga aagactccta aatttaaatt acccatacaa   1380
aaggaaacat gggaagcatg gtggacagag tattggcaag ccacctggat tcctgagtgg   1440
gagtttgtca ataccccctcc cttagtgaag ttatggtacc agttagagaa agaacccata   1500
ataggagcag aaactttcta tgtagatggg gcagccaata gggaaactaa attaggaaaa   1560
gcaggatatg taactgacag aggaagacaa aaagttgtcc ccctaacgga cacaacaaat   1620
cagaagactg agttacaagc aattcatcta gctttgcagg attcgggatt agaagtaaac   1680
atagtgacag actcacaata tgcattggga atcattcaag cacaaccaga taagagtgaa   1740
tcagagttag tcagtcaaat aatagagcag ttaataaaaa aggaaaaagt ctacctggca   1800
tgggtaccag cacacaaagg aattggagga aatgaacaag tagataaatt ggtcagtgct   1860
ggaatcagga aagtactatt tttagatgga atagataagg cccaagaaga acatgagaaa   1920
tatcacagta attggagagc aatggctagt gattttaacc taccacctgt agtagcaaaa   1980
gaaatagtag ccagctgtga taaatgtcag ctaaaagggg aagccatgca tggacaagta   2040
gactgtagcc caggaatatg gcagctagat tgtacacatt tagaaggaaa agttatcttg   2100
gtagcagttc atgtagccag tggatatata gaagcagaag taattccagc agagacaggg   2160
caagaaacag catacttcct cttaaaatta gcaggaagat ggccagtaaa aacagtacat   2220
acagacaatg gcagcaattt caccagtact acagttaagg ccgcctgttg gtgggcgggg   2280
```

atcaagcagg aatttggcat tccctacaat ccccaaagtc aaggagtaat agaatctatg 2340
aataaagaat taaagaaaat tataggacag gtaagagatc aggctgaaca tcttaagaca 2400
gcagtacaaa tggcagtatt catccacaat tttaaaagaa aaggggggat tggggggtac 2460
agtgcagggg aaagaatagt agacataata gcaacagaca tacaaactaa agaattacaa 2520
aaacaaatta caaaaattca aaattttcgg gtttattaca gggacagcag agatccagtt 2580
tggaaaggac cagcaaagct cctctggaaa ggtgaagggg cagtagtaat acaagataat 2640
agtgacataa aagtagtgcc aagaagaaaa gcaaagatca tcagggatta tggaaaacag 2700
atggcaggtg atgattgtgt ggcaagtaga caggatgagg attaa 2745

<210> SEQ ID NO 44
<211> LENGTH: 1586
<212> TYPE: DNA
<213> ORGANISM: artificial sequence
<220> FEATURE:
<223> OTHER INFORMATION: Rev, RRE and rabbit beta globin poly A DNA fragment

<400> SEQUENCE: 44
tctagaatgg caggaagaag cggagacagc gacgaagagc tcatcagaac agtcagactc 60
atcaagcttc tctatcaaag caacccacct cccaatcccg aggggacccg acaggcccga 120
aggaatagaa gaagaaggtg gagagagaga cagagacaga tccattcgat tagtgaacgg 180
atccttggca cttatctggg acgatctgcg gagcctgtgc ctcttcagct accaccgctt 240
gagagactta ctcttgattg taacgaggat tgtggaactt ctgggacgca gggggtggga 300
agccctcaaa tattggtgga atctcctaca atattggagt caggagctaa agaatagagg 360
agctttgttc cttgggttct tgggagcagc aggaagcact atgggcgcag cgtcaatgac 420
gctgacggta caggccagac aattattgtc tggtatagtg cagcagcaga acaatttgct 480
gagggctatt gaggcgcaac agcatctgtt gcaactcaca gtctggggca tcaagcagct 540
ccaggcaaga atcctggctg tggaaagata cctaaaggat caacagctcc tagatctttt 600
tccctctgcc aaaaattatg gggacatcat gaagcccctt gagcatctga cttctggcta 660
ataaaggaaa tttattttca ttgcaatagt gtgttggaat tttttgtgtc tctcactcgg 720
aaggacatat gggagggcaa atcatttaaa acatcagaat gagtatttgg tttagagttt 780
ggcaacatat gccatatgct ggctgccatg aacaaaggtg gctataaaga ggtcatcagt 840
atatgaaaca gccccctgct gtccattcct tattccatag aaaagccttg acttgaggtt 900
agattttttt tatattttgt tttgtgttat ttttttcttt aacatcccta aaattttcct 960
tacatgtttt actagccaga tttttcctcc tctcctgact actcccagtc atagctgtcc 1020
ctcttctctt atgaagatcc ctcgacctgc agcccaagct tggcgtaatc atggtcatag 1080
ctgtttcctg tgtgaaattg ttatccgctc acaattccac acaacatacg agccggaagc 1140
ataaagtgta aagcctgggg tgcctaatga gtgagctaac tcacattaat tgcgttgcgc 1200
tcactgcccg ctttccagtc gggaaacctg tcgtgccagc ggatccgcat ctcaattagt 1260
cagcaaccat agtcccgccc ctaactccgc ccatcccgcc cctaactccg cccagttccg 1320
cccattctcc gccccatggc tgactaattt tttttattta tgcagaggcc gaggccgcct 1380
cggcctctga gctattccag aagtagtgag gaggcttttt tggaggccta ggcttttgca 1440
aaaagctaac ttgtttattg cagcttataa tggttacaaa taaagcaata gcatcacaaa 1500
tttcacaaat aaagcatttt tttcactgca ttctagttgt ggtttgtcca aactcatcaa 1560
tgtatcttat cagcggccgc cccggg 1586

<210> SEQ ID NO 45
<211> LENGTH: 1614
<212> TYPE: DNA
<213> ORGANISM: artificial sequence
<220> FEATURE:
<223> OTHER INFORMATION: CAG enhancer/promoter/intron sequence DNA fragment

<400> SEQUENCE: 45
acgcgttagt tattaatagt aatcaattac ggggtcatta gttcatagcc catatatgga 60
gttccgcgtt acataactta cggtaaatgg cccgcctggc tgaccgccca acgacccccg 120
cccattgacg tcaataatga cgtatgttcc catagtaacg ccaataggga ctttccattg 180
acgtcaatgg gtggactatt tacggtaaac tgcccacttg gcagtacatc aagtgtatca 240
tatgccaagt acgcccccta ttgacgtcaa tgacggtaaa tggcccgcct ggcattatgc 300
ccagtacatg accttatggg actttcctac ttggcagtac atctacgtat tagtcatcgc 360
tattaccatg ggtcgaggtg agccccacgt tctgcttcac tctccccatc tcccccccct 420
ccccaccccc aattttgtat ttatttattt tttaattatt ttgtgcagcg atgggggcgg 480
gggggggggg ggcgcgcgcc aggcggggcg gggcggggcg aggggcgggg cggggcgagg 540
cggagaggtg cggcggcagc caatcagagc ggcgcgctcc gaaagtttcc ttttatggcg 600
aggcggcggc ggcggcggcc ctataaaaag cgaagcgcgc ggcgggcggg agtcgctgcg 660
ttgccttcgc cccgtgcccc gctccgcgcc gcctcgcgcc gcccgccccg gctctgactg 720
accgcgttac tcccacaggt gagcgggcgg gacggccctt ctcctccggg ctgtaattag 780
cgcttggttt aatgacggct cgtttctttt ctgtggctgc gtgaaagcct taaagggctc 840
cgggagggcc ctttgtgcgg ggggagcggc ctcggggggt gcgtgcgtgt gtgtgtgcgt 900
ggggagcgcc gcgtgcggcc cgcgctgccc ggcggctgtg agcgctgcgg gcgcggcgcg 960
gggctttgtg cgctccgcgt gtgcgcgagg ggagcgcggc cgggggcggt gccccgcggt 1020
gcgggggggc tgcgagggga acaaaggctg cgtgcggggt gtgtgcgtgg gggggtgagc 1080
agggggtgtg ggcgcggcgg tcgggctgta acccccccct gcaccccccct ccccgagttg 1140 ctgagcacgg cccggcttcg ggtgcggggc tccgtgcggg gcgtggcgcg gggctcgccg 1200
tgccgggcgg ggggtggcgg caggtggggg tgccgggcgg ggcggggccg cctcgggccg 1260
gggagggctc gggggagggg cgcggcggcc ccggagcgcc ggcggctgtc gaggcgcggc 1320
gagccgcagc cattgccttt tatggtaatc gtgcgagagg gcgcagggac ttcctttgtc 1380
ccaaatctgg cggagccgaa atctgggagg cgccgccgca ccccctctag cgggcgcggg 1440
cgaagcggtg cggcgccggc aggaaggaaa tgggcgggga gggccttcgt gcgtcgccgc 1500
gccgccgtcc ccttctccat ctccagcctc ggggctgccg caggggggacg gctgccttcg 1560 ggggggacgg ggcagggcgg ggttcggctt ctggcgtgtg accggcggga attc 1614

<210> SEQ ID NO 46
<211> LENGTH: 1531
<212> TYPE: DNA
<213> ORGANISM: Vesicular Stomatitis Indiana Virus

<400> SEQUENCE: 46
gaattcatga agtgcctttt gtacttagcc tttttattca ttggggtgaa ttgcaagttc 60
accatagttt ttccacacaa ccaaaaagga aactggaaaa atgttccttc taattaccat 120
tattgcccgt caagctcaga tttaaattgg cataatgact taataggcac agccttacaa 180
gtcaaaatgc ccaagagtca caaggctatt caagcagacg gttggatgtg tcatgcttcc 240
aaatgggtca ctacttgtga tttccgctgg tatggaccga agtatataac acattccatc 300
cgatccttca ctccatctgt agaacaatgc aaggaaagca ttgaacaaac gaaacaagga 360
acttggctga atccaggctt ccctcctcaa agttgtggat atgcaactgt gacggatgcc 420
gaagcagtga ttgtccaggt gactcctcac catgtgctgg ttgatgaata cacaggagaa 480
tgggttgatt cacagttcat caacggaaaa tgcagcaatt acatatgccc cactgtccat 540
aactctacaa cctggcattc tgactataag gtcaaagggc tatgtgattc taacctcatt 600
tccatggaca tcaccttctt ctcagaggac ggagagctat catccctggg aaaggagggc 660
acagggttca gaagtaacta ctttgcttat gaaactggag gcaaggcctg caaaatgcaa 720
tactgcaagc attggggagt cagactccca tcaggtgtct ggttcgagat ggctgataag 780
gatctctttg ctgcagccag attccctgaa tgcccagaag ggtcaagtat ctctgctcca 840
tctcagacct cagtggatgt aagtctaatt caggacgttg agaggatctt ggattattcc 900
ctctgccaag aaacctggag caaaatcaga gcgggtcttc caatctctcc agtggatctc 960
agctatcttg ctcctaaaaa cccaggaacc ggtcctgctt tcaccataat caatggtacc 1020
ctaaaatact ttgagaccag atacatcaga gtcgatattg ctgctccaat cctctcaaga 1080
atggtcggaa tgatcagtgg aactaccaca gaaagggaac tgtgggatga ctgggcacca 1140
tatgaagacg tggaaattgg acccaatgga gttctgagga ccagttcagg atataagttt 1200
cctttataca tgattggaca tggtatgttg gactccgatc ttcatcttag ctcaaaggct 1260
caggtgttcg aacatcctca cattcaagac gctgcttcgc aacttcctga tgatgagagt 1320
ttattttttg gtgatactgg gctatccaaa aatccaatcg agcttgtaga aggttggttc 1380
agtagttgga aaagctctat tgcctctttt ttctttatca tagggttaat cattggacta 1440
ttcttggttc tccgagttgg tatccatctt tgcattaaat taaagcacac caagaaaaga 1500
cagatttata cagacataga gatgagaatt c 1531

<210> SEQ ID NO 47
<211> LENGTH: 351
<212> TYPE: DNA
<213> ORGANISM: Rous Sarcoma Virus

<400> SEQUENCE: 47
atggcaggaa gaagcggaga cagcgacgaa gaactcctca aggcagtcag actcatcaag 60
tttctctatc aaagcaaccc acctcccaat cccgagggga cccgacaggc ccgaaggaat 120
agaagaagaa ggtggagaga gagacagaga cagatccatt cgattagtga acggatcctt 180
agcacttatc tgggacgatc tgcggagcct gtgcctcttc agctaccacc gcttgagaga 240
cttactcttg attgtaacga ggattgtgga acttctggga cgcagggggt gggaagccct 300
caaatattgg tggaatctcc tacaatattg gagtcaggag ctaaagaata g 351

<210> SEQ ID NO 48
<211> LENGTH: 884
<212> TYPE: DNA
<213> ORGANISM: artificial sequence
<220> FEATURE:
<223> OTHER INFORMATION: Rous Sarcoma Virus (RSV) promoter and Human
Immunodeficiency Virus (HIV) Rev DNA fragment

<400> SEQUENCE: 48
caattgcgat gtacgggcca gatatacgcg tatctgaggg gactagggtg tgtttaggcg 60
aaaagcgggg cttcggttgt acgcggttag gagtcccctc aggatatagt agtttcgctt 120
ttgcataggg agggggaaat gtagtcttat gcaatacact tgtagtcttg caacatggta 180
acgatgagtt agcaacatgc cttacaagga gagaaaaagc accgtgcatg ccgattggtg 240
gaagtaaggt ggtacgatcg tgccttatta ggaaggcaac agacaggtct gacatggatt 300
ggacgaacca ctgaattccg cattgcagag ataattgtat ttaagtgcct agctcgatac 360
aataaacgcc atttgaccat tcaccacatt ggtgtgcacc tccaagctcg agctcgttta 420
gtgaaccgtc agatcgcctg gagacgccat ccacgctgtt ttgacctcca tagaagacac 480
cgggaccgat ccagcctccc ctcgaagcta gcgattaggc atctcctatg gcaggaagaa 540
gcggagacag cgacgaagaa ctcctcaagg cagtcagact catcaagttt ctctatcaaa 600
gcaacccacc tcccaatccc gaggggaccc gacaggcccg aaggaataga agaagaaggt 660
ggagagagag acagagacag atccattcga ttagtgaacg gatccttagc acttatctgg 720
gacgatctgc ggagcctgtg cctcttcagc taccaccgct tgagagactt actcttgatt 780
gtaacgagga ttgtggaact tctgggacgc agggggtggg aagccctcaa atattggtgg 840
aatctcctac aatattggag tcaggagcta aagaatagtc taga 884

<210> SEQ ID NO 49
<211> LENGTH: 511
<212> TYPE: DNA
<213> ORGANISM: Homo sapiens

<400> SEQUENCE: 49
ggggttgggg ttgcgccttt tccaaggcag ccctgggttt gcgcagggac gcggctgctc 60
tgggcgtggt tccgggaaac gcagcggcgc cgaccctggg tctcgcacat tcttcacgtc 120
cgttcgcagc gtcacccgga tcttcgccgc tacccttgtg ggccccccgg cgacgcttcc 180
tgctccgccc ctaagtcggg aaggttcctt gcggttcgcg gcgtgccgga cgtgacaaac 240
ggaagccgca cgtctcacta gtaccctcgc agacggacag cgccagggag caatggcagc 300
gcgccgaccg cgatgggctg tggccaatag cggctgctca gcagggcgcg ccgagagcag 360
cggccgggaa ggggcggtgc gggaggcggg gtgtggggcg gtagtgtggg ccctgttcct 420
gcccgcgcgg tgttccgcat tctgcaagcc tccggagcgc acgtcggcag tcggctccct 480
cgttgaccga atcaccgacc tctctcccca g 511

<210> SEQ ID NO 50
<211> LENGTH: 1162
<212> TYPE: DNA
<213> ORGANISM: Homo sapiens

<400> SEQUENCE: 50
gcgccgggtt ttggcgcctc ccgcgggcgc ccccctcctc acggcgagcg ctgccacgtc 60
agacgaaggg cgcaggagcg ttcctgatcc ttccgcccgg acgctcagga cagcggcccg 120
ctgctcataa gactcggcct tagaacccca gtatcagcag aaggacattt taggacggga 180
cttgggtgac tctagggcac tggttttctt tccagagagc ggaacaggcg aggaaaagta 240
gtcccttctc ggcgattctg cggagggatc tccgtggggc ggtgaacgcc gatgattata 300
taaggacgcg ccgggtgtgg cacagctagt tccgtcgcag ccgggatttg ggtcgcggtt 360
cttgtttgtg gatcgctgtg atcgtcactt ggtgagttgc gggctgctgg gctggccggg 420

-continued

```
gctttcgtgg ccgccgggcc gctcggtggg acggaagcgt gtggagagac cgccaagggc    480

tgtagtctgg gtccgcgagc aaggttgccc tgaactgggg gttgggggga gcgcacaaaa    540

tggcggctgt tcccgagtct tgaatggaag acgcttgtaa ggcgggctgt gaggtcgttg    600

aaacaaggtg gggggcatgg tgggcggcaa gaacccaagg tcttgaggcc ttcgctaatg    660

cgggaaagct cttattcggg tgagatgggc tggggcacca tctggggacc ctgacgtgaa    720

gtttgtcact gactggagaa ctcgggtttg tcgtctggtt gcgggggcgg cagttatgcg    780

gtgccgttgg gcagtgcacc cgtacctttg ggagcgcgcg cctcgtcgtg tcgtgacgtc    840

acccgttctg ttggcttata atgcagggtg gggccacctg ccggtaggtg tgcggtaggc    900

ttttctccgt cgcaggacgc agggttcggg cctagggtag gctctcctga atcgacaggc    960

gccggacctc tggtgagggg agggataagt gaggcgtcag tttctttggt cggttttatg   1020

tacctatctt cttaagtagc tgaagctccg gttttgaact atgcgctcgg ggttggcgag   1080

tgtgttttgt gaagtttttt aggcaccttt tgaaatgtaa tcatttgggt caatatgtaa   1140

ttttcagtgt tagactagta aa                                            1162


<210> SEQ ID NO 51
<211> LENGTH: 120
<212> TYPE: DNA
<213> ORGANISM: Simian virus 40

<400> SEQUENCE: 51

gtttattgca gcttataatg gttacaaata aagcaatagc atcacaaatt tcacaaataa     60

agcatttttt tcactgcatt ctagttgtgg tttgtccaaa ctcatcaatg tatcttatca    120


<210> SEQ ID NO 52
<211> LENGTH: 227
<212> TYPE: DNA
<213> ORGANISM: Bos taurus

<400> SEQUENCE: 52

gactgtgcct tctagttgcc agccatctgt tgtttgcccc tcccccgtgc cttccttgac     60

cctggaaggt gccactccca ctgtcctttc ctaataaaat gaggaaattg catcgcattg    120

tctgagtagg tgtcattcta ttctgggggg tggggtgggg caggacagca agggggagga    180

ttgggaagac aatagcaggc atgctgggga tgcggtgggc tctatgg                  227


<210> SEQ ID NO 53
<211> LENGTH: 1695
<212> TYPE: DNA
<213> ORGANISM: Feline Endogenous Virus

<400> SEQUENCE: 53

atgaaactcc caacaggaat ggtcatttta tgtagcctaa taatagttcg ggcagggttt     60

gacgaccccc gcaaggctat cgcattagta caaaaacaac atggtaaacc atgcgaatgc    120

agcggagggc aggtatccga ggccccaccg aactccatcc aacaggtaac ttgcccaggc    180

aagacggcct acttaatgac caaccaaaaa tggaaatgca gagtcactcc aaaaaatctc    240

acccctagcg ggggagaact ccagaactgc ccctgtaaca ctttccagga ctcgatgcac    300

agttcttgtt atactgaata ccggcaatgc agggcgaata ataagacata ctacacggcc    360

accttgctta aaatacggtc tgggagcctc aacgaggtac agatattaca aaaccccaat    420

cagctcctac agtccccttg taggggctct ataaatcagc ccgtttgctg gagtgccaca    480

gcccccatcc atatctccga tggtggagga cccctcgata ctaagagagt gtggacagtc    540
```

caaaaaaggc tagaacaaat tcataaggct atgcatcctg aacttcaata ccacccctta 600
gccctgccca aagtcagaga tgaccttagc cttgatgcac ggacttttga tatcctgaat 660
accactttta ggttactcca gatgtccaat tttagccttg cccaagattg ttggctctgt 720
ttaaaactag gtacccctac ccctcttgcg atacccactc cctctttaac ctactcccta 780
gcagactccc tagcgaatgc ctcctgtcag attatacctc ccctcttggt tcaaccgatg 840
cagttctcca actcgtcctg tttatcttcc cctttcatta acgatacgga acaaatagac 900
ttaggtgcag tcacctttac taactgcacc tctgtagcca atgtcagtag tcctttatgt 960
gccctaaacg ggtcagtctt cctctgtgga aataacatgg catacaccta tttaccccaa 1020
aactggacag gactttgcgt ccaagcctcc ctcctccccg acattgacat catcccgggg 1080
gatgagccag tccccattcc tgccattgat cattatatac atagacctaa acgagctgta 1140
cagttcatcc ctttactagc tggactggga atcaccgcag cattcaccac cggagctaca 1200
ggcctaggtg tctccgtcac ccagtataca aaattatccc atcagttaat atctgatgtc 1260
caagtcttat ccggtaccat acaagattta caagaccagg tagactcgtt agctgaagta 1320
gttctccaaa ataggagggg actggaccta ctaacggcag aacaaggagg aatttgttta 1380
gccttacaag aaaaatgctg tttttatgct aacaagtcag gaattgtgag aaacaaaata 1440
agaaccctac aagaagaatt acaaaaacgc agggaaagcc tggcatccaa ccctctctgg 1500
accgggctgc agggctttct tccgtacctc ctacctctcc tgggacccct actcaccctc 1560
ctactcatac taaccattgg gccatgcgtt ttcaatcgat tggtccaatt tgttaaagac 1620
aggatctcag tggtccaggc tctggttttg actcagcaat atcaccagct aaaacccata 1680
gagtacgagc catga 1695

<210> SEQ ID NO 54
<211> LENGTH: 2013
<212> TYPE: DNA
<213> ORGANISM: Gibbon Ape Leukemia Virus

<400> SEQUENCE: 54
atgcttctca cctcaagccc gcaccacctt cggcaccaga tgagtcctgg gagctggaaa 60
agactgatca tcctcttaag ctgcgtattc ggagacggca aaacgagtct gcagaataag 120
aacccccacc agcctgtgac cctcacctgg caggtactgt cccaaactgg ggacgttgtc 180
tgggacaaaa aggcagtcca gccccttttgg acttggtggc cctctcttac acctgatgta 240
tgtgccctgg cggccggtct tgagtcctgg gatatcccgg gatccgatgt atcgtcctct 300
aaaagagtta gacctcctga ttcagactat actgccgctt ataagcaaat cacctgggga 360
gccatagggt gcagctaccc tcgggctagg accaggatgg caaattcccc cttctacgtg 420
tgtccccgag ctggccgaac ccattcagaa gctaggaggt gtgggggggct agaatcccta 480 tactgtaaag aatggagttg tgagaccacg ggtaccgttt attggcaacc caagtcctca 540
tgggacctca taactgtaaa atgggaccaa aatgtgaaat gggagcaaaa atttcaaaag 600
tgtgaacaaa ccggctggtg taaccccctc aagatagact tcacagaaaa aggaaaactc 660
tccagagatt ggataacgga aaaaacctgg gaattaaggt tctatgtata tggacaccca 720
ggcatacagt tgactatccg cttagaggtc actaacatgc cggttgtggc agtgggccca 780
gaccctgtcc ttgcggaaca gggacctcct agcaagcccc tcactctccc tctctcccca 840
cggaaagcgc cgcccacccc tctacccccg gcggctagtg agcaaacccc tgcggtgcat 900

-continued

```
ggagaaactg ttaccctaaa ctctccgcct cccaccagtg gcgaccgact ctttggcctt    960
gtgcaggggg ccttcctaac cttgaatgct accaacccag gggccactaa gtcttgctgg   1020
ctctgtttgg gcatgagccc cccttattat gaagggatag cctcttcagg agaggtcgct   1080
tatacctcca accatacccg atgccactgg ggggcccaag gaaagcttac cctcactgag   1140
gtctccggac tcgggtcatg catagggaag gtgcctctta cccatcaaca tctttgcaac   1200
cagaccttac ccatcaattc ctctaaaaac catcagtatc tgctcccctc aaaccatagc   1260
tggtgggcct gcagcactgg cctcaccccc tgcctctcca cctcagtttt taatcagtct   1320
aaagacttct gtgtccaggt ccagctgatc cccgcatct attaccattc tgaagaaacc    1380
ttgttacaag cctatgacaa atcacccccc aggtttaaaa gagagcctgc ctcacttacc   1440
ctagctgtct tcctggggtt agggattgcg gcaggtatag gtactggctc aaccgcccta   1500
attaaagggc ccatagacct ccagcaaggc ctaaccagcc tccaaatcgc cattgacgct   1560
gacctccggg cccttcagga ctcaatcagc aagctagagg actcactgac ttccctatct   1620
gaggtagtac tccaaaatag gagaggcctt gacttactat tccttaaaga aggaggcctc   1680
tgcgcggccc taaaagaaga gtgctgtttt tatgtagacc actcaggtgc agtacgagac   1740
tccatgaaaa aacttaaaga aagactagat aaaagacagt tagagcgcca gaaaaaccaa   1800
aactggtatg aagggtggtt caataactcc ccttggttta ctaccctact atcaaccatc   1860
gctgggcccc tattgctcct ccttttgtta ctcactcttg ggccctgcat catcaataaa   1920
ttaatccaat tcatcaatga taggataagt gcagtcaaaa ttttagtcct tagacagaaa   1980
tatcagaccc tagataacga ggaaaacctt taa                                2013
```

<210> SEQ ID NO 55
<211> LENGTH: 1530
<212> TYPE: DNA
<213> ORGANISM: Rabies virus

<400> SEQUENCE: 55

```
atggttccgc aggttctttt gtttgtactc cttctgggtt tttcgttgtg tttcgggaag     60
ttccccattt acacgatacc agacgaactt ggtccctgga gccctattga catacaccat    120
ctcagctgtc caaataacct ggttgtggag gatgaaggat gtaccaacct gtccgagttc    180
tcctacatgg aactcaaagt gggatacatc tcagccatca aagtgaacgg gttcacttgc    240
acaggtgttg tgacagaggc agagacctac accaactttg ttggttatgt cacaaccaca    300
ttcaagagaa agcatttccg ccccaccccca gacgcatgta gagccgcgta taactggaag    360
atggccggtg accccagata tgaagagtcc ctacacaatc catacccga ctaccactgg     420
cttcgaactg taagaaccac caaagagtcc ctcattatca tatccccaag tgtgacagat    480
ttggacccat atgacaaatc ccttcactca agggtcttcc ctggcggaaa gtgctcagga    540
ataacggtgt cctctaccta ctgctcaact aaccatgatt acaccatttg gatgcccgag    600
aatccgagac caaggacacc ttgtgacatt tttaccaata gcagagggaa gagagcatcc    660
aacgggaaca agacttgcgg ctttgtggat gaaagaggcc tgtataagtc tctaaaagga    720
gcatgcaggc tcaagttatg tggagttctt ggacttagac ttatggatgg aacatgggtc    780
gcgatgcaaa catcagatga gaccaaatgg tgccctccag atcagttggt gaatttgcac    840
gactttcgct cagacgagat cgagcatctc gttgtggagg agttagttaa gaaaagagag    900
gaatgtctgg atgcattaga gtccatcatg accaccaagt cagtaagttt cagacgtctc    960
agtcacctga gaaaacttgt cccagggttt ggaaaagcat ataccatatt caacaaaacc   1020
```

ttgatggagg ctgatgctca ctacaagtca gtccggacct ggaatgagat catcccctca 1080
aaagggtgtt tgaaagttgg aggaaggtgc catcctcatg tgaacggggt gtttttcaat 1140
ggtataatat tagggcctga cgaccatgtc ctaatcccag agatgcaatc atccctcctc 1200
cagcaacata tggagttgtt ggaatcttca gttatccccc tgatgcaccc cctggcagac 1260
ccttctacag ttttcaaaga aggtgatgag gctgaggatt ttgttgaagt tcacctcccc 1320
gatgtgtaca aacagatctc aggggttgac ctgggtctcc cgaactgggg aaagtatgta 1380
ttgatgactg caggggccat gattggcctg gtgttgatat tttccctaat gacatggtgc 1440
agagttggta tccatctttg cattaaatta aagcacacca agaaaagaca gatttataca 1500
gacatagaga tgaaccgact tggaaagtaa 1530

<210> SEQ ID NO 56
<211> LENGTH: 1497
<212> TYPE: DNA
<213> ORGANISM: Lymphocytic Choriomeningitis Virus

<400> SEQUENCE: 56
atgggtcaga ttgtgacaat gtttgaggct ctgcctcaca tcatcgatga ggtgatcaac 60
attgtcatta ttgtgcttat cgtgatcacg ggtatcaagg ctgtctacaa ttttgccacc 120
tgtgggatat tcgcattgat cagtttccta cttctggctg gcaggtcctg tggcatgtac 180
ggtcttaagg gacccgacat ttacaaagga gtttaccaat ttaagtcagt ggagtttgat 240
atgtcacatc tgaacctgac catgcccaac gcatgttcag ccaacaactc ccaccattac 300
atcagtatgg ggacttctgg actagaattg accttcacca atgattccat catcagtcac 360
aacttttgca atctgacctc tgccttcaac aaaaagacct ttgaccacac actcatgagt 420
atagtttcga gcctacacct cagtatcaga gggaactcca actataaggc agtatcctgc 480
gacttcaaca atggcataac catccaatac aacttgacat tctcagatcg acaaagtgct 540
cagagccagt gtagaacctt cagaggtaga gtcctagata tgtttagaac tgccttcggg 600
gggaaataca tgaggagtgg ctggggctgg acaggctcag atggcaagac cacctggtgt 660
agccagacga gttaccaata cctgattata caaaatagaa cctgggaaaa ccactgcaca 720
tatgcaggtc cttttgggat gtccaggatt ctcctttccc aagagaagac taagttcttc 780
actaggagac tagcgggcac attcacctgg actttgtcag actcttcagg ggtggagaat 840
ccaggtggtt attgcctgac caaatggatg attcttgctg cagagcttaa gtgtttcggg 900
aacacagcag ttgcgaaatg caatgtaaat catgatgccg aattctgtga catgctgcga 960
ctaattgact acaacaaggc tgctttgagt aagttcaaag aggacgtaga atctgccttg 1020
cacttattca aaacaacagt gaattctttg atttcagatc aactactgat gaggaaccac 1080
ttgagagatc tgatgggggt gccatattgc aattactcaa agttttggta cctagaacat 1140
gcaaagaccg gcgaaactag tgtccccaag tgctggcttg tcaccaatgg ttcttactta 1200
aatgagaccc acttcagtga tcaaatcgaa caggaagccg ataacatgat tacagagatg 1260
ttgaggaagg attacataaa gaggcagggg agtacccccc tagcattgat ggaccttctg 1320
atgttttcca catctgcata tctagtcagc atcttcctgc accttgtcaa aataccaaca 1380
cacaggcaca taaaaggtgg ctcatgtcca aagccacacc gattaaccaa caaaggaatt 1440
tgtagttgtg gtgcatttaa ggtgcctggt gtaaaaaccg tctggaaaag acgctga 1497

<210> SEQ ID NO 57

<211> LENGTH: 1692
<212> TYPE: DNA
<213> ORGANISM: Fowl Plague virus

<400> SEQUENCE: 57
atgaacactc aaatcctggt tttcgccctt gtggcagtca tccccacaaa tgcagacaaa 60
atttgtcttg gacatcatgc tgtatcaaat ggcaccaaag taaacacact cactgagaga 120
ggagtagaag ttgtcaatgc aacggaaaca gtggagcgga caaacatccc caaaatttgc 180
tcaaaaggga aaagaaccac tgatcttggc caatgcggac tgttagggac cattaccgga 240
ccacctcaat gcgaccaatt tctagaattt tcagctgatc taataatcga gagacgagaa 300
ggaaatgatg tttgttaccc ggggaagttt gttaatgaag aggcattgcg acaaatcctc 360
agaggatcag gtgggattga caaagaaaca atgggattca catatagtgg aataaggacc 420
aacggaacaa ctagtgcatg tagaagatca gggtcttcat tctatgcaga aatggagtgg 480
ctcctgtcaa atacagacaa tgctgctttc ccacaaatga caaaatcata caaaaacaca 540
aggagagaat cagctctgat agtctgggga atccaccatt caggatcaac caccgaacag 600
accaaactat atgggagtgg aaataaactg ataacagtcg ggagttccaa atatcatcaa 660
tcttttgtgc cgagtccagg aacacgaccg cagataaatg gccagtccgg acggattgat 720
tttcattggt tgatcttgga tcccaatgat acagttactt ttagtttcaa tggggctttc 780
atagctccaa atcgtgccag cttcttgagg ggaaagtcca tggggatcca gagcgatgtg 840
caggttgatg ccaattgcga aggggaatgc taccacagtg gagggactat aacaagcaga 900
ttgccttttc aaaacatcaa tagcagagca gttggcaaat gcccaagata tgtaaaacag 960
gaaagtttat tattggcaac tgggatgaag aacgttcccg aaccttccaa aaaaaggaaa 1020
aaaagaggcc tgtttggcgc tatagcaggg tttattgaaa atggttggga aggtctggtc 1080
gacgggtggt acggtttcag gcatcagaat gcacaaggag aaggaactgc agcagactac 1140
aaaagcaccc aatcggcaat tgatcagata accggaaagt taaatagact cattgagaaa 1200
accaaccagc aatttgagct aatagataat gaattcactg aggtggaaaa gcagattggc 1260
aatttaatta actggaccaa agactccatc acagaagtat ggtcttacaa tgctgaactt 1320
cttgtggcaa tggaaaacca gcacactatt gatttggctg attcagagat gaacaagctg 1380
tatgagcgag tgaggaaaca attaagggaa aatgctgaag aggatggcac tggttgcttt 1440
gaaatttttc ataaatgtga cgatgattgt atggctagta taaggaacaa tacttatgat 1500
cacagcaaat acagagaaga agcgatgcaa aatagaatac aaattgaccc agtcaaattg 1560
agtagtggct acaaagatgt gatactttgg tttagcttcg gggcatcatg ctttttgctt 1620
cttgccattg caatgggcct tgttttcata tgtgtgaaga acggaaacat gcggtgcact 1680
atttgtatat aa 1692

<210> SEQ ID NO 58
<211> LENGTH: 1266
<212> TYPE: DNA
<213> ORGANISM: Ross River Virus

<400> SEQUENCE: 58
agtgtaacag agcactttaa tgtgtataag gctactagac catacctagc acattgcgcc 60
gattgcgggg acgggtactt ctgctatagc ccagttgcta tcgaggagat ccgagatgag 120
gcgtctgatg gcatgcttaa gatccaagtc tccgcccaaa taggtctgga caaggcaggc 180
acccacgccc acacgaagct ccgatatatg gctggtcatg atgttcagga atctaagaga 240

-continued gattccttga gggtgtacac gtccgcagcg tgctccatac atgggacgat gggacacttc 300
atcgtcgcac actgtccacc aggcgactac ctcaaggttt cgttcgagga cgcagattcg 360
cacgtgaagg catgtaaggt ccaatacaag cacaatccat tgccggtggg tagagagaag 420
ttcgtggtta gaccacactt tggcgtagag ctgccatgca cctcatacca gctgacaacg 480
gctcccaccg acgaggagat tgacatgcat acaccgccag atataccgga tcgcaccctg 540
ctatcacaga cggcgggcaa cgtcaaaata acagcaggcg gcaggactat caggtacaac 600
tgtacctgcg gccgtgacaa cgtaggcact accagtactg acaagaccat caacacatgc 660
aagattgacc aatgccatgc tgccgtcacc agccatgaca aatggcaatt tacctctcca 720
tttgttccca gggctgatca gacagctagg aaaggcaagg tacacgttcc gttccctctg 780
actaacgtca cctgccgagt gccgttggct cgagcgccgg atgccaccta tggtaagaag 840
gaggtgaccc tgagattaca cccagatcat ccgacgctct tctcctatag gagtttagga 900
gccgaaccgc acccgtacga ggaatgggtt gacaagttct ctgagcgcat catcccagtg 960
acggaagaag ggattgagta ccagtggggc aacaacccgc cggtctgcct gtgggcgcaa 1020
ctgacgaccg agggcaaacc ccatggctgg ccacatgaaa tcattcagta ctattatgga 1080
ctataccccg ccgccactat tgccgcagta tccggggcga gtctgatggc cctcctaact 1140
ctggcggcca catgctgcat gctggccacc gcgaggagaa agtgcctaac accgtacgcc 1200
ctgacgccag gagcggtggt accgttgaca ctggggctgc tttgctgcgc accgagggcg 1260
aatgca 1266

<210> SEQ ID NO 59
<211> LENGTH: 1266
<212> TYPE: DNA
<213> ORGANISM: Murine Leukemia virus

<400> SEQUENCE: 59
agtgtaacag agcactttaa tgtgtataag gctactagac catacctagc acattgcgcc 60
gattgcgggg acgggtactt ctgctatagc ccagttgcta tcgaggagat ccgagatgag 120
gcgtctgatg gcatgcttaa gatccaagtc tccgcccaaa taggtctgga caaggcaggc 180
acccacgccc acacgaagct ccgatatatg gctggtcatg atgttcagga atctaagaga 240
gattccttga gggtgtacac gtccgcagcg tgctccatac atgggacgat gggacacttc 300
atcgtcgcac actgtccacc aggcgactac ctcaaggttt cgttcgagga cgcagattcg 360
cacgtgaagg catgtaaggt ccaatacaag cacaatccat tgccggtggg tagagagaag 420
ttcgtggtta gaccacactt tggcgtagag ctgccatgca cctcatacca gctgacaacg 480
gctcccaccg acgaggagat tgacatgcat acaccgccag atataccgga tcgcaccctg 540
ctatcacaga cggcgggcaa cgtcaaaata acagcaggcg gcaggactat caggtacaac 600
tgtacctgcg gccgtgacaa cgtaggcact accagtactg acaagaccat caacacatgc 660
aagattgacc aatgccatgc tgccgtcacc agccatgaca aatggcaatt tacctctcca 720
tttgttccca gggctgatca gacagctagg aaaggcaagg tacacgttcc gttccctctg 780
actaacgtca cctgccgagt gccgttggct cgagcgccgg atgccaccta tggtaagaag 840
gaggtgaccc tgagattaca cccagatcat ccgacgctct tctcctatag gagtttagga 900
gccgaaccgc acccgtacga ggaatgggtt gacaagttct ctgagcgcat catcccagtg 960
acggaagaag ggattgagta ccagtggggc aacaacccgc cggtctgcct gtgggcgcaa 1020
ctgacgaccg agggcaaacc ccatggctgg ccacatgaaa tcattcagta ctattatgga 1080
ctataccccg ccgccactat tgccgcagta tccggggcga gtctgatggc cctcctaact 1140
ctggcggcca catgctgcat gctggccacc gcgaggagaa agtgcctaac accgtacgcc 1200
ctgacgccag gagcggtggt accgttgaca ctggggctgc tttgctgcgc accgagggcg 1260
aatgca 1266

<210> SEQ ID NO 60
<211> LENGTH: 2030
<212> TYPE: DNA
<213> ORGANISM: Ebola virus

<400> SEQUENCE: 60
atgggtgtta caggaatatt gcagttacct cgtgatcgat tcaagaggac atcattcttt 60
ctttgggtaa ttatcctttt ccaaagaaca ttttccatcc cacttggagt catccacaat 120
agcacattac aggttagtga tgtcgacaaa ctggtttgcc gtgacaaact gtcatccaca 180
aatcaattga gatcagttgg actgaatctc gaagggaatg gagtggcaac tgacgtgcca 240
tctgcaacta aaagatgggg cttcaggtcc ggtgtcccac caaaggtggt caattatgaa 300
gctggtgaat gggctgaaaa ctgctacaat cttgaaatca aaaaacctga cgggagtgag 360
tgtctaccag cagcgccaga cgggattcgg ggcttccccc ggtgccggta tgtgcacaaa 420
gtatcaggaa cgggaccgtg tgccggagac tttgccttcc acaaagaggg tgctttcttc 480
ctgtatgacc gacttgcttc cacagttatc taccgaggaa cgactttcgc tgaaggtgtc 540
gttgcatttc tgatactgcc ccaagctaag aaggacttct tcagctcaca cccccttgaga 600 gagccggtca atgcaacgga ggacccgtct agtggctact attctaccac aattagatat 660
caagctaccg gttttggaac caatgagaca gagtatttgt tcgaggttga caatttgacc 720
tacgtccaac ttgaatcaag attcacacca cagtttctgc tccagctgaa tgagacaata 780
tatacaagtg ggaaaaggag caataccacg ggaaaactaa tttggaaggt caaccccgaa 840
attgatacaa caatcgggga gtgggccttc tgggaaacta aaaaaacctc actagaaaaa 900
ttcgcagtga agagttgtct ttcacagctg tatcaaacag agccaaaaac atcagtggtc 960
agagtccggc gcgaacttct tccgacccag ggaccaacac aacaactgaa gaccacaaaa 1020
tcatggcttc agaaaattcc tctgcaatgg ttcaagtgca cagtcaagga agggaagctg 1080
cagtgtcgca tctgacaacc cttgccacaa tctccacgag tcctcaaccc cccacaacca 1140
aaccaggtcc ggacaacagc acccacaata cacccgtgta taaacttgac atctctgagg 1200
caactcaagt tgaacaacat caccgcagaa cagacaacga cagcacagcc tccgacactc 1260
cccccgccac gaccgcagcc ggacccctaa aagcagagaa caccaacacg agcaagggta 1320
ccgacctcct ggaccccgcc accacaacaa gtccccaaaa ccacagcgag accgctggca 1380
acaacaacac tcatcaccaa gataccggag aagagagtgc cagcagcggg aagctaggct 1440
taattaccaa tactattgct ggagtcgcag gactgatcac aggcgggagg agagctcgaa 1500
gagaagcaat tgtcaatgct caacccaaat gcaaccctaa tttacattac tggactactc 1560
aggatgaagg tgctgcaatc ggactggcct ggataccata tttcgggcca gcagccgagg 1620
gaatttacat agaggggctg atgcacaatc aagatggttt aatctgtggg ttgagacagc 1680
tggccaacga gacgactcaa gctcttcaac tgttcctgag agccacaacc gagctacgca 1740
ccttttcaat cctcaaccgt aaggcaattg atttcttgct gcagcgatgg ggcggcacat 1800
gccacatttt gggaccggac tgctgtatcg aaccacatga ttggaccaag aacataacag 1860

-continued

```
acaaaattga tcagattatt catgattttg ttgataaaac ccttccggac caggggggaca   1920

atgacaattg gtggacagga tggagacaat ggataccggc aggtattgga gttacaggcg   1980

ttataattgc agttatcgct ttattctgta tatgcaaatt tgtcttttag               2030


<210> SEQ ID NO 61
<211> LENGTH: 49
<212> TYPE: DNA
<213> ORGANISM: artificial sequence
<220> FEATURE:
<223> OTHER INFORMATION: Control shRNA sequence

<400> SEQUENCE: 61

gccgctttgt aggatagagc tcgagctcta tcctacaaag cggctttttt                  49
```